United States Patent [19]
Acklin et al.

[11] Patent Number: 6,080,743
[45] Date of Patent: Jun. 27, 2000

[54] 2,3-DIOXO-1,2,3,4-TETRAHYDRO-QUINOXALINYL DERIVATIVES

[75] Inventors: Pierre Acklin, Birsfelden, Switzerland; Hans Allgeier, Lörrach, Germany; Yves Auberson, Allschwil, Switzerland; Michel Biollaz, Binningen, Switzerland; Robert Moretti, Vaulruz, Switzerland; Silvio Ofner, Münchenstein, Switzerland; Siem Jacob Veenstra, Lörrach, Germany

[73] Assignee: Novartis AG, Basel, Switzerland

[21] Appl. No.: 09/029,525

[22] PCT Filed: Aug. 19, 1996

[86] PCT No.: PCT/EP96/03644

§ 371 Date: Feb. 27, 1998

§ 102(e) Date: Feb. 27, 1998

[87] PCT Pub. No.: WO97/08155

PCT Pub. Date: Mar. 6, 1997

[30] Foreign Application Priority Data

| Aug. 31, 1995 | [CH] | Switzerland | 2479/95 |
| Sep. 27, 1995 | [CH] | Switzerland | 2734/95 |
| Sep. 28, 1995 | [CH] | Switzerland | 2747/95 |
| May 10, 1996 | [CH] | Switzerland | 1213/96 |
| Jun. 28, 1996 | [CH] | Switzerland | 1630/96 |

[51] Int. Cl.$^7$ ........................ C07D 241/44; A61K 31/495
[52] U.S. Cl. ........................ 514/249; 544/354
[58] Field of Search ............... 544/354; 514/249

[56] References Cited

U.S. PATENT DOCUMENTS 4,156,734  5/1979  Stone .

FOREIGN PATENT DOCUMENTS

| 371564 | 6/1990 | European Pat. Off. . |
| WO 91/01724 | 2/1991 | WIPO . |
| WO 95/12417 | 5/1995 | WIPO . |
| WO 96/08485 | 3/1996 | WIPO . |
| WO 96/09295 | 3/1996 | WIPO . |

*Primary Examiner*—Robert Cerstl
*Attorney, Agent, or Firm*—Joseph J. Borovian

[57] ABSTRACT

2,3-Dioxo-1,2,3,4-tetrahydro-quinoxalinyl derivatives of formula (I),

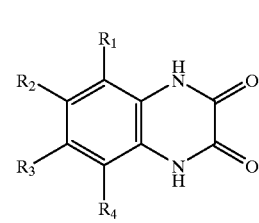

wherein one of the radicals $R_1$, and $R_2$ is a group $R_5$ and the other is a group of formula —$CH(R_6)$—alk—$R_7$ (Ia), —alk—$CH(R_6$–$R_7$ (Ib), —alk—$N(R_8)$—X—$R_7$ (Ic), —alk—$N^+(R_8)(R^9)$—X—$R_7A^-$ (Id), —alk—O—X—$R_7$ (Ie) or —alk—S—X—$R_7$ (If), $R_3$, $R_4$ and $R_5$ are each independently of the others hydrogen, lower alkyl, halogen, trifluoromethyl, cyano or nitro, $R_6$ is unsubstituted or lower alkylated and/or lower alkanoylated amino, $R_7$ is hydrogen; an aliphatic, cycloaliphatic or heterocycloaliphatic radical; cyano; acyl derived from carbonic acid or from a semiester or semiamide of carbonic acid, from sulfuric acid or from an aliphatic or aromatic sulfonic acid or from phosphoric acid or from a phosphonic acid ester; amino that is unsubstituted or aliphatically or araliphatically substituted and/or substituted by aliphatic, araliphatic or aromatic acyl; or an aromatic or heteroaromatic radical, $R_8$ is hydrogen; an aliphatic or araliphatic radical; or acyl derived from an aliphatic or araliphatic carboxylic acid or from an aliphatic or araliphatic semiester of carbonic acid, or $R_7$ and $R_8$, together with X and the nitrogen atom bonding $R_8$ and X, form an unsubstitued or substituted mono- or di-azaxycloalkyl, azoxacycloalkyl, azathiacycloalkyl or optionally oxidised thiacycloalkyl radical bonded via a nitrogen atom, or an unsubstituted or substituted, optionally partially hxdrogenated aryl or heteroaryl radical, $R_9$ is an aliphatic or araliphatic radical, or $R_7$, $R_8$ and $R_9$ together with X and the nitrogen atom bonding $R_8$, $R_9$ and X, form an unsubstituted or substituted quaternary heteroaryl radical bonded via the quaternary nitrogen atom, with $A^-$ being the anion of a protonic acid, alk is lower alkylene, and X (unless, together with $R_7$ and $R_8$ and the nitrogen atom bonding $R_8$ and X or together with the nitrogen atom bonding $R_8$, $R_9$ and X, it forms part of one of the mentioned ring systems) is a divalent aliphatic, cycloaliphatic or araliphatic radical or a direct bond, and the pharmaceutically acceptable salts thereof can be used in the preparation of a medicament for the treatment of pathological conditions that are responsive to blocking of AMPA, kainate and/or glycine binding sites of the NMDA receptor.

16 Claims, No Drawings

2,3-DIOXO-1,2,3,4-TETRAHYDRO-QUINOXALINYL DERIVATIVES

The invention relates to the use of 2,3-dioxo-1,2,3,4-tetrahydro-quinoxalinyl derivatives of formula I

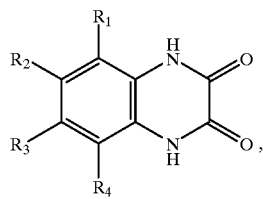

(I)

wherein
one of the radicals $R_1$ and $R_2$ is a group $R_5$ and the other is a group of formula —CH($R_6$)—alk—$R_7$ (Ia), —alk—CH($R_6$)—$R_7$ (Ib), —alk—N($R_8$)—X—$R_7$ (Ic), —alk—N$^+$($R_8$)($R_9$)—X—$R_7$A (Id), —alk—O—X—$R_7$ (Ie) or —alk—S—X—$R_7$ (If), $R_3$, $R_4$ and $R_5$ are each independently of the others hydrogen, lower alkyl, halogen, trifluoromethyl, cyano or nitro, $R_6$ is unsubstituted or lower alkylated and/or lower alkanoylated amino, $R_7$ is hydrogen; an aliphatic, cycloaliphatic or heterocycloaliphatic radical; cyano; acyl derived from carbonic acid or from a semiester or semiamide of carbonic acid, from sulfuric acid or from an aliphatic or aromatic sulfonic acid or from phosphoric acid or from a phosphonic acid ester; amino that is unsubstituted or aliphatically or araliphatically substituted and/or substituted by aliphatic, araliphatic or aromatic acyl; or an aromatic or heteroaromatic radical, $R_8$ is hydrogen; an aliphatic or araliphatic radical; or acyl derived from an aliphatic or araliphatic carboxylic acid or from an aliphatic or araliphatic semiester of carbonic acid, or $R_7$ and $R_8$, together with X and the nitrogen atom bonding $R_8$ and X, form an unsubstituted or substituted mono- or di-azacycloalkyl, azoxacycloalkyl, azathiacycloalkyl or optionally oxidized thiacycloalkyl radical bonded via a nitrogen atom, or an unsubstituted or substituted, optionally partially hydrogenated aryl or heteroaryl radical, $R_9$ is an aliphatic or araliphatic radical, or $R_7$, $R_8$ and $R_9$, together with X and the nitrogen atom bonding $R_8$, $R_9$ and X, form an unsubstituted or substituted quaternary heteroaryl radical bonded via the quaternary nitrogen atom, with A$^-$ being the anion of a protonic acid, alk is lower alkylene, and X (unless, together with $R_7$ and $R_8$ and the nitrogen atom bonding $R_8$ and X or together with the nitrogen atom bonding $R_8$, $R_9$ and X, it forms part of one of the mentioned ring systems) is a divalent aliphatic, cycloaliphatic or araliphatic radical or a direct bond, with the proviso that in compounds of formula I wherein $R_1$ is a group of formula Ic, $R_2$ and $R_3$ are each independently of the other fluorine, chlorine, bromine, methyl, ethyl or trifluoromethyl and $R_4$ is hydrogen, when alk is methylene, ethylidene or propylidene, the group —N($R_8$)—X—$R_7$ is other than a 5-membered mono-, di-, tri- or tetra-azaheteroaryl radical that is bonded via a nitrogen atom and is optionally benzo-fused and/or substituted by alkyl having up to and including 6 carbon atoms or substituted in the ω-position by a group of the formula —N($R_a$)—$R_b$ wherein $R_a$ and $R_b$ are each independently of the other hydrogen, alkyl, cycloalkyl, phenyl-lower alkyl or pyridyl-lower alkyl or together with the nitrogen atom bonding them form a pyrrolidino, piperidino, piperazino, N'-lower alkylpiperazino, morpholino or azepino group, and the pharmaceutically acceptable salts thereof in the preparation of a medicament for the treatment of pathological conditions that are responsive to blocking of AMPA, kainate and/or glycine binding sites of the NMDA receptor, and also to compounds of formula I, with the proviso that in compounds of formula I wherein $R_1$, $R_3$ and $R_4$ are hydrogen and $R_2$ is a group of formula Ib, when alk is methylene, $R_6$ is other than amino or $R_7$ is other than carboxy, with the further proviso that in compounds of formula I wherein $R_1$, $R_3$ and $R_4$ are hydrogen and $R_2$ is a group of formula Ic, when alk is methylene, the group —N($R_8$)—X—$R_7$ is other than 1-imidazolyl or when alk is ethylene the group —N($R_8$)—X—$R_7$ is other than amino, dipropylamino, N-(2-phenylethyl)-N-propyl-amino and N'-(2-chlorophenyl)piperazino, and with the final proviso that in compounds of formula I wherein $R_1$ is a group of formula Ic, $R_2$ and $R_3$ are each independently of, the other fluorine, chlorine, bromine, methyl, ethyl or trifluoromethyl and $R_4$ is hydrogen, when alk is methylene, ethylidene or propylidene the group —N($R_8$)—X—$R_7$ is other than a 5-membered mono-, di-, tri- or tetra-azaheteroaryl radical that is bonded via a nitrogen atom and is optionally benzo-fused and/or substituted by alkyl having up to and including 6 carbon atoms or substituted in the ω-position by a group of the formula —N($R_a$)—$R_b$ wherein $R_a$ and $R_b$ are each independently of the other hydrogen, alkyl, cycloalkyl, phenyl-lower alkyl or pyridyl-lower alkyl or together with the nitrogen atom bonding them form a pyrrolidino, piperidino, piperazino, N'-lower alkylpiperazino, morpholino or azepino group, as such and salts thereof, to processes for the preparation thereof and to pharmaceutical compositions comprising them.

Unsubstituted or lower alkylated and/or lower alkanoylated amino is, for example, amino, lower alkylamino, lower alkanoylamino, N-lower alkyl-N-lower alkanoyl-amino or di-lower alkylamino.

Aliphatic radicals are, for example, lower alkyl, amino-lower alkyl, lower alkylamino-lower alkyl, di-lower alkylamino-lower alkyl, lower alkanoylamino-lower alkyl, hydroxy-lower alkyl, lower alkanoyloxy-lower alkyl, polyhalo-lower alkyl, lower alkoxy-lower alkyl, hydroxy-lower alkoxy-lower alkyl, lower alkoxy-lower alkoxy-lower alkyl or polyhalo-lower alkoxy-lower alkyl.

Cycloaliphatic radicals are, for example, 3- to 8-membered, especially 3- to 7-membered, cycloalkyl radicals that are unsubstituted or substituted by free or aliphatically esterified carboxy and/or by unsubstituted or lower alkylated and/or lower alkanoylated amino, such as corresponding cycloalkyl, carboxycycloalkyl, lower alkoxycarbonylcycloalkyl, aminocycloalkyl or mono- or di-lower alkylaminocycloalkyl, namely cyclopropyl, cyclobutyl, cyclopentyl, cyclohexyl, cycloheptyl, cyclooctyl, 2-aminocyclohexyl, 4-carboxycyclohexyl, 3-carboxycyclohexyl or 2-carboxycyclopentyl.

Heterocycloaliphatic radicals are, for example, mono- or di-azacycloalkyl, azoxacycloalkyl or azathiacycloalkyl radicals having from 3 up to and including 8, especially from 3 to 6, ring members that are unsubstituted or substituted by oxo, hydroxy and/or by free or aliphatically esterified carboxy, such as corresponding pyrrolidin-1-yl (pyrrolidino), pyrrolidin-2-yl, piperidin-1-yl (piperidino), piperidin-2-yl, morpholino, thiomorpholino or unsubstituted or lower alkylated or lower alkanoylated piperazino, for example pyrrolidino, oxopyrrolidinyl, piperidino, carboxypiperidino, lower alkoxycarbonylpiperidino, morpholino or thiomorpholino, especially morpholino, 5-oxopyrrolidin-2-yl or 2-carboxypyrrolidino.

Acyl derived from carbonic acid or from a semiester or semiamide of carbonic acid is derived, for example, from an aliphatic or araliphatic semiester or from an unsubstituted or aliphatically, araliphatically or aromatically substituted amide of carbonic acid and is, for example, free or aliphatically or araliphatically esterified carboxy, such as lower alkoxycarbonyl, or phenyl-lower alkoxycarbonyl that is unsubstituted or substituted by lower alkyl, lower alkoxy, hydroxy, halogen and/or by trifluoromethyl, or unsubstituted or aliphatically, araliphatically or aromatically substituted carbamoyl, such as carbamoyl, lower alkylcarbamoyl, di-lower alkylcarbamoyl, lower alkoxycarbonyl-lower alkylcarbamoyl, carboxy-lower alkylcarbamoyl, carbamoyl-lower alkylcarbamoyl, N-carbamoyl-lower alkyl-N-lower alkyl-carbamoyl, or phenylcarbamoyl or phenyl-lower alkylcarbamoyl that is unsubstituted or substituted by lower alkyl, lower alkoxy, polyhalo-lower alkoxy, hydroxy, halogen, nitro, carboxy, lower alkoxycarbonyl, phenyl, phenyloxy and/or by trifluoromethyl.

Acyl derived from sulfuric acid or from an aliphatic or aromatic sulfonic acid is, for example, sulfo, lower alkanesulfonyl, or benzylsulfonyl that is unsubstituted or substituted by lower alkyl, lower alkoxy, halogen, trifluoromethyl, carboxy and/or by lower alkoxycarbonyl, or naphthalenesulfonyl that is unsubstituted or substituted by di-lower alkylamino.

Acyl derived from phosphoric acid or from a phosphonic acid ester is, for example, phosphono or tri-lower alkylphosphono.

Amino that is unsubstituted or aliphatically or araliphatically substituted and/or substituted by aliphatic, araliphatic or aromatic acyl is, for example, amino, lower alkylamino, di-lower alkylamino, lower alkanoylamino, or phenyl-lower alkyl-, benzoyl- or naphthoyl-amino that is unsubstituted or substituted by lower alkyl, lower alkoxy, halogen and/or by trifluoromethyl, or ureido or amidino.

Unsubstituted or substituted aromatic radicals are, for example, phenyl or naphthyl that is unsubstituted or substituted by lower alkyl, lower alkoxy, lower alkylenedioxy, lower alkylidenedioxy, hydroxy, lower alkoxycarbonyl, carboxy, carbamoyl, sulfamoyl, lower alkoxycarbonylamino, lower alkanoyl, halogen and/or by trifluoromethyl.

Unsubstituted or substituted heteroaromatic radicals are optionally partially hydrogenated, 5- or 6-membered monocyclic heteroaryl or bicyclic heteroaryl composed of 5- or 6-membered rings, such as corresponding furyl, lower alkylfuryl, for example 4-methylfur-2-yl, thienyl, imidazolyl, for example imidazol-4-yl, oxazolyl, carboxy-lower alkyl(oxo)oxazolyl, for example 2,5-dihydro-3-oxo-1,2-oxazolyl, thiazolyl, dihydrothiazolyl, for example 4,5-dihydrothiazolyl, carboxy-lower alkylthiazolyl, for example 4-carboxymethylthiazolyl, lower alkoxycarbonyl-lower alkylthiazolyl, for example 4-methoxycarbonylmethylthiazolyl or 4-ethoxycarbonylmethylthiazolyl, tetrazolyl, pyridyl, pyrazinyl, indolyl, for example indol-3-yl, quinolinyl, for example quinolin-4-yl, benzazepinyl or carboxy-lower alkyl-2,3,4,5-tetrahydro-1H-1-benzazepino, for example 1-carboxymethyl-2,3,4,5-tetrahydro-1H-1-benzazepino.

Araliphatic radicals are, for example, phenyl-lower alkyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl.

Acyl derived from an aliphatic or araliphatic carboxylic acid is, for example, lower alkanoyl, lower alkenoyl, or phenyl-lower alkanoyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl.

Acyl derived from an aliphatic or araliphatic semiester of carbonic acid is, for example, lower alkoxycarbonyl, or phenyl-lower alkoxycarbonyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl.

Unsubstituted or substituted mono- or di-azacycloalkyl, azoxacycloalkyl, azathiacycloalkyl or optionally oxidized thiacycloalkyl radicals formed by $R_7$ and $R_8$ together with X and the nitrogen atom bonding $R_8$ and X and bonded via a nitrogen atom are, for example, 3- to 7-membered, especially 5- to 7-membered, monocyclic mono- or di-azacycloalkyl, azoxacycloalkyl, azathiacycloalkyl or optionally oxidized thiacycloalkyl radicals or bicyclic azacycloalkyl radicals composed of 5- and/or 6-membered rings, preferably pyrrolidino, imidazolidino, tetrahydrothiazolyl, piperidino, morpholino, thiomorpholino, piperazino, homopiperidino or 1-azabicyclononyl that are unsubstituted or substituted by aliphatic, araliphatic or aromatic radicals, such as lower alkyl, hydroxy-lower alkyl, unsubstituted or substituted phenyl-lower alkyl or phenyl radicals, free, esterified or amidated carboxy, such as carboxy, lower alkoxycarbonyl, unsubstituted or substituted phenylcarbamoyl, unsubstituted or lower alkylated and/or lower alkanoylated amino, such as di-lower alkylamino or lower alkanoylamino, 2-oxoimidazolidino, free or esterified phosphono, such as phosphono or tri-lower alkylphosphono, tetrazolyl, acyl derived from an aliphatic or aromatic carboxylic acid, such as lower alkanoyl or unsubstituted or substituted benzoyl, for example fluorobenzoyl, hydroxy, oxo and/or by lower alkoxy, such as pyrrolidino, lower alkylpyrrolidino, carboxypyrrolidino, for example 2-carboxypyrrolidino, lower alkoxycarbonylpyrrolidino, hydroxypyrrolidino, for example 3-hydroxypyrrolidino, hydroxy-lower alkylpyrrolidino, for example 2-hydroxymethylpyrrolidino, mono- or dioxopyrrolidino, for example 2-oxopyrrolidino or 2,5-dioxopyrrolidino, lower alkyl(oxo)pyrrolidino, for example 2-methyl-5-oxo-pyrrolidino, hydroxy-lower alkyl (oxo)pyrrolidino, for example 2-hydroxymethyl-5-oxo-pyrrolidino, carboxy(oxo)pyrrolidino, for example 5-carboxy-2-oxopyrrolidino, 2-carboxy-4-hydroxy-pyrrolidino or 2-carboxy-3-hydroxy-pyrrolidino, lower alkoxycarbonyl(oxo)pyrrolidino, 2-oxoimidazolidino, for example 2-oxo-3-phenyl-imidazolidino, tetrahydrothiazolyl, for example tetrahydrothiazol-1-yl, piperidino, lower alkylpiperidino, for example 4-methylpiperidino, 3-methylpiperidino or 4-butylpiperidino, di-lower alkylpiperidino, for example 2,6-dimethylpiperidino, carboxypiperidino, for example 4-carboxypiperidino, 2-carboxypiperidino or 3-carboxypiperidino, lower alkoxycarbonylpiperidino, for example 4-ethoxycarbonylpiperidino or 2-ethoxycarbonylpiperidino, phenylcarbamoylpiperidino, for example 3-phenylcarbamoylpiperidino, 2-phenylcarbamoylpiperidino or 4-phenylcarbamoylpiperidino, oxopiperidino, for example 4-oxopiperidino, dioxopiperidino, for example 3,6-oxo(phenyl-lower alkyl)piperidino, for example 2-benzyl-4oxopiperidino, dioxopiperidino, oxo(phenyl)piperidino, for example 2-oxo-3-phenyl-piperidino or 2-oxo-5-phenyl-piperidino, hydroxypiperidino, for example 4-hydroxypiperidino or 3-hydroxypiperidino, hydroxy(phenyl-lower alkyl)piperidino, for example 2-benzyl-4-hydroxy-piperidino, carboxy(hydroxy)piperidino, for example 2-carboxy-4-hydroxypiperidino, di-lower alkylaminopiperidino, for example 4-dimethylaminopiperidino, lower alkanoylaminopiperidino, for example 4-acetylaminopiperidino, lower alkanoylamino(phenyl-lower alkyl)piperidino, for example 4-acetylamino-2-benzyl-piperidino, lower alkanoylamino(phenyl)piperidino, for example 4-acetylamino-2-phenyl-piperidino, phenylpiperidino, for example 4-phenylpiperidino, lower alkoxypiperidino, for example 4-methoxypiperidino, lower alkoxy(lower alkyl)piperidino, for example 4-methoxy-4-methyl-piperidino, di-lower alkoxypiperidino, for example 4,4-dimethoxypiperidino, di-lower alkoxy(lower alkyl)-piperidino, for example 2-benzyl-4,4-dimethoxypiperidino, lower alkylenedioxypiperidino, for example 4-ethylenedioxypiperidino, hydroxy-lower alkylpiperidino, for example 2-(2-hydroxyethyl)piperidino, 2-hydroxymethylpiperidino, 4-(1-hydroxyethyl)piperidino, 4-hydroxymethylpiperidino, unsubstituted or halogenated benzoylpiperidino, for example 4-(4-fluorobenzoyl)piperidino, lower alkanoylpiperidino, for example 4-acetylpiperidino, or oxoimidazolidinopiperidino, for example 4-(2-oxoimidazolidino)piperidino, homopiperidino, oxohomopiperidino, for example 2-oxohomopiperidino, azabicyclononyl, for example 1-azabicyclononyl, piperazino, lower alkylpiperazino, for example 4-methylpiperazino, oxopiperazino, for example 3-oxopiperazino, dioxopiperazino, for example 3,5-dioxopiperazino, unsubstituted or lower alkoxylated phenylpiperazino, for example 4-(4-methoxyphenyl)piperazino, morpholino, di-lower alkylmorpholino, for example 3,5-dimethylmorpholino, or thiomorpholino.

Unsubstituted or substituted, optionally partially hydrogenated aryl radicals formed by $R_7$ and $R_8$ together with X and the nitrogen atom bonding $R_8$ and X are, for example, phenyl, cyclohexadienyl, naphthyl or tetrahydronaphthyl radicals that are unsubstituted or substituted by lower alkyl, lower alkoxy, hydroxy, halogen, carboxy, lower alkoxycarbonyl and/or by trifluoromethyl, such as phenyl, 4-hydroxyphenyl, 3-methoxyphenyl, 3-carboxyphenyl, 4-fluorophenyl, 2-fluorophenyl, 3-fluorophenyl, 3,5-bistrifluoromethylphenyl, cyclohexa-1,3-dien-5-yl or 1,2,3,4-tetrahydronaphthyl.

Unsubstituted or substituted, optionally partially hydrogenated heteroaryl radicals formed by $R_7$ and $R_8$ together with the nitrogen atom bonding $R_8$ and X are, for example, optionally partially hydrogenated pyrrolyl that is unsubstituted or substituted by carboxy, lower alkoxycarbonyl and/or by lower alkanoyl, such as pyrrol-1-yl, 1,5-dihydropyrrol-1-yl, carboxy-pyrrolyl, for example 2-carboxypyrrol-1-yl or 3-carboxypyrrol-1-yl, lower alkoxycarbonyl-pyrrolyl, for example 3-methoxycarbonylpyrrol-1-yl, 3-ethoxycarbonylpyrrol-1-yl or 3-butyloxycarbonylpyrrol-1-yl, lower alkanoylpyrrolyl, for example 3-acetylpyrrol-1-yl; furyl, for example fur-2-yl; thienyl, for example thien-2-yl or thien-3-yl; imidazolyl that is unsubstituted or substituted by lower alkyl, hydroxy-lower alkyl, carboxy, carboxy-lower alkyl and/or by lower alkoxycarbonylamino-lower alkyl, such as imidazol-1-yl, lower alkylimidazolyl, for example 4-methylimidazol-1-yl, 2-methylimidazol-1-yl or 2-ethylimidazol-1-yl, di-lower alkylimidazolyl, for example 2-ethyl-4-methyl-imidazol-1-yl, hydroxy-lower alkylimidazolyl, for example 4-hydroxymethylimidazol-1-yl, carboxy-lower alkylimidazolyl, for example carboxy-methylimidazol-1-yl, carboxy(lower alkoxycarbonylamino-lower alkyl)imidazolyl, for example 4-(3-tert-butyloxycarbonylaminoprop-1-yl)-2-(2-carboxyethyl)-imidazol-1-yl; optionally partially hydrogenated thiazolyl that is unsubstituted or substituted by carboxy-lower alkyl and/or by lower alkoxycarbonyl-lower alkyl, such as thiazol-2-yl, 3,4-dihydrothiazol-2-yl, carboxy-lower alkylthiazolyl, for example 4-carboxymethylthiazol-2-yl, lower alkoxycarbonyl-lower alkylthiazolyl, for example 4-ethoxycarbonylethylthiazol-2-yl; unsubstituted or lower alkyl-substituted pyrazolyl, such as pyrazol-1-yl or di-lower alkylpyrazolyl, for example 3,5-dimethylpyrazol-1-yl; triazolyl, such as 1,2,4-triazol-1-yl; unsubstituted or oxo-substituted, optionally partially hydrogenated pyridinyl, such as pyridinyl, for example pyridin-2-yl, 1,2,5,6-tetrahydropyridin-1-yl, oxodihydropyridinyl, for example 2-oxo-1,2-dihydro-pyridin-1-yl, oxo-tetrahydropyridinyl, for example 2-oxo-1,2,3,4-tetrahydro-pyrimidin-1-yl; pyrazinyl, for example pyrazin-2-yl; indolyl that is unsubstituted or substituted by carboxy, carboxy-lower alkyl, lower alkoxycarbonyl, lower alkoxycarbonyl-lower alkyl, cyano-lower alkyl and/or by nitro, such as indol-2-yl, carboxyindolyl, for example 2-carboxyindol-1-yl or 3-carboxyindol-1-yl, carboxy-lower alkylindolyl, for example 3-carboxymethylindol-1-yl, lower alkoxycarbonylindolyl, for example 3-methoxycarbonylindol-1-yl or 2-butyloxycarbonylindol-1-yl, lower alkoxycarbonyl-lower alkylindolyl, for example 3-ethoxycarbonylmethylindol-1-yl, cyano-lower alkylindolyl, for example 3-cyanomethylindol-1-yl, nitroindolyl, for example 5-nitroindol-1-yl; benzofuranyl, for example benzofuran-2-yl; unsubstituted or nitro-substituted benzimidazolyl, such as benzimidazolyl, 5-nitrobenzimidazol-1-yl or 6-nitrobenzimidazol-1yl; tetrahydroquinolinyl, such as 1,2,3,4-tetrahydroquinolin-1-yl; unsubstituted or oxo-substituted tetrahydroisoquinolinyl, such as 1,2,3,4-tetrahydroisoquinolin-1-yl or 2-oxo-1,2,3,4-tetrahydroisoquinolin-1-yl, or tetrahydrobenzazepinyl, such as 2,3,4,5-tetrahydro-1H-1-benzazepin-1-yl.

Divalent aliphatic radicals X are, for example, lower alkylene, lower alkenylene and lower alkylidene radicals that are unsubstituted or substituted by oxo, hydroxy and/or by amino, such as lower alkylene, lower alkylidene, lower alkenylene, oxo-lower alkylene including carbonyl, oxo-lower alkylidene, dioxo-lower alkylene, oxo-lower alkenylene, hydroxy-lower alkylidene, oxo(hydroxy)-lower alkylene, amino-lower alkylene, amino-lower alkylidene, carboxy-lower alkylene, carboxy-lower alkylidene, carbamoyl-lower alkylidene, lower alkoxy-carbonyl-lower alkylidene, lower alkoxycarbonyl-lower alkylene or ω-aza-α-oxo-lower alkylene or ω-aza-α-oxo-lower alkenylene.

Divalent cycloaliphatic radicals X are, for example, 3- to 7-membered, especially 3- to 5-membered, cycloalkylidene radicals, such as cyclopropylidene, cyclobutylidene or cyclopentylidene.

Divalent araliphatic radicals X are, for example, unsubstituted or lower alkyl-, lower alkoxy-, lower alkylenedioxy-, lower alkylidenedioxy-, hydroxy-, lower alkoxycarbonyl-, carboxy-, carbamoyl-, lower alkanoyl-, halo- and/or trifluoromethyl-substituted phenyl-lower alkylidene or phenyl-lower alkylene.

Hereinbefore and hereinafter "lower" radicals and compounds are to be understood as being, for example, those containing up to and including 7, especially up to and including 4, carbon atoms.

Amino-lower alkyl is, for example, amino-$C_1$–$C_4$alkyl, such as aminomethyl, 2-aminoethyl, 3-aminopropyl or 4-aminobutyl.

Amino-lower alkylene is, for example, amino-$C_1$–$C_4$alkylene, such as aminomethylene, 2-aminoethylene, 3-aminopropylene or 4-aminobutylene.

Amino-lower alkylidene is, for example, amino-$C_1$–$C_7$alkylidene, such as aminomethylene, 2-aminoethylidene, 3-aminopropylidene or 4-aminobutylidene.

Carbamoyl-lower alkylcarbamoyl is, for example, carbamoyl-$C_1$–$C_4$alkylcarbamoyl, such as carbamoylmethylcarbamoyl, 2-carbamoylethylcarbamoyl, 3-carbamoylpropylcarbamoyl or 4-carbamoylbutylcarbamoyl.

Carbamoyl-lower alkylidene is, for example, carbamoyl-$C_1$–$C_7$alkylidene, such as carbamoylmethylene, 2-carbamoylethylidene, 3-carbamoylpropylidene, 4-carbamoylbutylidene, 5-carbamoylpentylidene or 6-carbamoylhexylidene.

N-Carbamoyl-lower alkyl-N-lower alkyl-carbamoyl is, for example, N-carbamoyl-$C_1$–$C_4$alkyl-N—$C_1$–$C_4$alkyl-carbamoyl, such as especially N-carboxymethyl-N-methyl-carbamoyl.

Carboxy-lower alkyl is, for example, carboxy-$C_1$–$C_4$alkyl, such as carboxymethyl, 1- or 2-carboxyethyl, 3-carboxypropyl or 4-carboxybutyl.

Carboxy-lower alkylcarbamoyl is, for example, carboxy-$C_1$–$C_4$alkylcarbamoyl, such as carboxymethylcarbamoyl, 2-carboxyethylcarbamoyl, 3-carboxypropylcarbamoyl or 4-carboxybutylcarbamoyl.

Carboxy-lower alkylene is, for example, carboxymethylene, 1- or 2-carboxyethylene, 1,3-(1-carboxy)propylene, 1,3-(3-carboxy)propylene or 1,4-(4-carboxy)butylene.

Carboxy-lower alkylidene is, for example, carboxy-$C_1$–$C_7$alkylidene, such as carboxymethylene, 2-carboxyethylidene, 3-carboxypropylidene, 4-carboxybutylidene, 5-carboxypentylidene or 6-carboxyhexylidene.

Cyano-lower alkyl is, for example, cyano-$C_1$–$C_4$alkyl, such as cyanomethyl, 1- or 2-cyanoethyl, 3-cyanopropyl or 4-cyanobutyl.

Di-lower alkylaminocycloalkyl is, for example, di-$C_1$–$C_4$alkylaminocycloalkyl, such as dimethylaminocycloalkyl, diethylaminocycloalkyl, N-ethyl-N-methyl-aminocycloalkyl, N-propyl-N-methyl-aminocycloalkyl, N-isopropyl-N-methyl-aminocycloalkyl or N-butyl-N-methyl-aminocycloalkyl, wherein cycloalkyl is, for example, cyclopropyl, cyclobutyl, cyclopentyl or cyclohexyl.

Di-lower alkylamino is, for example, di-$C_1$–$C_4$alkylamino, such as dimethylamino, diethylamino, N-ethyl-N-methyl-amino, N-propyl-N-methyl-amino, N-isopropyl-N-methyl-amino or N-butyl-N-methyl-amino.

Di-lower alkylamino-lower alkyl is, for example, di-$C_1$–$C_4$alkylamino-$C_1$–$C_4$alkyl, such as dimethylaminomethyl, diethylaminomethyl, N-ethyl-N-methyl-aminomethyl, N-propyl-N-methyl-aminomethyl, N-isopropyl-N-methyl-aminomethyl or N-butyl-N-methyl-aminomethyl.

Di-lower alkylcarbamoyl is, for example, di-$C_1$–$C_4$alkylcarbamoyl, such as dimethylcarbamoyl, diethylaminomethyl, N-ethyl-N-methyl-carbamoyl, N-propyl-N-methyl-carbamoyl, N-isopropyl-N-methyl-carbamoyl or N-butyl-N-methyl-carbamoyl.

Dioxo-lower alkylene is, for example, dioxo-$C_2$–$C_4$alkylene, such as 1,2-dioxoethylene (oxalo), 1,3-(1,2-dioxo)propylene, 1,3-(2,3-dioxo)propylene or 1,4-(1,2-dioxo)propylene.

Halogen is, for example, halogen having an atomic number of up to and including 35, such as chlorine, fluorine or bromine.

Hydroxy-lower alkoxy-lower alkyl is, for example, hydroxy-$C_1$–$C_4$alkoxy-$C_1$–$C_4$alkyl, such as 2-hydroxyethoxymethyl, 2-hydroxymethoxyethyl, 2-(2-hydroxyethoxy)ethyl or 3-hydroxymethoxypropyl.

Hydroxy-lower alkyl is, for example, hydroxy-$C_1$–$C_4$alkyl, such as hydroxymethyl, 2-hydroxyethyl, 3-hydroxypropyl or 4-hydroxybutyl.

Hydroxy-lower alkylidene is, for example, hydroxy-$C_1$–$C_4$alkylidene, such as hydroxymethylene, 2-hydroxypropylidene, 2-hydroxyethylidene, 3-hydroxypropylidene or 4-hydroxybutylidene.

N-Lower alkyl-N-lower alkanoyl-amino is, for example, N-$C_1$–$C_7$alkanoyl-N-$C_1$–$C_4$alkyl-amino, such as N-acetyl-N-methyl-amino, N-propionyl-N-methyl-amino, N-butyryl-N-methyl-amino, N-isobutyryl-N-methyl-amino or N-pivaloyl-N-methyl-amino.

Lower alkylidenedioxy is, for example, $C_1$–$C_4$alkylidenedioxy, such as methylenedioxy, ethylidenedioxy or isopropylidenedioxy; lower alkylenedioxy, for example $C_1$–$C_4$alkylenedioxy, such as ethylenedioxy or 1,3-propylenedioxy.

Lower alkanoyl is, for example, $C_1$–$C_7$alkanoyl, such as acetyl, propionyl, butyryl, isobutyryl or pivaloyl.

Lower alkanoylamino is, for example, $C_1$–$C_7$alkanoylamino, such as acetylamino, propionylamino, butyrylamino, isobutyrylamino or pivaloylamino.

Lower alkanoylamino-lower alkyl is, for example, $C_1$–$C_7$alkanoylamino-$C_1$–$C_4$alkyl, such as acetylaminomethyl, propionylaminomethyl, butyrylaminomethyl or isobutyrylaminomethyl, and also pivaloylaminomethyl.

Lower alkanoyloxy-lower alkyl is, for example, $C_1$–$C_7$alkanoyloxy-$C_1$–$C_4$alkyl, such as acetoxymethyl, propionyloxymethyl, butyryloxymethyl or isobutyryloxymethyl, and also pivaloyloxymethyl.

Lower alkenoyl is, for example, $C_3$–$C_7$alkenoyl, such as acryloyl, methacryloyl, crotonyl or vinylacetyl.

Lower alkenylene is, for example, $C_2$–$C_7$alkenylene, such as vinylene, 1,3-prop-2-enylene, 1,2-prop-2-enylene, 1,4-but-2-enylene, 1,2-but-3-enylene, 1,2-pent-4-enylene, 1,2-hex-4-enylene or 1,2-hex-5-enylene.

Lower alkoxy is, for example, $C_1$–$C_7$alkoxy, preferably $C_1$–$C_4$alkoxy, such as methoxy, ethoxy, propyloxy, isopropyloxy or butyloxy, but may also be isobutyloxy, sec-butyloxy, tertbutyloxy or a pentyloxy, hexyloxy or heptyloxy group.

Lower alkoxycarbonyl is, for example, $C_1$–$C_7$alkoxycarbonyl, preferably $C_1$–$C_4$alkoxycarbonyl, such as methoxycarbonyl, ethoxycarbonyl, propyloxycarbonyl, isopropyloxycarbonyl or butyloxycarbonyl, but may also be isobutyloxycarbonyl, sec-butyloxycarbonyl, tert-butyloxycarbonyl or a pentyloxycarbonyl, hexyloxycarbonyl or heptyloxycarbonyl group.

Lower alkoxycarbonylamino is, for example, $C_1$–$C_7$alkoxycarbonylamino, preferably $C_1$–$C_4$alkoxycarbonylamino, such as methoxycarbonylamino, ethoxycarbonylamino, propyloxycarbonylamino, isopropyloxycarbonylamino or butyloxycarbonylamino.

Lower alkoxycarbonylamino-lower alkyl is, for example, $C_1$–$C_7$alkoxycarbonylamino-$C_1$–$C_4$-alkyl, preferably $C_1$–$C_4$alkoxycarbonylamino-$C_1$–$C_4$alkyl, such as methoxycarbonylaminomethyl, ethoxycarbonylaminomethyl, propyloxycarbonylaminomethyl, isopropyloxycarbonylaminomethyl or butyloxycarbonylaminomethyl.

Lower alkoxycarbonyl-lower alkylcarbamoyl is, for example, $C_1$–$C_7$alkoxycarbonyl-$C_1$–$C_4$alkylcarbamoyl, preferably $C_1$–$C_4$alkoxycarbonyl-$C_1$–$C_4$alkylcarbamoyl, such as methoxycarbonylmethylcarbamoyl, ethoxycarbonylmethylcarbamoyl, propyloxycarbonylmethylcarbamoyl, isopropyloxycarbonylmethylcarbamoyl or butyloxycarbonylmethylcarbamoyl.

Lower alkoxycarbonylcycloalkyl is, for example, $C_1$–$C_7$alkoxycarbonylcycloalkyl, preferably $C_1$–$C_4$alkoxycarbonylcycloalkyl, such as methoxycarbonylcycloalkyl, ethoxycarbonylcarbamoylcycloalkyl, propyloxycarbonylcycloalkyl, isopropyloxycarbonylcycloalkyl or butyloxycarbonylcycloalkyl, wherein cycloalkyl is, for example, cyclopropyl, cyclobutyl, cyclopentyl or cyclohexyl.

Lower alkoxycarbonyl-lower alkyl is, for example, $C_1$–$C_7$alkoxycarbonyl-$C_1$–$C_4$alkyl, preferably $C_1$–$C_4$alkoxycarbonyl-$C_1$–$C_4$alkyl, such as methoxycarbonylmethyl, methoxycarbonylethyl, ethoxycarbonylmethyl, ethoxycarbonylethyl, methoxycarbonylpropyl, ethoxycarbonylpropyl, propyloxycarbonylmethyl, propyloxycarbonylethyl, isopropyloxycarbonylmethyl, isopropyloxycarbonylethyl or butyloxycarbonylmethyl.

Lower alkoxycarbonyl-lower alkylene is, for example, $C_1$–$C_7$alkoxycarbonyl-$C_2$–$C_4$alkylene, preferably $C_1$–$C_4$alkoxycarbonyl-$C_2$–$C_4$alkylene, such as 1-methoxycarbonylethylene, 1-ethoxycarbonylethylene, 1,3-(methoxycarbonyl)propylene, 1,3-(ethoxycarbonyl)propylene, 1,3-(propyloxycarbonyl)propylene, 1,3-(butyloxycarbonyl)propylene, 1,3-(sec-butyloxycarbonyl)propylene or 1,3-(tert-butyloxycarbonyl)propylene.

Lower alkoxycarbonyl-lower alkylidene is, for example, $C_1$–$C_4$alkoxycarbonyl-$C_1$–$C_7$-alkylidene, such as methoxycarbonylmethylene, ethoxycarbonylmethylene, 2-methoxycarbonylethylidene, 2-ethoxycarbonylethylidene, 3-methoxycarbonylpropylidene, 3-ethoxycarbonylpropylidene, 4-methoxycarbonylbutylidene, 4-ethoxycarbonylbutylidene, 5-methoxycarbonylpentylidene, 5-ethoxycarbonylpentylidene, 6-methoxycarbonylhexylidene or 6ethoxycarbonylhexylidene.

Lower alkoxy-lower alkoxy-lower alkyl is, for example, $C_1$–$C_4$alkoxy-$C_1$–$C_4$alkoxy-$C_1$–$C_4$alkyl, such as 2-methoxyethoxymethyl, 2-ethoxyethoxymethyl, 2-(2-methoxyethoxy)ethyl or 2-(2-ethoxyethoxy)ethyl.

Lower alkoxy-lower alkyl is, for example, $C_1$–$C_4$alkoxy-$C_1$–$C_4$alkyl, such as 2-methoxyethyl, ethoxymethyl, 2-methoxyethyl , 2-ethoxyethyl, 3-methoxypropyl or 4-methoxybutyl.

Lower alkylaminocycloalkyl is, for example, $C_1$–$C_4$alkylaminocycloalkyl, such as methylaminocycloalkyl, ethylaminocycloalkyl, propylaminocycloalkyl, isopropylaminocycloalkyl or butylaminocycloalkyl, wherein cycloalkyl is, for example, cyclopropyl, cyclobutyl, cyclopentyl or cyclohexyl.

Lower alkyl is, for example, $C_1$–$C_7$alkyl, preferably $C_1$–$C_4$alkyl, such as especially methyl or secondly ethyl, propyl, isopropyl or butyl, but may also be isobutyl, sec-butyl, tert-butyl or a $C_5$–$C_7$alkyl group, such as a pentyl, hexyl or heptyl group.

Lower alkylamino is, for example, $C_1$–$C_4$alkylamino, such as methylamino, ethylamino, propylamino, isopropylamino or butylamino.

Lower alkylamino-lower alkyl is, for example, $C_1$–$C_4$alkylamino-$C_1$–$C_4$alkyl, such as methylaminomethyl, ethylaminomethyl, 2-methylaminoethyl, 2-ethylaminoethyl, propylaminomethyl, isopropylaminomethyl or butylaminomethyl.

Lower alkylaminocarbamoyl is, for example, $C_1$–$C_4$alkylaminocarbamoyl, such as methylaminocarbamoyl, ethylaminocarbamoyl, propylaminocarbamoyl, isopropylaminocarbamoyl or butylaminocarbamoyl.

Lower alkylene may be straight-chained or branched and bonded in any position and is, for example, straight-chained or branched $C_1$–$C_4$alkylene, such as especially methylene, and also 1,2-ethylene, 1,3- or 1,2-propylene or 1,4-, 1,3- or 2,3-butylene.

Lower alkylidene may be straight-chained or branched and geminally bonded in any position and is, for example, straight-chained or branched $C_1$–$C_4$alkylidene, such as especially methylene, 1,1-ethylidene, 1,1- or 2,2-propylidene or 1,1-butylidene.

N-Lower alkyl-N-lower alkanoyl-amino is, for example, N-$C_1$–$C_7$alkanoyl-N-$C_1$–$C_4$alkyl-amino, such as N-acetyl-N-methyl-amino, N-propionyl-N-methyl-amino, N-butyryl-N-methyl-amino, N-isobutyryl-N-methyl-amino or N-pivaloyl-N-methyl-amino.

Lower alkanesulfonyl is, for example, $C_1$–$C_4$alkanesulfonyl, such as methanesulfonyl, ethanesulfonyl or propanesulfonyl.

Oxo(hydroxy)-lower alkylene is, for example, oxo (hydroxy)-$C_2$–$C_4$alkylene, such as 1-oxo-2hydroxyethylene, 1,3-(1-oxo-2-hydroxy)propylene, 1,3-(1-oxo-3-hydroxy)propylene, 1,3-(2-oxo-3-hydroxy)propylene or 1,4-(1-oxo-2-hydroxy)butylene.

Oxo-lower alkylene, including carbonyl, is bonded to the group —N($R_8$)— or the oxy or thio group preferably via the carbon atom carrying the oxo group and is, for example, corresponding oxo-$C_1$–$C_4$alkylene, such as carbonyl or 1,2-(1-oxo)ethylene, and also 1,3-(1-oxo)-propylene or 1,4-(1-oxo)butylene.

Phenyl-lower alkoxycarbonyl is, for example, phenyl-$C_1$–$C_4$alkoxycarbonyl, such as benzyloxycarbonyl or 1-phenylethoxycarbonyl, that is unsubstituted or substituted by $C_1$–$C_4$alkyl, $C_1$–$C_4$alkoxy, hydroxy, halogen and/or by trifluoromethyl.

Phenyl-lower alkyl is, for example, phenyl-$C_1$–$C_4$alkyl, such as benzyl, 1- or 2-phenylethyl, 3-phenylpropyl or 4-phenylbutyl, that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl.

Phenyl-lower alkylamino is, for example, phenyl-$C_1$–$C_4$alkylamino, such as benzylamino, 1- or 2-phenylethylamino, 3-phenylpropylamino or 4-phenylbutylamino, that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl.

Phenyl-lower alkylene is, for example, phenyl-$C_2$–$C_4$alkylene, such as phenylethylene, 1- or 2-phenylpropylene or 1- or 2-phenylbutylene, that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl.

Phenyl-lower alkylidene is, for example, phenyl-$C_1$–$C_7$alkylidene, such as benzylidene, 2-phenylethylidene, 3-phenylpropylidene, 4-phenylbutylidene, 5-phenylpentylidene or 6phenylhexylidene.

Polyhalo-lower alkoxy-lower alkyl is, for example, trifluoromethoxy-$C_1$–$C_4$alkyl, such as trifluoromethoxymethyl, 2-trifluoromethoxyethyl, 3-trifluoromethoxypropyl or 4-trifluoromethoxybutyl.

Polyhalo-lower alkyl is, for example, trifluoromethyl.

Tri-lower alkylphosphono is, for example, tri-$C_1$–$C_7$alkylphosphono, preferably tri-$C_1$–$C_4$-alkylphosphono, such as especially trimethylphosphono, or secondly triethylphosphono, tripropylphosphono, triisopropylphosphono or tributylphosphono.

ω-Aza-α-oxo-lower alkenylene is, for example, 1,3-(3-aza-1-oxo)prop-2-enylene.

ω-Aza-α-oxo-lower alkylene is, for example, 1,3-(3-aza-1-oxo)propylene.

Compounds of formula I having acidic groups may form salts with bases. Compounds of formula I having basic groups may also form acid addition salts and, where in addition at least one acidic group is present, may also form internal salts.

Salts of compounds of formula I with bases are, for example, salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, and also ammonium salts with ammonia or organic amines or quaternary ammonium bases, such as optionally C-hydroxylated aliphatic amines, especially mono-, di- or tri-lower alkylamines, for example methyl-, ethyl- or diethyl-amine, mono-, di- or tri-(hydroxy-lower alkyl)amines, such as ethanolamine, diethanolamine or triethanolamine, tris(hydroxymethyl)methylamine or 2-hydroxy-tert-butylamine, or N-(hydroxy-lower alkyl)-N,N-di-lower alkyl-amines or N-(polyhydroxy-lower alkyl)-N-lower alkylamines, such as 2-(dimethylamino)ethanol or D-glucamine or choline, or quaternary aliphatic ammonium hydroxides, for example tetrabutylammonium hydroxide.

Acid addition salts of compounds of formula I are, for example, the pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, salts with suitable carboxylic acids, such as optionally hydroxylated lower alkanoic acids, for example acetic acid, glycolic acid, propionic acid, lactic acid or pivalic acid, optionally hydroxylated and/or oxo-substituted lower alkanedicarboxylic acids, for example oxalic acid, succinic acid, fumaric acid, maleic acid, tartaric acid, citric acid, pyruvic acid, malic acid, ascorbic acid, and also with aromatic, heteroaromatic or araliphatic carboxylic acids, such as benzoic acid, nicotinic acid or mandelic acid, and salts with suitable aliphatic or aromatic sulfonic acids or N-substituted sulfamic acids, for example methanesulfonates, benzenesulfonates, p-toluenesulfonates or N-cyclohexylsulfamates (cyclamates).

Also included are both total and partial salts, that is to say salts with 1, 2 or 3, preferably 2, equivalents of base per mole of acid of formula 1, or salts with 1, 2 or 3 equivalents, preferably 1 equivalent, of acid per mole of base of formula 1.

For the purposes of isolation or purification it is also possible to use pharmaceutically unacceptable salts. Only the pharmaceutically acceptable, non-toxic salts are used therapeutically and they are therefore preferred.

The compounds of formula I have valuable pharmacological properties. They exhibit a high degree of binding affinity for AMPA receptors, kainate receptors and/or glycine binding sites of NMDA receptors. The affinity for the mentioned receptors is global or selective according to the structure. Selected compounds of formula I exhibit especially a strong affinity for AMPA and/or kainate binding sites and a less strong affinity for glycine binding sites of the NMDA receptor.

The binding capacity of the compounds prepared according to the invention and their salts can be demonstrated in vitro radiographically in brain membranes of rats with reference to the displacement of [$^3$H]-AMPA, [$^3$H]-kainate or [$^3$H]-DCKA (5,7-dichlorokynurenic acid), the concentration required for 50% displacement ($IC_{50}$) being determined from the % displacement several concentrations.

In order to determine the binding affinity for AMPA receptors it is possible to use, for example, the radio receptor assay of Honore T., Lauridsen J. and Krogsgaard-Larsen according to J. Neurochem. 38, 173–178, in which compounds of formula I exhibit $IC_{50}$ values of approximately 0.05 to approximately 5 μM. For N-(2,3-dioxo-7-nitro-1,2,3,4-tetrahydroquinoxalin-5-ylmethyl)-2-amino-2-thiazoline hydrobromide, for example, an $IC_{50}$ value of 0.3 micromol/litre was determined. The binding affinity for kainate receptors can be measured, for example, by means of the radio receptor assay of Simon J. R., Contrera J. F. and Kuhn M. J., J. Neurochem 26, 141–147, in which compounds of formula I exhibit $IC_{50}$ values of from approximately 0.5 to approximately 5 μM.

The binding capacity of compounds of formula I to glycine binding sites of the NMDA receptor can be determined, for example, in the radio receptor assay according to Baron M. B, Siegel B. W. et al., Eur. J. Pharmacol., Molec. Pharmacol. Section 206, pages 149–154 (1991) and Canton T., Doble A. et al., J. Pharm. Pharmacol. 44, pages 812–816 (1992) on rat cortex and rat hippocampus membranes. In that experimental procedure the $IC_{50}$ of compounds of formula I lies in the range of from approximately 0.005 to approximately 5 μM. For N-(7-bromo-2,3-dioxo-1,2,3,4-tetrahydroquinoxalin-5-ylmethyl)-3-thienylacetamide, for example, an $IC_{50}$ value of 0.007 micromol/litre was determined.

By virtue of those properties, the compounds of formula I have pronounced anticonvulsive properties which are determined in vivo, for example in mice, by reference to their pronounced protective action with respect to convulsions triggered by electric shock or metrazole, it being possible to use, for example, the well established electric shock mouse model or the mouse model for metrazole-induced convulsions according to Schmutz et al., Naunyn-Schmiedeberg's Arch. Pharmacol. 342, 61–66 (1990).

The compounds of formula I and the pharmaceutically acceptable salts thereof are accordingly excellently suitable for the prophylactic and therapeutic treatment of pathological conditions that are responsive to blocking of one or more of the mentioned sub-types of excitatory amino acid receptors, for example neurodegenerative disorders, such as those arising from stroke, hypoglycemia, anoxia or symptoms of cerebral paralysis; ischemic brain disorders, such as cerebral ischemia, cerebral ischemia in cardiosurgery or cardiac arrest, perinatal asphyxia, epileptic fits, Huntington's chorea, Alzheimer's disease and Parkinson's disease, amyotrophic lateral sclerosis, spinal and cerebral trauma, and also symptoms of poisoning resulting from neurotoxins or drug abuse; and ischaemic disorders of the eyes; vascular and muscular spasms, such as migraine or local or general spasticity; convulsions, such as epilepsy; and anxiety states and pain, such as trigeminal neuralgias.

Structurally simpler compounds of formula I wherein the radical $R_1$ or $R_2$ that is other than $R_5$ is, for example, amino-lower alkyl or hydroxy-lower alkyl, can also be used as intermediates in the preparation of compounds of formula I having a side chain of more complex structure, by substituting the former in customary manner, for example by the use of customary nucleophilic substitution procedures, at the amino or hydroxy group.

The invention relates especially to compounds of formula I wherein one of the radicals $R_1$ and $R_2$ is a group $R_5$ and the other is a group of formula —CH($R_6$)—alk—$R_7$ (Ia), —alk—CH ($R_6$)—$R_7$ (Ib), —alk—N($R_8$)—X—$R_7$ (Ic), —alk—N$^+$ ($R_8$)($R_9$)—X—$R_7$ A$^-$ (Id), —alk—O—X—$R_7$ (Ie) or —alk—S—X—$R_7$ (If), $R_3$, $R_4$ and $R_5$ are each independently of the others hydrogen, lower alkyl, halogen, trifluoromethyl, cyano or nitro, $R_6$ is amino, lower alkylamino, lower alkanoylamino, N-lower alkyl-N-lower alkanoyl-amino or di-lower alkylamino, $R_7$ is hydrogen, lower alkyl, amino-lower alkyl, lower alkylamino-lower alkyl, di-lower alkylamino-lower alkyl, lower alkanoylamino-lower alkyl, hydroxy-lower alkyl, lower alkanoyloxy-lower alkyl, polyhalo-lower alkyl, lower alkoxy-lower alkyl, hydroxy-lower alkoxy-lower alkyl, lower alkoxy-lower alkoxy-lower alkyl or polyhalo-lower alkoxy-lower alkyl, 3- to 8-membered cycloalkyl, carboxycycloalkyl, lower alkoxycarbonylcycloalkyl, aminocycloalkyl or mono- or di-lower alkylaminocycloalkyl, pyrrolidino, oxopyrrolidinyl, carboxypyrrolidino, piperidino, carboxypiperidino, lower alkoxycarbonylpiperidino, morpholino or thiomorpholino, carboxy, lower alkoxycarbonyl; phenyl-lower alkoxycarbonyl that is unsubstituted or substituted by lower alkyl, lower alkoxy, hydroxy, halogen and/or by trifluoromethyl; carbamoyl, cyano, lower alkylcarbamoyl, di-lower alkylcarbamoyl, lower alkoxycarbonyl-lower alkylcarbamoyl, carboxy-lower alkylcarbamoyl, carbamoyl-lower alkylcarbamoyl, N-carbamoyl-lower alkyl-N-lower alkyl-carbamoyl; phenylcarbamoyl that is unsubstituted or substituted by lower alkyl, lower alkoxy, polyhalo-lower alkoxy, hydroxy, halogen, nitro, carboxy, lower alkoxycarbonyl, phenyl, phenyloxy and/or by trifluoromethyl; sulfo, lower alkanesulfonyl; benzylsulfonyl that is unsubstituted or substituted by lower alkyl, lower alkoxy, halogen, trifluoromethyl, carboxy and/or by lower alkoxycarbonyl; unsubstituted or di-lower alkylamino-substituted naphthalenesulfonyl, phosphono, tri-lower alkylphosphono, amino, lower alkylamino, di-lower alkylamino, lower alkanoylamino; phenyl-lower alkylamino, benzoylamino or naphthoylamino that is unsubstituted or substituted by lower alkyl, lower alkoxy, halogen and/or by trifluoromethyl; ureido, amidino; phenyl or naphthyl that is unsubstituted or substituted by lower alkyl, lower alkoxy, lower alkylenedioxy, lower alkylidenedioxy, hydroxy, lower alkoxycarbonyl, carboxy, carbamoyl, sulfamoyl, lower alkoxycarbonylamino, lower alkanoyl, halogen and/or by trifluoromethyl; furyl, lower alkylfuryl, thienyl, imidazolyl, oxazolyl, oxazolinyl (dihydrooxazolyl), carboxy-lower alkyl(oxo)oxazolinyl, thiazolyl, thiazolinyl (dihydrothiazolyl), carboxy-lower alkylthiazolyl, lower alkoxycarbonyl-lower alkylthiazolyl, tetrazolyl, pyridyl, pyrazinyl, indolyl, quinolinyl, benzazepinyl or carboxy-lower alkyl-2,3,4,5-tetrahydro-1H-1-benzazepinyl, $R_8$ is hydrogen, lower alkyl, amino-lower alkyl, lower alkylamino-lower alkyl, di-lower alkylamino-lower alkyl, lower alkanoylamino-lower alkyl, hydroxy-lower alkyl, lower alkanoyloxy-lower alkyl, polyhalo-lower alkyl, lower alkoxy-lower alkyl, hydroxy-lower alkoxy-lower alkyl, lower alkoxy-lower alkoxy-lower alkyl, polyhalo-lower alkoxy-lower alkyl; phenyl-lower alkyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl; lower alkanoyl, lower alkenoyl; phenyl-lower alkanoyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl; lower alkoxycarbonyl, or phenyl-lower alkoxycarbonyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl, or $R_7$ and $R_8$, together with X and the nitrogen atom bonding $R_8$ and X, form pyrrolidino, imidazolidino, tetrahydrothiazolyl, piperidino, morpholino, thiomorpholino, piperazino, homopiperidino or 1-azabicyclononyl that is unsubstituted or substituted by lower alkyl, hydroxy-lower alkyl, unsubstituted or substituted phenyl-lower alkyl or phenyl, carboxy, lower alkoxycarbonyl, unsubstituted or substituted phenylcarbamoyl, di-lower alkylamino, lower alkanoylamino, 2-oxoimidazolidino, phosphono, tri-lower alkylphosphono, tetrazolyl, lower alkanoyl, unsubstituted or substituted benzoyl, hydroxy, oxo and/or by lower alkoxy; optionally partially hydrogenated pyrrolyl that is unsubstituted or substituted by carboxy, lower alkoxycarbonyl and/or by lower alkanoyl; furyl; thienyl; imidazolyl that is unsubstituted or substituted by lower alkyl, hydroxy-lower alkyl, carboxy, carboxy-lower alkyl and/or by lower alkoxycarbonylamino-lower alkyl; optionally partially hydrogenated thiazolyl that is unsubstituted or substituted by carboxy-lower alkyl and/or by lower alkoxycarbonyl-lower alkyl; unsubstituted or lower alkyl-substituted pyrazolyl; triazolyl; unsubstituted or oxo-substituted, optionally partially hydrogenated pyridinyl; unsubstituted or oxo-substituted, optionally partially hydrogenated pyrimidinyl; pyrazinyl; indolyl that is unsubstituted or substituted by carboxy, carboxy-lower alkyl, lower alkoxycarbonyl, lower alkoxycarbonyl-lower alkyl, cyano-lower alkyl and/or by nitro; benzofuranyl;

unsubstituted or nitro-substituted benzimidazolyl; tetrahydroquinolinyl; unsubstituted or oxo-substituted tetrahydroisoquinolinyl; tetrahydrobenzazepinyl; or phenyl, cyclohexadienyl, naphthyl or tetrahydronaphthyl that is unsubstituted or substituted by lower alkyl, lower alkoxy, hydroxy, halogen, carboxy, lower alkoxycarbonyl and/or by trifluoromethyl;

$R_9$ is lower alkyl, lower alkenyl, lower alkynyl, or phenyl-lower alkyl that is unsubstituted or substituted by lower alkyl, lower alkoxy, halogen and/or by trifluoromethyl, or $R_7$, $R_8$ and $R_9$, together with X and the nitrogen atom bonding $R_8$, $R_9$ and X, form a pyridinium radical that is unsubstituted or substituted by $C_1$–$C_4$alkyl, amino, $C_1$–$C_4$alkylamino or by di-$C_1$–$C_4$-alkylamino, with $A^-$ being the anion of a hydrohalic acid, lower alkanesulfonic acid or unsubstituted or lower alkyl- or halo-substituted benzenesulfonic acid, alk is lower alkylene, and X (unless, together with $R_7$ and $R_8$ and the nitrogen atom bonding $R_8$ and X or together with the nitrogen atom bonding $R_8$, $R_9$ and X, it forms part of one of the mentioned ring systems) is lower alkylene, lower alkylidene, lower alkenylene, oxo-lower alkylene including carbonyl, oxo-lower alkylidene, dioxo-lower alkylene, oxo-lower alkenylene, hydroxy-lower alkylidene, oxo(hydroxy)-lower alkylene, amino-lower alkylene, amino-lower alkylidene, carboxy-lower alkylene, carboxy-lower alkylidene, carbamoyl-lower alkylidene, lower alkoxycarbonyl-lower alkylidene, lower alkoxycarbonyl-lower alkylene, ω-aza-α-oxo-lower alkylene or ω-aza-α-oxo-lower alkenylene, 3- to 7-membered cycloalkylidene, or unsubstituted or lower alkyl-, lower alkoxy-, lower alkylenedioxy-, lower alkylidenedioxy-, hydroxy-, lower alkoxycarbonyl-, carboxy-, carbamoyl-, lower alkanoyl-, halo- and/or trifluoromethyl-substituted phenyl-lower alkylidene or phenyl-lower alkylene, and salts thereof.

The invention relates especially on the one hand to, for example, compounds of formula I wherein one of the radicals $R_1$ and $R_2$ is a group $R_5$ and the other is a group of formula —alk—CH($R_6$)—$R_7$ (Ib), —alk—N($R_8$)—X—$R_7$ (Ic), —alk—O—X—$R_7$ (Ie) or —alk—S—X—$R_7$ (If), $R_3$, $R_4$ and $R_5$ are each independently of the others hydrogen, lower alkyl, halogen, cyano or nitro, $R_6$ is amino, lower alkylamino, lower alkanoylamino, N-lower alkyl-N-lower alkanoyl-amino or di-lower alkylamino, $R_7$ is carboxy, lower alkoxycarbonyl; phenyl-lower alkoxycarbonyl that is unsubstituted or substituted by lower alkyl, lower alkoxy, hydroxy, halogen and/or by trifluoromethyl; carbamoyl; phenylcarbamoyl that is unsubstituted or substituted by lower alkyl, lower alkoxy, hydroxy, halogen, nitro, carboxy, lower alkoxycarbonyl, phenyl, phenyloxy and/or by trifluoromethyl; phosphono, mono-, di- or tri-lower alkylphosphono or tetrazolyl, $R_8$ is hydrogen, lower alkyl or, together with X and the nitrogen atom bonding $R_8$ and X, forms a pyrrolidinylene, piperidinylene or piperazinylene radical, alk is lower alkylene, and X is lower alkylene, oxo-lower alkylene including carbonyl, lower alkylidene, amino-lower alkylidene, carboxy-lower alkylene, lower alkoxycarbonyl-lower alkylidene, carbamoyl-lower alkylidene or, with the N($R_8$) group, ω-aza-α-oxo-lower alkylene or ω-aza-α-oxo-lower alkenylene bonded via the α-carbon atom; phenyl-lower alkylidene that is unsubstituted or substituted by lower alkyl, lower alkoxy, halogen and/or by trifluoromethyl or in formula Ic, together with $R_8$ and the nitrogen atom bonding $R_8$ and X, forms a pyrrolidinyl, piperidinyl or piperazinyl radical, and salts thereof.

The invention relates especially on the other hand, for example, to compounds of formula I wherein one of the radicals $R_1$ and $R_2$ is a group $R_5$ and the other is a group of formula —alk—N($R_8$)—X—$R_7$ (Ic), $R_3$, $R_4$ and $R_5$ are each independently of the others hydrogen, lower alkyl, halogen, cyano or nitro, $R_7$ is a phenyl, naphthyl, furyl, thienyl, pyridyl or 3- to 8-membered cycloalkyl radical that is unsubstituted or substituted by lower alkyl, lower alkoxy, carboxy, lower alkoxycarbonyl, unsubstituted or lower alkyl-, lower alkoxy-, hydroxy-, halo- and/or trifluoromethyl-substituted phenyl-lower alkoxycarbonyl, carbamoyl, unsubstituted or lower alkyl-, lower alkoxy-, hydroxy-, halo-, nitro-, carboxy-, lower alkoxycarbonyl-, phenyl-, phenyloxy- and/or trifluoromethyl-substituted phenylcarbamoyl, cyano, nitro, halogen and/or by trifluoromethyl, or is lower alkyl, amino-lower alkyl, lower alkylamino-lower alkyl, di-lower alkylamino-lower alkyl, lower alkanoylamino-lower alkyl, hydroxy-lower alkyl, lower alkanoyloxy-lower alkyl, polyhalo-lower alkyl, lower alkoxy-lower alkyl, hydroxy-lower alkoxy-lower alkyl, lower alkoxy-lower alkoxy-lower alkyl or polyhalo-lower alkoxy-lower alkyl, $R_8$ is hydrogen or lower alkyl, alk is lower alkylene, and X is oxo-lower alkylene, and salts thereof.

The invention relates especially to compounds of formula I wherein one of the radicals $R_1$ and $R_2$ is a group $R_5$ and the other is a group of formula —CH($R_6$)—alk—$R_7$ (Ia), —alk—CH($R_6$)—$R_7$ (Ib), —alk—N($R_8$)—X—$R_7$ (Ic), —alk—N$^+$($R_8$)($R_9$)—X—$R_7$ $A^-$ (Id), —alk—X—$R_7$ (Ie) or —alk—S—X—$R_7$ (If), $R_3$, $R_4$ and $R_5$ are each independently of the others hydrogen, $C_1$–$C_4$alkyl, such as methyl or ethyl, halogen having an atomic number of up to and including 35, such as chlorine, fluorine or bromine, trifluoromethyl, cyano or nitro, $R_6$ is amino, $C_1$–$C_4$alkylamino, $C_1$–$C_4$alkanoylamino, N—$C_1$–$C_4$alkyl-N—$C_1$–$C_4$alkanoyl-amino or di-$C_1$–$C_4$alkylamino, $R_7$ is hydrogen, $C_1$–$C_7$alkyl, such as methyl, ethyl, isopropyl, butyl, tert-butyl, pent-4-yl, hept-4-yl, hydroxy-$C_1$–$C_4$alkyl, such as 2-hydroxyethyl, polyhalo-$C_1$–$C_4$alkyl, such as trifluoromethyl, $C_1$–$C_4$alkoxy-$C_1$–$C_4$alkyl, such as methoxymethyl or 2-methoxyethyl, 3- to 6-membered cycloalkyl, such as cyclopropyl or cyclohexyl, 3- to 6-membered carboxycycloalkyl, such as 2-carboxycyclopentyl or 3- or 4-carboxycyclohexyl, 3- to 6-membered aminocycloalkyl, such as 2-aminocyclohexyl, pyrrolidino, carboxypyrrolidino, for example 2-carboxypyrrolidino, oxopyrrolidinyl, for example 5-oxopyrrolidin-2-yl, piperidino, carboxypiperidino, morpholino or thiomorpholino, carboxy, $C_1$–$C_4$alkoxycarbonyl, such as methoxycarbonyl, ethoxycarbonyl or tert-butyloxycarbonyl, phenyl-$C_1$–$C_4$alkoxycarbonyl, such as benzyloxycarbonyl, carbamoyl, cyano, $C_1$–$C_4$alkylcarbamoyl, such as methylcarbamoyl, $C_1$–$C_4$alkoxycarbonylcarbamoyl, such as ethoxycarbonylmethylcarbamoyl or 2-ethoxycarbonylethylcarbamoyl, carboxy-$C_1$–$C_4$alkylcarbamoyl, such as carboxymethylcarbamoyl, carbamoyl-$C_1$–$C_4$alkylcarbamoyl, N-carbamoyl-$C_1$–$C_4$alkyl-N—$C_1$–$C_4$alkyl-carbamoyl, N-carboxy-$C_1$–$C_4$alkyl-N—$C_1$–$C_4$alkyl-carbamoyl, such as N-carboxymethyl-N-methyl-carbamoyl, carbamoyl-$C_1$–$C_4$alkylcarbamoyl, such as carbamoylmethylcarbamoyl, unsubstituted or carboxy-substituted phenyl-$C_1$–$C_4$alkylcarbamoyl, such as benzylcarbamoyl or 1-carboxy-3-phenyl-propylcarbamoyl; phenylcarbamoyl that is unsubstituted or substituted by $C_1$–$C_4$-alkoxy, nitro, polyhalo-$C_1$–$C_4$alkoxy, phenyloxy or by $C_1$–$C_4$alkoxycarbonyl, such as phenylcarbamoyl, 4-trifluoromethoxyphenylcarbamoyl, 4-methoxyphenylcarbamoyl, 2-methoxyphenylcarbamoyl, 4-ethoxycarbonylphenylcarbamoyl, 3-ethoxycarbonylphenylcarbamoyl, 4-phenyloxyphenylcarbamoyl or 4-nitrophenylcarbamoyl; sulfo, $C_1$–$C_4$alkanesulfonyl, such as methanesulfonyl; benzylsulfonyl that is unsubstituted or substituted by $C_1$–$C_4$alkyl, $C_1$–$C_4$-alkoxy and/or by carboxy, such as benzenesulfonyl, toluenesulfonyl, 2-carboxybenzylsulfonyl or 4-methoxybenzenesulfonyl; unsubstituted or di-$C_1$–$C_4$alkylamino-substituted naphthalenesulfonyl, such as 5-dimethylaminonaphthalenesulfonyl, phosphono, amino, $C_1$–$C_4$alkylamino, di-$C_1$–$C_4$alkylamino, such as dimethylamino, $C_1$–$C_4$alkanoylamino, such as acetylamino, phenyl-$C_1$–$C_4$alkylamino, such as benzylamino, benzoylamino or naphthoylamino, ureido, amidino; phenyl or naphthyl that is unsubstituted or substituted by $C_1$–$C_4$alkyl, $C_1$–$C_4$alkoxy, $C_1$–$C_4$alkylenedioxy, $C_1$–$C_4$alkylidenedioxy, carboxy, sulfamoyl, $C_1$–$C_4$alkoxycarbonylamino, $C_1$–$C_4$alkanoyloxy, hydroxy, halogen and/or by trifluoromethyl, such as phenyl, naphthyl, 2-methylphenyl, 3-methoxyphenyl, 4-methoxyphenyl, 3,4,5-trimethoxyphenyl, 3,4-methylenedioxyphenyl, 2-carboxyphenyl, 3-carboxyphenyl, 4-carboxyphenyl or 8-carboxynaphthyl, 4-sulfamoylphenyl, 4-tert-butyloxycarbonylaminophenyl, 2-tert-butyloxycarbonylaminophenyl, 2-acetoxyphenyl, 3,4-dihydroxyphenyl, 2-fluorophenyl, 3-fluorophenyl, 4-fluorophenyl, 3,4-dichlorophenyl or 3,5-bistrifluoromethylphenyl; furyl, such as 2-furyl, $C_1$–$C_4$alkylfuryl, such as 4-methylfur-2-yl, thienyl, imidazolyl, such as imidazol-1-yl or imidazol-4-yl, (oxo) oxazolinyl, such as 2,5-dihydro-3-oxo-1,2-oxazolyl, thiazolyl, thiazolinyl (dihydrothiazolyl), such as 4,5-dihydrothiazolyl, carboxy-$C_1$–$C_4$alkylthiazolyl, such as 4carboxymethylthiazolyl, $C_1$–$C_4$alkoxycarbonyl-$C_1$–$C_4$alkylthiazolyl, such as methoxycarbonylmethylthiazolyl or ethoxycarbonylmethylthiazolyl, tetrazolyl, pyridyl, pyrazinyl, indolyl, such as indol-3-yl, quinolinyl, such as quinolin-4-yl, benzazepinyl or carboxy-$C_1$–$C_4$alkyl-2,3,4,5-tetrahydro-1H-1-benzazepinyl, such as 1-carboxymethyl-2,3,4,5-tetrahydro-1H-1-benzazepino, $R_8$ is hydrogen, $C_1$–$C_4$alkyl, such as methyl, ethyl or isopropyl, hydroxy-$C_1$–$C_4$alkyl, such as 2-hydroxyethyl, $C_1$–$C_4$alkoxy-$C_1$–$C_4$alkyl, such as 2-methoxyethyl, hydroxy-$C_1$–$C_4$alkoxy-$C_1$–$C_4$alkyl, such as 2-(2-hydroxyethoxy)ethyl, phenyl-$C_1$–$C_4$alkyl, such as benzyl, pyridyl-$C_1$–$C_4$alkyl, such as pyridylmethyl, $C_1$–$C_4$alkanoyl, such as acetyl, phenyl-$C_1$–$C_4$alkanoyl, such as phenylacetyl, $C_1$–$C_4$alkoxycarbonyl, such as tert-butyloxycarbonyl, or phenyl-$C_1$–$C_4$alkoxycarbonyl, such as benzyloxycarbonyl, or $R_7$ and $R_8$, together with X and the nitrogen atom bonding $R_8$ and X, form pyrrolidino, carboxypyrrolidino, for example 2-carboxypyrrolidino, hydroxypyrrolidino, for example 3-hydroxypyrrolidino, hydroxy-$C_1$–$C_4$alkylpyrrolidino, for example 2-hydroxymethylpyrrolidino, mono- or di-oxopyrrolidino, for example 2-oxopyrrolidino or 2,5-dioxopyrrolidino, $C_1$–$C_4$alkyl(oxo)pyrrolidino, for example 2-methyl-5-oxo-pyrrolidino, hydroxy-$C_1$–$C_4$alkyl(oxo)-pyrrolidino, for example 2-hydroxymethyl-5-oxo-pyrrolidino, carboxy(oxo) pyrrolidino, for example 5-carboxy-2-oxo-pyrrolidino, 2-carboxy-4-hydroxy-pyrrolidino or 2-carboxy-3-hydroxy-pyrrolidino, 2-oxoimidazolidino, for example 2-oxo-3-phenyl-imidazolidino, tetrahydrothiazolyl, for example tetrahydrothiazol-1-yl, piperidino, $C_1$–$C_4$alkylpiperidino, for example 4-methylpiperidino, 3-methylpiperidino or 4-butylpiperidino, di-$C_1$–$C_4$alkylpiperidino, for example 2,6-dimethylpiperidino, carboxypiperidino, for example 2-carboxypiperidino, 3-carboxypiperidino or 4-carboxypiperidino, $C_1$–$C_4$alkoxycarbonylpiperidino, for example 2-ethoxycarbonylpiperidino or 4-ethoxycarbonylpiperidino, phenylcarbamoylpiperidino, for example 2-phenylcarbamoylpiperidino, 3-phenylcarbamoylpiperidino or 4-phenylcarbamoylpiperidino, oxopiperidino, for example 4-oxopiperidino, dioxopiperidino, oxo(phenyl-$C_1$–$C_4$-alkyl)piperidino, for example 2-benzyl-4-oxo-piperidino, oxo(phenyl)piperidino, for example 2-oxo-3-phenyl-piperidino or 2-oxo-5-phenyl-piperidino, hydroxypiperidino, for example 3-hydroxypiperidino or 4-hydroxypiperidino, hydroxy(phenyl-$C_1$–$C_4$alkyl) piperidino, for example 2-benzyl-4-hydroxy-piperidino, carboxy(hydroxy)piperidino, for example 2-carboxy-4-hydroxy-piperidino, di-$C_1$–$C_4$alkylaminopiperidino, for example 4-dimethylaminopiperidino, $C_1$–$C_4$alkanoylaminopiperidino, for example 4-acetylaminopiperidino, $C_1$–$C_4$alkanoylamino-(phenyl-$C_1$–$C_4$alkyl)piperidino, for example 4-acetylamino-2-benzyl-piperidino, $C_1$–$C_4$alkanoylamino(phenyl) piperidino, for example 4-acetylamino-2-phenyl-piperidino, phenylpiperidino, for example 4-phenylpiperidino, $C_1$–$C_4$alkoxypiperidino, for example 4-methoxypiperidino, $C_1$–$C_4$alkoxy($C_1$–$C_4$alkyl) piperidino, for example 4-methoxy-4-methyl-piperidino, di-$C_1$–$C_4$alkoxypiperidino, for example 4,4-dimethoxypiperidino, di-$C_1$–$C_4$alkoxy-(phenyl-$C_1$–$C_4$-alkyl)piperidino, for example 2-benzyl-4,4-dimethoxypiperidino, $C_1$–$C_4$alkylenedioxypiperidino, for example 4-ethylenedioxypiperidino, hydroxy-$C_1$–$C_4$alkylpiperidino, for example 2-hydroxymethylpiperidino, 4-hydroxymethylpiperidino, 2-(2-hydroxyethyl)piperidino or 4-(1-hydroxyethyl) piperidino, unsubstituted or halogenated benzoylpiperidino, for example 4-(4-fluorobenzoyl) piperidino, $C_1$–$C_4$alkanoylpiperidino, for example 4-acetylpiperidino, oxoimidazolidinopiperidino, for example 4-(2-oxoimidazolidino)piperidino, homopiperidino, oxohomopiperidino, for example 2-oxohomopiperidino, azabicyclononyl, for example 1-azabicyclononyl, piperazino, $C_1$–$C_4$alkylpiperazino, for example 4-methylpiperazino, oxopiperazino, for example 3-oxopiperazino, dioxopiperazino, for example 3,5-dioxopiperazino, unsubstituted or lower alkoxylated phenylpiperazino, for example 4-(4-methoxyphenyl) piperazino, morpholino, di-$C_1$–$C_4$alkylmorpholino, for example 3,5-dimethylmorpholino, thiomorpholino, phenyl, cyclohexa-1,3-dien-5-yl, hydroxyphenyl, such as 4-hydroxyphenyl, $C_1$–$C_4$alkoxyphenyl, such as 3-methoxyphenyl, carboxyphenyl, such as 3-carboxyphenyl, halophenyl, such as 2-fluorophenyl, 3-fluorophenyl or 4-fluorophenyl, trifluoromethylphenyl, bistrifluoromethylphenyl, such as 3,5-bistrifluoromethylphenyl, naphthyl or tetrahydronaphthyl, such as 1,2,3,4-tetrahydronaphthyl, nitrobenzimidazolyl, such as 5-nitrobenzimidazol-1-yl or 6-nitrobenzimidazol-1-yl, tetrahydroquinolinyl, such as 1,2,3,4-tetrahydroquinolin-1-yl, unsubstituted or oxo-substituted tetrahydroisoquinolinyl, such as 1,2,3,4-tetrahydroisoquin-2-yl or 1-oxo-1,2,3,4-tetrahydroisoquin-2-yl, or tetrahydrobenzazepinyl, such as 2,3,4,5-tetrahydro-1H-1-benzazepin-1-yl, $R_9$ is lower alkyl or $R_7$, $R_8$ and $R_9$, together with X and the nitrogen atom bonding $R_8$, $R_9$ and X, form a pyridinium radical that is unsubstituted or substituted by amino, $C_1$–$C_4$alkylamino or by di-$C_1$–$C_4$alkylamino, with $A^-$ being the anion of a hydrohalic acid, alk is $C_1$–$C_4$alkyl(id)ene, such as methylene, ethylene or ethylidene, and X (unless, together with $R_7$ and $R_8$ and the nitrogen atom bonding $R_8$ and X or together with the nitrogen atom bonding $R_8$, $R_9$ and X, it forms part of one of the mentioned ring systems) is a direct bond, $C_1$–$C_4$alkylene, such as ethylene, propylene or butylene, $C_1$–$C_4$alkylidene, such as methylene, ethylidene, isopropylidene, isobutylidene or dimethylpropylidene, $C_1$–$C_4$-alkenylene, such as 1,2-pent-4enylene, oxo-$C_1$–$C_4$alkylene including carbonyl, such as carbonyl, oxoethylene, 1,3-(1-oxo)propylene, 1,3-(1-oxo)propylene or 1,4-(1-oxo)butylene, dioxo-$C_1$–$C_4$alkylene, such as oxalo, oxo-$C_1$–$C_4$alkenylene, such as 1-oxoprop-2-enylene, hydroxy-$C_1$–$C_4$alkylidene, such as 2-hydroxyethylidene or 2-hydroxypropylidene, oxo-(hydroxy)-$C_1$–$C_4$alkylene, such as 1-oxo-2-hydroxyethylene, amino-$C_1$–$C_4$alkylene, such as aminoethylene, amino-$C_1$–$C_4$alkylidene, such as 5-aminopentylidene, carboxy-$C_1$–$C_4$-alkylene, such as 1-carboxyethylene or 1,3-(1-carboxy)propylene, carboxy-$C_1$–$C_4$alkylidene, such as 3-carboxypropylidene, $C_1$–$C_4$alkoxycarbonyl-$C_1$–$C_4$alkylidene, such as ethoxycarbonylmethylene, $C_1$–$C_4$alkoxycarbonyl-$C_1$–$C_4$alkylene, such as 1,3-(1-tert-butyloxycarbonyl)propylene, ω-aza-α-oxo-$C_1$–$C_4$alkylene, such as 1,3-(1-oxo-3-aza)propylene, or ω-aza-α-oxo-$C_1$–$C_4$alkenylene, such as 1,3-(3-aza-1-oxo)prop-2-enylene, 3- to 7-membered cycloalkylidene, such as cyclopropylidene, or unsubstituted or halo- and/or trifluoromethyl-substituted phenyl-$C_1C_4$alkylidene or phenyl-$C_1$–$C_4$alkylene, such as 2-phenylethylidene, 1,2-(1-phenyl)ethylene, 1,2-[1-(4-chlorophenyl)ethylene or 1,3-(3-phenyl)propylene, and salts thereof.

The invention relates especially in each case also to those of the above-mentioned compounds of formula I wherein $R_1$ is a group of formula —CH($R_6$)—alk—$R_7$ (Ia), —alk—CH($R_6$)—$R_7$ (Ib), —alk—N($R_8$)—X—$R_7$ (Ic), —alk—$N^+$($R_8$)($R_9$)—X—$R_7$ $A^-$ (Id), —alk—O—X—$R_7$ (Ie) or —alk—S—X—$R_7$ (If) and $R_2$ is a group $R_5$, wherein $R_3$, $R_4$, $R_5$, $R_6$, $R_7$, $R_8$, $R_9$, alk and X are as defined, with the proviso that in compounds of formula I wherein $R_1$ is a group of formula Ic, $R_2$ and $R_3$ are each independently of the other fluorine, chlorine, bromine, methyl, ethyl or trifluoromethyl and $R_4$ is hydrogen, when alk is methylene, ethylidene or propylidene, the group —N($R_8$)—X—$R_7$ is other than a 5-membered mono-, di-, tri- or tetra-azaheteroaryl radical bonded via a nitrogen atom and optionally benzo-fused and/or substituted by alkyl having up to and including 6 carbon atoms or substituted in the ω-position by a group of formula —N($R_a$)—$R_b$ in which $R_a$ and $R_b$ are each independently of the other hydrogen, alkyl, cycloalkyl, phenyl-lower alkyl or pyridyl-lower alkyl or together with the nitrogen atom bonding them form a pyrrolidino, piperidino, piperazino, N'-lower alkylpiperazino, morpholino or azepino group, and salts thereof.

The invention relates preferably to compounds of formula I wherein $R_1$ is a group of formula —CH($R_6$)—alk—$R_7$ (Ia), —alk—CH($R_6$)—$R_7$ (Ib), —alk—N($R_8$)—X—$R_7$ (Ic) or —alk—$N^+$($R_8$)($R_9$)—X—$R_7$ $A^-$ (Id) and $R_2$ is a group $R_5$, $R_3$, $R_4$ and $R_5$ are each independently of the others hydrogen, $C_1$–$C_4$alkyl, such as methyl or ethyl, halogen having an atomic number of up to and including 35, such as chlorine, fluorine or bromine, trifluoromethyl, cyano or nitro, $R_6$ is amino, $C_1$–$C_4$alkylamino, $C_1$–$C_4$alkanoylamino, N—$C_1$–$C_4$alkyl-N—$C_1$–$C_4$alkanoyl-amino or di-$C_1$–$C_4$alkylamino, $R_7$ is hydrogen, alkyl, such as ethyl, hydroxy-$C_1$–$C_4$alkyl, such as 2-hydroxyethyl, polyhalo-$C_1$–$C_4$alkyl, such as trifluoromethyl, 3- to 6-membered cycloalkyl, such as cyclopropyl, 3- to 6-membered azoxacycloalkyl, such as morpholino, carboxy, $C_1$–$C_4$alkoxycarbonyl, such as methoxycarbonyl, ethoxycarbonyl or tert-butyloxycarbonyl, phenyl-$C_1$–$C_4$alkoxycarbonyl, such as benzyloxycarbonyl, carbamoyl, phenylcarbamoyl, $C_1$–$C_4$alkanesulfonyl, such as methanesulfonyl, amino, morpholino, benzoylamino; phenyl that is unsubstituted or substituted by carboxy, sulfamoyl, $C_1$–$C_4$alkoxy, $C_1$–$C_4$alkanoyloxy, halogen and/or by trifluoromethyl, such as phenyl, 3-methoxyphenyl, 3-carboxyphenyl, 2-fluorophenyl, 3-fluorophenyl, 4-fluorophenyl, 3,5-bistrifluoromethylphenyl; furyl, thienyl, thiazolyl, thiazolinyl (dihydrothiazolyl), such as 4,5-dihydrothiazolyl, carboxy-$C_1$–$C_4$alkylthiazolyl, such as 4-carboxymethylthiazolyl, $C_1$–$C_4$alkoxycarbonyl-$C_1$–$C_4$alkylthiazolyl, such as 4-methoxycarbonylmethylthiazolyl or 4-ethoxycarbonylmethylthiazolyl, or pyridyl, $R_8$ is hydrogen, $C_1$–$C_4$alkyl, such as methyl or ethyl, hydroxy-$C_1$–$C_4$alkyl, such as 2-hydroxyethyl, phenyl-$C_1$–$C_4$alkyl, such as benzyl, or pyridyl-$C_1$–$C_4$alkyl, such as pyridylmethyl, or $R_7$ and $R_8$, together with X and the nitrogen atom bonding $R_8$ and X, form pyrrolidino, carboxypyrrolidino, for example 2-carboxypyrrolidino, hydroxypyrrolidino, for example 3-hydroxypyrrolidino, tetrahydrothiazolyl, for example tetrahydrothiazol-1-yl, piperidino, $C_1$–$C_4$alkylpiperidino, for example 4-methylpiperidino, di-$C_1$–$C_4$alkylpiperidino, for example 2,6-dimethylpiperidino, carboxypiperidino, for example 2-carboxypiperidino, 3-carboxypiperidino or 4-carboxypiperidino, $C_1$–$C_4$alkoxycarbonylpiperidino, for example 2-ethoxycarbonylpiperidino or 4-ethoxycarbonylpiperidino, phenylcarbamoylpiperidino, for example 2-phenylcarbamoylpiperidino, 3-phenylcarbamoylpiperidino or 4-phenylcarbamoylpiperidino, oxopiperidino, for example 4-oxopiperidino, di-$C_1$–$C_4$alkylaminopiperidino, for example 4-dimethylaminopiperidino, hydroxy-$C_1$–$C_4$alkylpiperidino, for example 2-(2-hydroxyethyl)piperidino, homopiperidino, azabicyclononyl, for example 1-azabicyclononyl, piperazino, $C_1$–$C_4$alkylpiperazino, for example 4-methylpiperazino, unsubstituted or lower alkoxylated phenylpiperazino, for example 4-(4-methoxyphenyl)piperazino, morpholino, thiomorpholino, phenyl, cyclohexa-1,3-dien-5-yl, hydroxyphenyl, such as 4-hydroxyphenyl, $C_1$–$C_4$alkoxyphenyl, such as 3-methoxyphenyl, carboxyphenyl, such as 3-carboxyphenyl, halophenyl, such as 2-fluorophenyl, 3-fluorophenyl or 4-fluorophenyl, trifluoromethylphenyl, bistrifluoromethylphenyl, such as 3,5-bistrifluoromethylphenyl, nitrobenzimidazolyl, such as 5-nitrobenzimidazol-1-yl or 6-nitrobenzimidazol-1-yl, tetrahydroquinolinyl, such as 1,2,3,4-tetrahydroquin-1-olin-1-yl, or unsubstituted or oxo-substituted tetrahydroisoquinolinyl, such as 1,2,3,4-tetrahydroisoquin-1-olin-1-yl, $R_9$ is lower alkyl or $R_7$, $R_8$ and $R_9$, together with X and the nitrogen atom bonding $R_8$, $R_9$ and X, form an unsubstituted or amino-substituted pyridinium radical, with $A^-$ being the anion of a hydrohalic acid, alk is $C_1$–$C_4$alkyl(id)ene, such as methylene, and X (unless, together with $R_7$ and $R_8$ and the nitrogen atom bonding $R_8$ and X or together with the nitrogen atom bonding $R_8$, $R_9$ and X, it forms part of one of the mentioned ring systems) is a direct bond, $C_1$–$C_7$alkylene, such as methylene, ethylene, propylene or butylene, $C_1$–$C_4$alkylidene, such as methylene, ethylidene, isopropylidene or 2,2-dimethylpropylidene, oxo-$C_1$–$C_4$alkylene including carbonyl, such as carbonyl, oxoethylene, 1,3-(1-oxo)propylene, 1,4-(1-oxo)butylene, oxo-$C_1$–$C_4$alkenylene, such as 1-oxoprop-2-enylene, amino-$C_1$–$C_4$alkylidene, such as 5-aminopentylidene, carboxy-$C_1$–$C_4$alkylidene, such as 3-carboxypropylidene, $C_1$–$C_4$alkoxycarbonyl-$C_1$–$C_4$alkylidene, ω-aza-α-oxo-$C_1$–$C_4$alkylene, such as 1,3-(1-oxo-3-aza)propylene, or ω-aza-α-oxo-$C_1$–$C_4$alkenylene, such as 1,3-(3-aza-1-oxo)prop-2-enylene, or unsubstituted or halo- and/or trifluoromethyl-substituted phenyl-$C_1$–$C_4$alkylidene, such as 2-phenylethylidene, and salts thereof.

The invention relates especially to compounds of formula I wherein $R_1$ is a group of formula —CH($R_6$)—alk—$R_7$ (Ia), —alk—CH($R_6$)—$R_7$ (Ib), —alk—N($R_8$)—X—$R_7$ (Ic) or —alk—N$^+$($R_8$)($R_9$)–X—$R_7$ $A^-$ (Id) and $R_2$ is a group $R_5$, $R_3$ and $R_4$ are each independently of the other hydrogen, $C_1$–$C_4$alkyl, such as methyl or ethyl, halogen having an atomic number of up to and including 35, such as chlorine, fluorine or bromine, or nitro, $R_5$ is hydrogen, $R_7$ is hydrogen, alkyl, such as ethyl, polyhalo-$C_1$–$C_4$alkyl, such as trifluoromethyl, 3- to 6-membered cycloalkyl, such as cyclopropyl, 3- to 6-membered azoxacycloalkyl, such as morpholino, carboxy, $C_1$–$C_4$alkoxycarbonyl, such as methoxycarbonyl or ethoxycarbonyl; phenyl that is unsubstituted or substituted by carboxy, sulfamoyl, $C_1$–$C_4$alkoxy, halogen and/or by trifluoromethyl, such as phenyl or 3-carboxyphenyl; furyl, such as 2-furyl, thiazolinyl (dihydrothiazolyl), such as 4,5-dihydrothiazolyl, carboxy-$C_1$–$C_4$alkylthiazolyl, such as 4-carboxymethylthiazolyl, or $C_1$–$C_4$alkoxycarbonyl-$C_1$–$C_4$alkylthiazolyl, such as 4-methoxycarbonylmethylthiazolyl or 4-ethoxycarbonylmethylthiazolyl, $R_8$ is hydrogen, $C_1$–$C_4$alkyl, such as methyl or ethyl, or pyridyl-$C_1$–$C_4$alkyl, such as pyridylmethyl, or $R_7$ and $R_8$, together with X and the nitrogen atom bonding $R_8$ and X, form pyrrolidino, piperidino, carboxypiperidino, for example 3-carboxypiperidino or 4-carboxypiperidino, $C_1$–$C_4$alkoxycarbonylpiperidino, for example 2-ethoxycarbonylpiperidino or 4-ethoxycarbonylpiperidino, oxopiperidino, for example 4-oxopiperidino, homopiperidino, azabicyclononyl, for example 1-azabicyclononyl, piperazino, $C_1$–$C_4$alkylpiperazino, for example 4-methylpiperazino, unsubstituted or lower alkoxylated phenylpiperazino, for example 4-(4-methoxyphenyl)piperazino, morpholino or thiomorpholino, $R_9$ is lower alkyl or $R_7$, $R_8$ and $R_9$, together with X and the nitrogen atom bonding $R_8$, $R_9$ and X, form an unsubstituted or amino-substituted pyridinium radical, with $A^-$ being the anion of a hydrohalic acid, alk is $C_1$–$C_4$alkyl(id)ene, such as methylene, and X (unless, together with $R_7$ and $R_8$ and the nitrogen atom bonding $R_8$ and X or together with the nitrogen atom bonding $R_8$, $R_9$ and X, it forms part of one of the mentioned ring systems) is a direct bond, $C_1$–$C_7$alkylene, such as methylene, ethylene, propylene or butylene, $C_1$–$C_4$alkylidene, such as methylene, ethylidene, isopropylidene or 2,2-dimethylpropylidene, oxo-$C_1$–$C_4$alkylene including carbonyl, such as carbonyl, oxoethylene or 1,3-(1-oxo)-propylene, amino-$C_1$–$C_4$alkylidene, such as 5-aminopentylidene, carboxy-$C_1$–$C_4$alkylidene, such as 3-carboxypropylidene, or unsubstituted or halo- and/or trifluoromethyl-substituted phenyl-$C_1$–$C_4$alkylidene, such as 2-phenylethylidene, and salts thereof.

The invention relates especially, for example, to compounds of formula I wherein $R_1$ is a group of formula —alk—CH($R_6$)—$R_7$ (Ib), —alk—N($R_8$)—X—$R_7$ (Ic), —alk—O—$X_2$—$R_7$ (Ie) or —alk—S—$X_2$—$R_7$ (If), $R_2$ is hydrogen, $R_3$ and $R_4$ are each independently of the other halogen having an atomic number of up to and including 35, such as bromine, or nitro, $R_6$ is amino, $R_7$ is carboxy, phenyl-$C_1$–$C_4$alkoxycarbonyl, such as benzyloxycarbonyl; phenylcarbamoyl that is unsubstituted or substituted by $C_1$–$C_4$alkyl, such as methyl, $C_1$–$C_4$alkoxy, such as methoxy, hydroxy, halogen having an atomic number of up to and including 35, such as fluorine, chlorine or bromine, nitro, carboxy, $C_1$–$C_4$alkoxycarbonyl, such as methoxy- or ethoxy-carbonyl, phenyl, phenyloxy and/or by trifluoromethyl; or tetrazolyl, $R_8$ is hydrogen or, together with X and the nitrogen atom bonding $R_8$ and X, forms a piperidinylene radical, alk is methylene, X is $C_1$–$C_4$alkylidene, such as methylene, or in formula Ic is carbonyl, amino-$C_1$–$C_4$alkylidene, such as 5-aminopentylidene, carboxy-$C_1$–$C_4$alkylidene, such as 4-carboxybutylidene, or, with the N($R_8$) group, ω-aza-α-oxo-$C_3$–$C_5$alkylene, such as 1,3-(3-aza-1-oxo)propylene, bonded via the α-carbon atom, or, together with $R_8$ and the nitrogen atom bonding $R_8$ and X, forms a piperidinylene radical, and salts thereof.

The invention relates preferably to compounds of formula I wherein $R_1$ is a group of formula —CH($R_6$)—alk—$R_7$ (Ia), —alk—CH($R_6$)—$R_7$ (Ib), —alk—N($R_8$)—X—$R_7$ (Ic) or —alk—N$^+$($R_8$)($R_9$)—X—$R_7$ A$^-$ (Id) and $R_2$ is a group $R_5$, $R_3$ and $R_4$ are each independently of the other hydrogen, $C_1$–$C_4$alkyl, such as methyl or ethyl, halogen having an atomic number of up to and including 35, such as chlorine, fluorine or bromine, or nitro, $R_5$ is hydrogen, $R_7$ is hydrogen, alkyl, such as ethyl, polyhalo-$C_1$–$C_4$alkyl, such as trifluoromethyl, 3- to 6-membered cycloalkyl, such as cyclopropyl, 3- to 6-membered azoxacycloalkyl, such as morpholino, carboxy, $C_1$–$C_4$alkoxycarbonyl, such as methoxycarbonyl or ethoxycarbonyl; phenyl that is unsubstituted or substituted by carboxy, sulfamoyl, $C_1$–$C_4$alkoxy, halogen and/or by trifluoromethyl, such as phenyl or 3-carboxyphenyl; furyl, such as 2-furyl, thiazolinyl (dihydrothiazolyl), such as 4,5-dihydrothiazolyl, carboxy-$C_1$–$C_4$alkylthiazolyl, such as 4-carboxymethylthiazolyl, or $C_1$–$C_4$alkoxycarbonyl-$C_1$–$C_4$alkylthiazolyl, such as 4-methoxycarbonylmethylthiazolyl or 4-ethoxycarbonylmethylthiazolyl, $R_8$ is hydrogen, $C_1$–$C_4$alkyl, such as methyl or ethyl, or pyridyl-$C_1$–$C_4$alkyl, such as pyridylmethyl, or $R_7$ and $R_8$, together with X and the nitrogen atom bonding $R_8$ and X, form pyrrolidino, piperidino, carboxypiperidino, for example 3-carboxypiperidino or 4-carboxypiperidino, $C_1$–$C_4$alkoxycarbonylpiperidino, for example 2-ethoxycarbonylpiperidino or 4-ethoxycarbonylpiperidino, oxopiperidino, for example 4-oxopiperidino, homopiperidino, azabicyclononyl, for example 1-azabicyclononyl, piperazino, $C_1$–$C_4$alkylpiperazino, for example 4-methylpiperazino, unsubstituted or lower alkoxylated phenylpiperazino, for example 4-(4-methoxyphenyl)piperazino, morpholino or thiomorpholino, alk is $C_1$–$C_4$alkyl(id)ene, such as methylene, and X (unless, together with $R_7$ and $R_8$ and the nitrogen atom bonding $R_8$ and X, it forms part of one of the mentioned ring systems) is a direct bond, $C_1$–$C_7$alkylene, such as methylene, ethylene, propylene or butylene, $C_1$–$C_4$alkylidene, such as methylene, ethylidene, isopropylidene or 2,2-dimethylpropylidene, oxo-$C_1$–$C_4$alkylene including carbonyl, such as carbonyl, oxoethylene or 1,3-(1-oxo)propylene, 1,4-(1-oxo)butylene, oxo-$C_1$–$C_4$alkenylene, such as 1-oxoprop-2-enylene, amino-$C_1$–$C_4$alkylidene, such as 5-aminopentylidene, carboxy-$C_1$–$C_4$-alkylidene, such as 3-carboxypropylidene, $C_1$–$C_4$alkoxycarbonyl-$C_1$–$C_4$alkylidene, ω-aza-α-oxo-$C_1$–$C_4$alkylene, such as 1,3-(1-oxo-3-aza)propylene, or ω-aza-α-oxo-$C_1$–$C_4$alkenylene, such as 1,3-(3-aza-1-oxo)propenyl-2-ylene, or unsubstituted or halo- and/or trifluoromethyl-substituted phenyl-$C_1$–$C_4$alkylidene, such as 2-phenylethylidene, and salts thereof.

The invention relates preferably, for example, on the one hand to compounds of formula I wherein $R_1$ is a group of formula —alk—N($R_8$)—X—$R_7$ (Ic), $R_2$ is hydrogen, $R_3$ and $R_4$ are each independently of the other halogen having an atomic number of up to and including 35, such as bromine, or nitro, $R_6$ is amino, $R_7$ is carboxy, $R_8$ is hydrogen or, together with X and the nitrogen atom bonding $R_8$ and X, forms a piperidinylene radical, alk is methylene and X is $C_1$–$C_4$alkylidene, such as methylene, carbonyl, or, with the N($R_8$) group, forms ω-aza-α-coxo-$C_3$–$C_5$alkylene, such as 1,3-(3-aza-1-oxo)propylene, bonded via the α-carbon atom, or, together with $R_8$ and the nitrogen atom bonding $R_8$ and X, forms a piperidinylene radical, and salts thereof.

The invention relates preferably on the other hand to compounds of formula I wherein $R_1$ is a group of formula —alk—N($R_8$)—X—$R_7$ (Ib), $R_2$, $R_3$, $R_4$ and $R_5$ are each independently of the others hydrogen, $C_1$–$C_4$alkyl, such as methyl or ethyl, halogen having an atomic number of up to and including 35, such as chlorine, fluorine or bromine, cyano or nitro, $R_7$ is a phenyl, furyl, thienyl or pyridyl radical that is unsubstituted or substituted by $C_1$–$C_4$alkyl, such as methyl, $C_1$–$C_4$alkoxy, such as methoxy, carboxy, $C_1$–$C_4$alkoxycarbonyl, such as methoxycarbonyl, carbamoyl, cyano, nitro, halogen and/or by trifluoromethyl, or is unsubstituted 3- to 8-membered cycloalkyl, such as cyclopropyl, $C_1$–$C_7$alkyl, such as methyl, ethyl, propyl, isopropyl, butyl, isobutyl, sec-butyl or tert-butyl, amino-$C_1$–$C_4$alkyl, such as aminomethyl, or polyhalo-$C_1$–$C_4$alkyl, such as trifluoromethyl, $R_8$ is hydrogen, alk is methylene and X is carbonyl, and salts thereof.

The invention relates more especially to compounds of formula I wherein $R_2$ is a group $R_5$ and $R_1$ is a group of formula —alk—N($R_8$)—X—$R_7$ (Ic) or —alk—N$^+$($R_8$)($R_9$)—X—$R_7$ A$^-$ (Id), $R_3$ and $R_4$ are each independently of the other hydrogen, $C_1$–$C_4$alkyl, such as methyl or ethyl, halogen having an atomic number of up to and including 35, such as chlorine, fluorine or bromine, or nitro, $R_5$ is hydrogen, $R_7$ is 3- to 6-membered cycloalkyl, such as cyclopropyl, 3- to 6-membered azoxacycloalkyl, such as morpholino, carboxy, $C_1$–$C_4$alkoxycarbonyl, such as methoxycarbonyl or ethoxycarbonyl, thiazolinyl (dihydrothiazolyi), such as 4,5-dihydrothiazolyl, or $C_1$–$C_4$alkoxycarbonyl-$C_1$–$C_4$alkylthiazolyl, such as 4-methoxycarbonylmethylthiazolyl or 4-ethoxycarbonylmethylthiazolyl, $R_8$ is hydrogen or $C_1$–$C_4$alkyl, such as methyl or ethyl, or $R_7$ and $R_8$, together with X and the nitrogen atom bonding $R_8$ and X, form pyrrolidino, piperidino, carboxypiperidino, for example 4-carboxypiperidino, $C_1$–$C_4$alkoxycarbonylpiperidino, for example 4-ethoxycarbonylpiperidino, oxopiperidino, for example 4-oxopiperidino, or homopiperidino, alk is methylene, and X (unless, together with $R_7$ and $R_8$ and the nitrogen atom bonding $R_8$ and X, it forms part of one of the mentioned ring systems) is a direct bond, $C_1$–$C_7$alkylene, such as methylene, ethylene, propylene or butylene, or amino-$C_1$–$C_4$alkylidene, such as 5-aminopentylidene, or carboxy-$C_1$–$C_4$alkylidene, such as 3-carboxypropylidene, and salts thereof.

The invention relates specifically to the compounds of formula I mentioned in the Examples and salts thereof, especially the pharmaceutically acceptable salts thereof.

The process for the preparation of the compounds of formula I prepared according to the invention is as follows:

a) in a compound of formula II

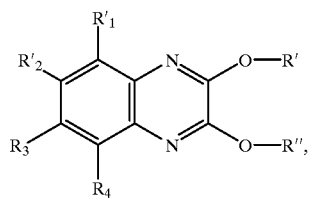

(II)

wherein the radicals R' and R" are identical or different hydroxy-protecting groups, one of the radicals R'₁ and R'₂ is a group R₅ and the other is a group of formula —CH(R'₆)—alk—R₇ (IIa), —alk—CH(R'₆)—R'₇ (IIb), —alk—N(R'₈)—X—R'₇ (IIc), —alk—N⁺(R'₈)(R₉)—X—R'₇ A⁻ (IId), —alk—O—X—R'₇ (IIe) or —alk—S—X—R'₇ (IIf), in which R'₆ is a group R₆ or protected amino, R'₇ is a group R₇, protected carboxy or protected carbamoyl and R'₈ is a group R₈ or an amino-protecting group, the hydroxy-protecting groups R' and/or R" and an amino-protecting group R'₈ which may be present are removed and, if present, carboxy or carbamoyl is freed from protected carboxy R'₇ or protected carbamoyl R'₇, and/or b) for the preparation of compounds of formula I wherein one of the radicals R₁ and R₂ is a group of formula Ic, Ie or If, and salts thereof, compounds of formulae III and IV

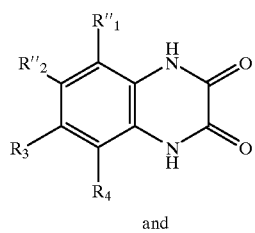

(III)

and

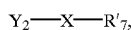

(IV)

wherein one of the radicals R"₁ and R"₂ is a group R₅ and the other is a group of formula —alk—Y₁ (IIIa), one of the radicals Y₁ and Y₂ is hydroxy, mercapto or a H—N(R'₈) group and the other is a group that can be removed to form a bond, R'₇ is a group R₇, protected carboxy or protected carbamoyl and R'₈ is a group R₈ or an amino-protecting group, are condensed with one another, an amino-protecting group R'₈ which may be present is removed and, if present, carboxy or carbamoyl is freed from protected carboxy R'₇ or protected carbamoyl R'₇, or c) for the preparation of compounds of formula I wherein one of the radicals R₁ and R₂ is a group R₅ and the other is a group of formula —alk—CH(R₆)—R₇ (Ib), R₆ is amino and R₇ is carboxy, a compound of formula II

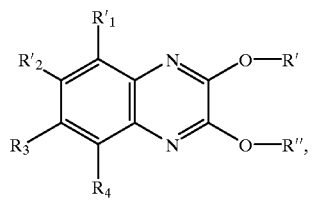

(II)

wherein
one of the radicals R'₁ and R'₂ is a group R₅ and the other is a group of formula —alk—C(R'₇)(R'₆)—R'₇ (IIa'), R' and R" are identical or different hydroxy-protecting groups, R'₆ is protected amino and the groups R'₇ are identical or different protected carboxy groups, is subjected to acid treatment and, if desired, a resulting compound is converted into a different compound of formula I, a mixture of isomers obtainable in accordance with the process is separated into the components and the preferred isomer is isolated and/or a free compound obtainable in accordance with the process is converted into a salt or a salt obtainable in accordance with the process is converted into the corresponding free compound.

Suitable as hydroxy-protecting groups R' and R" are, for example, the hydroxy-protecting groups customary for the temporary protection of lactam groups, especially ether-forming groups, such as lower alkyl, preferably methyl, and also tri-lower alkylsilyl, such as trimethylsilyl.

Amino-protecting groups R'₈ are, for example, acyl groups other than groups R₈, such as acyl derived from an aromatic carboxylic acid or from an aromatic semiester of carbonic acid, such as unsubstituted or substituted benzoyl or unsubstituted or substituted phenylcarbonyl, such as phenyloxycarbonyl.

Protected carboxy groups are, for example, protected in an ester form other than esterified carboxy R₇ and are, for example, in an unsubstituted or substituted phenyl ester form or in the form of tri-lower alkylsilyl esters, such as trimethylsilyl esters. Protected carbamoyl groups are, for example, in phthalimide form.

The removal of the mentioned protecting groups R' and/or R" in accordance with Process variant a) or the freeing of protected groups from groups R'₇ and/or R'₈ is effected in customary manner, for example by acid treatment with, for example, from approximately 20% to approximately 40% hydrobromic acid in acetic acid, or moderately acidic hydrolysis, such as treatment with a mixture of approximately 1 N to approximately 4N hydrochloric acid and acetic acid or tetrahydrofuran/ethanol.

Starting materials of formula II wherein alk is 1,1-lower alkylidene are prepared, for example, as follows: in a corresponding compound of formula V

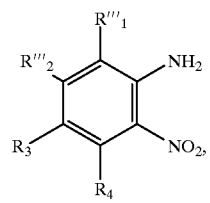

(V)

wherein one of the radicals R'''₁ and R'''₂ is lower alkyl, such as especially methyl, the nitro group is reduced to amino in customary manner, for example by catalytic hydrogenation in the presence of palladium or Raney nickel; the resulting phenylene-1,2-diamine is condensed with oxalic acid under acidic conditions, for example in the presence of hydrochloric acid, to form the corresponding quinoxalinedione of formula VI

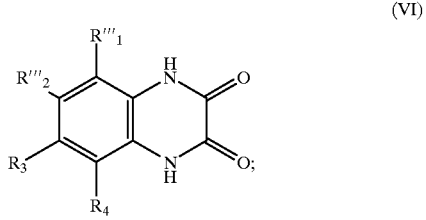

(VI)

that compound is converted by reaction with a halogenating agent that introduces halogen Hal, for example phosphorus oxychloride, into the corresponding 2,3-dihaloquinoxaline of formula VII

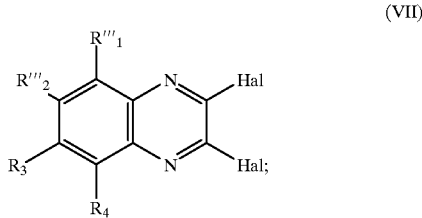

(VII)

in that compound the groups Hal are replaced by protected hydroxy —OR' or —OR", such as lower alkoxy, especially methoxy, in customary manner, for example by reaction with an alkali metal-lower alkanolate, such as sodium methanolate; and the resulting compound of formula VIII

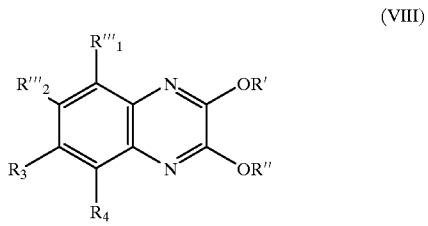

(VIII)

is halogenated in the side chain using a halogenating agent that introduces halogen $Y_1$, such as N-bromosuccinimide in the presence of azo-isobutyronitrile, to form a corresponding compound of formula VIII wherein one of the radicals $R'''_1$ and $R'''_2$ is a group of formula —alk—$Y_1$, and the other is a group $R_5$, wherein $Y_1$ is halogen, especially bromine, and R' and R" are hydroxy-protecting groups.

That compound can then be further reacted with a compound of formula $CH_2(R'_6)$—$R'_7$ (VIIIa), H—N($R'_8$)—X—$R'_7$ (VIIIb), HO—X—$R'_7$ (VIIIc) or HS—X—$R'_7$ (VIIId), wherein $R'_6$ is an amino group protected by a divalent araliphatic radical, such as benzylidene or especially benzhydryl, $R'_7$ is a group $R_7$, protected carboxy or protected carbamoyl and $R'_8$ is a group $R_8$ or an amino-protecting group.

That process is especially suitable for the preparation of compounds of formula II wherein one of the radicals $R'_1$ and $R'_2$ is a group $R_5$ and the other is a group of formula —alk—CH($R_6$)—$R'_7$ (II'b) wherein $R_6$ is amino, a group of formula —alk—N($R'_8$)—X—$R'_7$ (IIc) wherein $R'_7$ is a radical $R_7$ other than hydrogen, X has no oxo group in the α-position and is, for example, lower alkylene or lower alkylidene and $R_8$ is hydrogen or an aliphatic or araliphatic radical or $R'_7$ and $R'_8$, together with X and the nitrogen atom bonding $R'_8$ and X, form an unsubstituted or substituted mono- or di-azacycloalkyl, azoxacycloalkyl, azathiacycloalkyl or optionally oxidized thiacycloalkyl radical bonded via a nitrogen atom, or a group of formula —alk—S—X—$R'_7$ (IIf) wherein $R'_7$ is a group $R_7$.

For the preparation of compounds of formula II wherein one of the radicals $R'_1$ and $R'_2$ is a group of formula —alk—N($R'_8$)—X—$R'_7$ (IIc; $R_8$=hydrogen) and the other is a group $R_5$, it is also possible to react a compound of formula IX

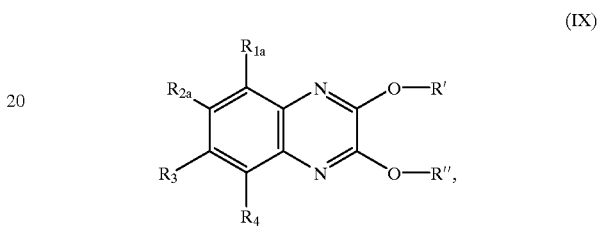

(IX)

wherein the radicals R' and R" are identical or different hydroxy-protecting groups, one of the radicals $R_{1a}$ and $R_{2a}$ is a group $R_5$ and the other is lower alkanoyl, such as acetyl or especially formyl, with an amine of formula H—N($R'_8$)—X—$R'_7$ under reducing conditions, for example in the presence of a di-light metal hydride, such as an alkali metal borohydride.

Compounds of formula II wherein one of the radicals $R_{1a}$ and $R_{2a}$ is a group $R_5$ and the other is a group of formula —CH($R'_6$)—alk—$R_7$ (IIa) wherein $R_7$ is carboxy and alk is preferably methylene can be obtained, for example, by reacting an aldehyde of formula IX wherein one of the radicals $R_{1a}$ and $R_{2a}$ is a group $R_5$ and the other is formyl, in the presence of a boron trifluoride etherate with a lower alkylcarbamate and an ω-tri-lower alkylsilyl-lower alkene of formula H—CH=CH—alk—Si(lower alkyl)$_3$, the formyl group being converted into a group of formula —CH($R'_6$)—alk—CH=CH$_2$ (II'a), and in the intermediate so obtainable oxidizing the terminal ethenyl group in customary manner, for example by means of sodium iodate/ruthenium oxide.

Aldehydes of formula IX wherein one of the radicals $R_{1a}$ and $R_{2a}$ is a group $R_5$ and the other is formyl can be obtained starting from a halogen compound VIII wherein one of the radicals $R'''_1$ and $R'''_2$ is halogen, such as bromine, and the other is a group $R_5$ by reaction with a vinyl tri-lower alkylstannane, such as vinyl-tributyl-stannane, preferably in the presence of bis(triphenylphosphine)palladium(II) chloride and lithium chloride, to form a corresponding compound of formula VIII wherein one of the radicals $R'''_1$ and $R'''_2$ is vinyl and the other is a group $R_5$, and oxidation thereof, for example with ozone/oxygen at from -80° C. to -40° C. and subsequent reaction with triphenylphosphine.

An alternative process for the preparation of compounds of formula IX wherein $R_{1a}$ is formyl, $R_3$ is hydrogen or nitro and $R_{2a}$ and $R_4$ are hydrogen comprises treating a compound of formula VIII wherein $R'''_1$ is a group of formula —alk—$Y_1$, wherein $Y_1$ is halogen, and $R'''_2$, $R_3$ and $R_4$ are hydrogen, with 2-nitropropane in a lower alkanol at from 40° C. to 100° C. and in the presence of an alkali metal-lower alkanolate, for example in boiling methanol/sodium methanolate, and, if desired, nitrating the resulting product, preferably by treatment with nitric acid, sulfuric acid and trifluoroacetic acid anhydride in trifluoroacetic acid.

Ketones of formula IX wherein one of the radicals $R_{1a}$ and $R_{2a}$ is a group $R_5$ and the other is lower alkanoyl, for example acetyl, can be obtained starting from halogen compounds VIII wherein one of the radicals $R'''_1$ and $R'''_2$ is halogen, such as bromine, and the other is a group $R_5$ in the presence of a palladium catalyst, such as bis(triphenylphosphine)palladium(II) chloride and lithium chloride, preferably in dimethylformamide with heating with a 1-lower alkoxy-lower alkenyl-tri-lower alkyl-stannane, there being obtained with acidic working-up the corresponding compounds of formula IX wherein one of the radicals $R_{1a}$ and $R_{2a}$ is lower alkanoyl and the other is a group $R_5$.

Halogen compounds of formula VIII wherein one of the radicals $R'''_1$ and $R'''_2$ is a group of formula —alk—$Y_1$ and the other is a group $R_5$, wherein $Y_1$ is halogen, are used as starting materials also in an advantageous process for the preparation of compounds of formula II wherein one of the radicals $R'_1$ and $R'_2$ is a group $R_5$ and the other is a group of formula —alk—N($R'_8$)—X—$R'_7$ (IIC) wherein $R'_7$ is a radical $R_7$ and $R'_8$ is hydrogen. According to that process, the halogen compound of formula VIII is converted in customary manner, for example by treatment with an alkali metal alkanolate, such as sodium methanolate, into the corresponding compound of formula VIII wherein one of the radicals $R'''_1$ and $R'''_2$ is formyl and that compound is reacted further under reducing conditions, for example in the presence of sodium borohydride, with a compound of formula H—N($R'_8$)—X—$R'_7$ (VIIIb).

For the preparation of compounds of formula II wherein one of the radicals $R'_1$ and $R'_2$ is a group $R_5$ and the other is a group of formula —alk—N($R'_8$)—X—$R'_7$ (IIc) wherein $R'_7$ is a radical $R_7$ other than hydrogen, X has an oxo group in the α-position and is, for example, oxo-lower alkylene or carbonyl and $R_8$ is hydrogen, in a compound of formula VIII wherein one of the radicals $R'''_1$ and $R'''_2$ is a group of formula —alk—Y, and the other is a group $R_5$, wherein $Y_1$ is halogen, halogen $Y_1$ is converted into azido in customary manner, for example by reaction with an alkali metal azide or ammonium azide, such as sodium azide, preferably in dimethylformamide, the azido group is reduced to amino in customary manner, for example by treatment with triphenylphosphine in water, and the resulting compound of formula VIII wherein one of the radicals $R'''_1$ and $R'''_2$ is a group of formula —alk—$Y_1$ and the other is a group $R_5$, wherein $Y_1$ is amino, is reacted with an acid of formula HO—X—$R_7$ (VIIIe) or a reactive derivative thereof, such as an acid halide, for example of formula Hal-X—$R_7$ (VIIIe$_1$), an anhydride, for example of formula $R_7$—X—O—X—$R_7$ (VIIIe$_2$), a sulfonic acid anhydride, such as methanesulfonic acid anhydride, an aromatic or araliphatic isocyanate, for example of formula ONC—$R_7$ (VIIIe$_3$) or an aliphatic dicarboxylic acid anhydride, for example succinic acid anhydride.

Starting from amine compounds of formula VIII wherein one of the radicals $R'''_1$ and $R'''_2$ is a group of formula —alk—$Y_1$ and the other is a group $R_5$ and $Y_1$ is amino, it is also possible to prepare compounds of formula II wherein one of the radicals $R'_1$ and $R'_2$ is a group $R_5$ and the other is a group of formula —alk—N($R'_8$)—X—$R'_7$ (IIc) wherein $R'_7$ is esterified phosphono $R_7$, such as di-lower alkylphosphono, X is methylene and $R_8$ is hydrogen by treatment first with formaldehyde, for example in ethanol with formalin solution, and reaction of the resulting trimeric intermediate in the presence of a halosilane, such as a tri-lower alkylchlorosilane, with a diester of phosphorous acid, such as a di-lower alkylphosphite.

For the preparation of compounds of formula II wherein one of the radicals $R'_1$ and $R'_2$ is a group $R_5$ and the other is a group of formula —alk—O—X—$R'_7$ (IIe), in a preparation method alternative to that above there are likewise used as starting materials compounds of formula VIII wherein one of the radicals $R'''_1$ and $R'''_2$ is a group of formula —alk—$Y_1$ and the other is a group $R_5$ and $Y_1$ is halogen, and the group—alk—$Y_1$ therein is hydrolyzed to the corresponding group —alk—OH and the reaction product is reacted with a compound of formula Hal—X—$R'_7$ (VIIIg) wherein Hal is halogen and $R'_7$ is a group $R_7$, protected carboxy or protected carbamoyl.

Compounds of formula II wherein one of the radicals $R'_1$ and $R'_2$, especially $R'_1$, is a group of formula —alk—N($R_8$)—X—$R'_7$ (IIc) wherein alk is lower alkylidene, $R_8$ is hydrogen and X and $R'_7$ are as defined, and the other is a radical $R_5$, can be prepared also by reacting a corresponding compound of formula VIII wherein one of the radicals $R'''_1$ and $R'''_2$ is halogen, such as bromine, and the other is a group $R_5$ in the presence of a palladium catalyst, preferably in dimethylformamide, with heating, with a 1-lower alkoxy-lower alkenyl-tri-lower alkyl-stannane, preferably in the presence of a palladium catalyst, such as bis(triphenylphosphine)palladium(II) chloride and lithium chloride, there being obtained with acidic working-up a corresponding compound of formula VIII wherein one of the radicals $R'''_1$ and $R'''_2$ is lower alkanoyl and the other is a group $R_5$; that compound is condensed with a compound of formula $H_2N$—X—$R'_7$ and in a resulting compound of formula VIII wherein one of the radicals $R'''_1$ and $R'''_2$ is a group of formula —alk'=N—X—$R'_7$ and the other is a group $R_5$, wherein alk' is lower alkenylidene, the extracyclic double bond is reduced to a single bond in customary manner, for example by means of sodium borohydride. That process variant is especially suitable for the preparation of compounds of formula II wherein one of the radicals $R'_1$ and $R'_2$, especially $R'_1$, is a group of formula —alk—N($R'_8$)—X—$R'_7$ (IIc) wherein alk is ethylidene, X is lower alkylene or lower alkylidene or a direct bond and $R'_8$ is hydrogen, and the other is a radical $R_5$, the mentioned compounds of formula VIII being reacted with 1-ethoxyvinyl-tributyl-stannane to form the corresponding compounds of formula VIII wherein one of the radicals $R'''_1$ and $R'''_2$ is acetyl and the other is a group $R_5$.

In an analogous manner there are also obtained compounds of formula II wherein one of the radicals $R'_1$ and $R'_2$, especially $R'_1$, is a group of formula —alk—N($R'_8$)—X—$R'_7$ (IIc) or —alk—O—X—$R'_7$ (Ie), alk is ethylene, and $R'_8$ is hydrogen and $R'_7$ and X are as defined, by reacting the above-defined halogen compound VIII wherein one of the radicals $R'''^1$ and $R'''_2$ is halogen, such as bromine, and the other is a group $R_5$ with a vinyl-tri-lower alkyl-stannane, such as vinyl-tributyl-stannane, preferably in the presence of bis(triphenylphosphine)palladium(II) chloride and lithium chloride, to form the corresponding compound of formula VIII wherein one of the radicals $R'''_1$ and $R'''_2$ is vinyl and the other is a group $R_5$; that compound is converted by customary hydroboration and subsequent oxidation into the corresponding compound of formula VIII wherein one of the radicals $R'''_1$ and $R'''_2$ is 2-hydroxyethyl and the other is a group $R_5$, and if desired the 2-hydroxyethyl group is converted into 2-aminoethyl by reaction first with methanesulfonyl chloride, then with an alkali metal azide and finally with triphenylphosphine and, if desired, the amino group is substituted by reductive amination by a group of formula —N($R'_8$)—X—$R'_7$.

Unless otherwise indicated, the above reactions of compounds of formula VIII are carried out in customary manner, preferably in an inert organic solvent, such as tetrahydrofuran, dioxane or dimethylformamide, or in a two-phase system, such as benzene/water or toluene/water, if necessary in the presence of a basic condensation agent, such as a tertiary aliphatic amine, such as triethylamine, or a tertiary aromatic nitrogen base, such as pyridine, a quaternary aliphatic or araliphatic ammonium salt, such as tetramethylammonium hydrogen sulfate, or a metal base, such as an alkali metal hydroxide, alkali metal carbonate or alkali metal amide, for example sodium or potassium hydroxide, sodium or potassium carbonate or sodium or potassium amide, and also optionally other excipients, N-(3-dimethylaminopropyl)-N'-ethyl-carbodiimide hydrochloride/1-hydroxybenzotriazole, if necessary with heating, for example in a temperature range of approximately from 25° to 120°, preferably from 50° to 120°.

Groups that can be removed to form a bond in accordance with Process variant b) are, for example, reactive esterified hydroxy groups, such as hydroxy groups esterified by a mineral acid or sulfonic acid, especially halogen atoms, for example chlorine, bromine or iodine, or hydroxy groups esterifed by an aliphatic or an unsubstituted or substituted aromatic sulfonic acid, for example lower alkanesulfonyloxy, such as methanesulfonyloxy, or unsubstituted or substituted benzenesulfonyloxy, such as benzenesulfonyloxy, bromobenzenesulfonyloxy or toluenesulfonyloxy, in the reaction of compounds of formula III wherein $Y_1$ is a H—N($R_8$)-group or hydroxy with α-carbonyl compounds of formula IV wherein X has an oxo group in the α-position relative to $Y_2$, also free or etherified hydroxy groups, such as hydroxy, lower alkoxy, benzyloxy, optionally nitrated phenyloxy or groups of formula —O—X—R'$_7$, such as groups $Y_2$ derived from carboxylic acid anhydrides or sulfonic acid anhydrides. Compounds of formula IV containing such groups are, for example, carboxylic acids of formula HOOC—X—R$_7$ (IVa) wherein X is lower alkylene, lower alkenylene, lower alkylidene, carbonyl, amino-lower alkylidene, carbamoyl-lower alkylidene or lower alkoxycarbonyl-lower alkylidene, carboxylic acid halides of formula Hal—C(=O)—X—R'$_7$ (IVb) wherein X is lower alkylene, lower alkylidene, carbonyl or a bond, carboxylic acid anhydrides of formula R'$_7$—X—C(=O)—O—C(=O)—X—R$_7$ (IVc) wherein X is lower alkylene, lower alkylidene or a bond, sulfonyl halides of formula Hal—S(O$_2$)—X—R$_7$ (IVd), sulfonic acid anhydrides of formula R$_7$—S(O$_2$)—O—S(O$_2$)—R$_7$ (IVe), and also dicarboxylic acid anhydrides, such as succinic acid anhydride.

The reaction of compounds of formulae III and IV according to Process variant b) is carried out in customary manner, preferably in an inert organic solvent, such as tetrahydrofuran, dioxane or dimethylformamide, or in a two-phase system, such as benzene/water or toluene/water, if necessary in the presence of a basic condensation agent, such as a tertiary aliphatic amine, such as triethylamine, or a tertiary aromatic nitrogen base, such as pyridine, a quaternary aliphatic or araliphatic ammonium salt, such as tetramethylammonium hydrogen sulfate, or a metal base, such as an alkali metal hydroxide, alkali metal carbonate or alkali metal amide, for example sodium or potassium hydroxide, sodium or potassium carbonate or sodium or potassium amide, and also optionally other excipients, N-(3-dimethylaminopropyl)-N'-ethyl-carbodiimide hydrochloride/1-hydroxybenzotriazole, if necessary with heating, for example in a temperature range of approximately from 25° to 120°, preferably from 50° to 120°.

In a preferred embodiment of the invention, for example a compound of formula III wherein $Y_1$ is hydroxy is reacted in the presence of a quaternary aliphatic ammonium salt, such as tetraethylammonium hydrogen sulfate, in a two-phase system, such as benzene/water, with a compound of formula IV wherein $Y_2$ is halogen, such as bromine.

In a further preferred embodiment of the invention, for example a compound of formula III wherein $Y_1$ is amino is reacted in the presence of a tertiary aliphatic amine, such as triethylamine, N-(3-dimethylaminopropyl)-N'-ethyl-carbodiimide hydrochloride and 1-hydroxybenzotriazole, with a compound of formula HOOC—X—R$_7$ (IVa) wherein the group —C(O)—X— is α-oxo-lower alkylene, ω-aza-α-oxo-lower alkylene or ω-aza-α-oxo-lower alkenylene, or with a carboxylic acid anhydride of formula R'$_7$X—C(=O)—O—C(=O)—X—R$_7$ (IVc) wherein X is lower alkylene, lower alkylidene or a bond.

The starting materials of formula III can be prepared in a manner known per se, for example by halogenating a compound of formula VIII

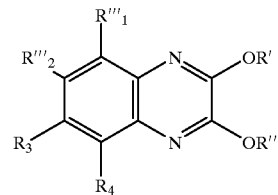

(VIII)

in the side chain with a halogenating agent that introduces halogen $Y_1$, such as N-bromosuccinimide in the presence of azo-isobutyronitrile, to form a corresponding compound of formula VIII wherein one of the radicals R'''$_1$ and R'''$_2$ is a group of formula —alk—$Y_1$ and the other is a group R$_5$, wherein $Y_1$ is halogen, especially bromine, and R' and R" are hydroxy-protecting groups and removing the hydroxy-protecting groups R' and R" or, if desired, converting the resulting compound of formula VIII wherein one of the radicals R'''$_1$, and R'''$_2$ is a group of formula —alk—$Y_1$ and the other is a group R$_5$, wherein $Y_1$ is halogen, in customary manner, for example by basic hydrolysis, for example in the presence of potassium carbonate, into the corresponding compound of formula III wherein $Y_1$ is hydroxy, or by reaction with an alkali metal azide, such as sodium azide, in dimethylformamide and then with triphenylphosphine in tetrahydrofuran and in each case removal of the hydroxy-protecting groups R' and R" into the corresponding compounds of formula III wherein $Y_1$ is amino.

Protected amino groups R'$_6$ in compounds of formula II wherein one of the radicals R"$_1$ and R"$_2$ is a group R$_5$ and the other is a group of formula —alk—C(R'$_7$)(R'$_6$)—R'$_7$ (IIa') in accordance with Process variant c) are, for example, amino protected by one of the amino-protecting groups mentioned under Process variant a), for example lower alkanoylamino or lower alkoxycarbonylamino. Protected carboxy groups R'$_7$ are, for example, esterified carboxy groups, such as lower alkoxycarbonyl or tri-lower alkylsilyloxycarbonyl groups, and also unsubstituted or substituted phenyl-lower alkoxycarbonyl or phenyloxycarbonyl groups. In the acid treatment, the protected carboxy groups R'$_7$ are hydrolyzed to carboxy, one of them is decarboxylated, and the amino-protecting group R'$_6$ and, where present, the hydroxy-protecting groups R' and/or R" are removed.

Starting materials for Process variant c) can be prepared, for example, by reacting a compound of formula III wherein one of the radicals R"$_1$ and R"$_2$ is —alk—Y, and Y$_1$ is reactively esterified hydroxy, such as halogen or one of the sulfonyloxy groups mentioned, in customary manner with an aminomalonic acid derivative of formula H—C(R'$_6$)(R'$_7$)—R'$_7$.

Compounds obtainable in accordance with the process can be converted in customary manner into different compounds of formula I.

For example, aliphatic, araliphatic or cycloaliphatic radicals, such as lower alkyl, or acyl derived from aliphatic, araliphatic carboxylic acids, from aliphatic or araliphatic semiesters or from aliphatic, araliphatic or aromatic semiamides of carbonic acid or an aliphatic or aromatic sulfonic acid or from phosphoric acid or from a phosphonic acid ester, such as lower alkanoyl, lower alkanesulfonyl or the acyl radical of a lower alkane-, lower alkene- or lower alkyne-dicarboxylic acid, for example lower alkylfumaroyl, can be introduced in customary manner, for example by reaction with a lower alkylating agent, such as a lower alkylhalide or a reactive lower alkanoic acid derivative, such as a lower alkanoic acid chloride or lower alkanoic acid nitrile, lower alkanesulfonic acid anhydride or lower alkanesulfonic acid chloride or a lower alkane-, lower alkene- or lower alkyne-dicarboxylic acid di-lower alkyl ester, for example a fumaric acid lower alkyl ester, if necessary in the presence of a customary basic condensation agent. In particular, in compounds of formula I wherein one of the radicals R$_1$ and R$_2$ is a group of formula Ic and R$_8$ is hydrogen, a radical other than hydrogen can be introduced.

Furthermore, in a compound of formula I wherein one of the radicals R$_1$ and R$_2$ is a group of formula Ic, Id or If wherein X is a bond and R$_7$ and/or R$_8$ are hydrogen, a hydrogen atom R$_7$ and/or R$_8$ can be replaced in customary manner by a radical R$_7$ and/or R$_8$ other than hydrogen.

Furthermore, compounds of formula I containing esterified or amidated carboxy groups can be hydrolysed in customary manner to form the corresponding carboxylic acids, and compounds of formula I containing free carboxy can be esterified or amidated in customary manner.

Furthermore, in resulting compounds of formula I, cyano can be converted into tetrazolyl in customary manner, for example by reaction with hydrazoic acid.

Resulting salts can be converted into the free compounds in a manner known per se, for example by treatment with a base, such as an alkali metal hydroxide, a metal carbonate or metal hydrogen carbonate, or another salt-forming base mentioned earlier in the process description, or with an acid, such as a mineral acid, for example with hydrochloric acid, or another salt-forming acid mentioned earlier in the process description.

Resulting salts can be converted into different salts in a manner known per se; acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula I, including their salts, may also be obtained in the form of hydrates or may include the solvent used for crystallization.

In view of the close relationship between the novel compounds in free form and in the form of their salts, hereinabove and hereinbelow any reference to the free compounds and their salts is to be understood as including also the corresponding salts and free compounds, respectively, as appropriate and expedient.

Resulting diastereoisomeric mixtures and mixtures of racemates can be separated into the pure diastereoisomers or racemates in known manner on the basis of the physicochemical differences between the constituents, for example by chromatography and/or fractional crystallization.

Resulting racemates can also be resolved into the optical antipodes in accordance with known methods, for example by recrystallization from an optically active solvent, with the aid of microorganisms or by reaction of the resulting diastereoisomeric mixture or racemate with an optically active auxiliary compound, for example depending on the acidic, basic or functionally modifiable groups present in compounds of formula I, with an optically active acid, base or an optically active alcohol, to form mixtures of diastereoisomeric salts or functional derivatives, such as esters, and separation thereof into the diastereoisomers from which the desired enantiomer can be freed in the appropriate customary manner. Bases, acids and alcohols suitable for that purpose are, for example, optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as quinic acid or D- or L-tartaric acid, D- or L-di-o-toluyltartaric acid, D- or L-malic acid, D- or L-mandelic acid or D- or L-camphorsulfonic acid, and optically active alcohols, such as borneol or D- or L-(1-phenyl)ethanol.

The invention relates also to those forms of the process according to which a compound obtainable as intermediate at any stage of the process is used as starting material and the remaining steps are carried out or a starting material is used in the form of a salt or, especially, is formed under the reaction conditions.

The invention relates also to the novel starting materials, which have been developed especially for the preparation of the compounds according to the invention, especially those starting materials which result in the compounds of formula I described as preferred earlier in the specification, to processes for the preparation thereof and to the use thereof as intermediates.

That applies especially to compounds of formula IX

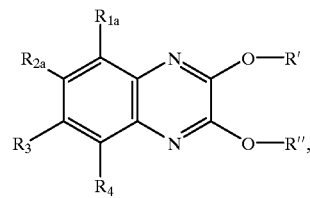

wherein the radicals R' and R" are identical or different hydroxy-protecting groups, one of the radicals R$_{1a}$ and R$_{2a}$ is a group R$_5$ and the other is lower alkanoyl, such as especially formyl or acetyl, or a group of formula —CH(R'$_6$)—alk—R$_7$ (IIa), —alk—CH(R'$_6$)—R'$_7$ (IIb), —alk—N(R'$_8$)—X—R'$_7$ (IIc), —alk—N$^+$(R'$_8$)(R$_9$)—X—R'$_7$ A$^-$ (IId), —alk—O—X—R'$_7$ (IIe), —alk—S—X—R'$_7$ (IIf) or —alk—Y$_1$ (IIIa) wherein Y$_1$ is hydroxy, reactive esterified hydroxy, mercapto or a group of formula —N(R'$_8$)—H, R'$_7$ is a group R$_7$ other than hydrogen, or is protected carboxy or protected carbamoyl and R'$_8$ is a group R$_8$ or an amino-protecting group, wherein R$_3$, R$_4$, R$_5$, R$_6$, R$_7$, R$_8$, alk and X are as defined for compounds of formula I, especially the preferred groups of compounds of formula I, with the proviso that in compounds of formula I wherein $R_{1a}$ is lower alkanoyl or a group of formula IIc, IIe or IIIa, when $R_{2a}$, and $R_3$ are each independently of the other fluorine, chlorine, bromine, methyl, ethyl or trifluoromethyl and $R_4$ is hydrogen, lower alkanoyl $R_1a$ is other than formyl or the group IIc is other than a 5-membered mono-, di-, tri- or tetra-azaheteroaryl radical that is bonded via a nitrogen atom and is optionally benzo-fused and/or substituted by alkyl having up to and including 6 carbon atoms or substituted in the co-position by a group of formula —N($R_a$)—$R_b$ wherein $R_a$ and $R_b$ are each independently of the other hydrogen, alkyl, cycloalkyl, phenyl-lower alkyl or pyridyl-lower alkyl or together with the nitrogen atom bonding them form a pyrrolidino, piperidino, piperazino, N'-lower alkylpiperazino, morpholino or azepino group, or the group IIe or IIIa is other than hydroxymethyl, 1-hydroxyethyl and 1-hydroxypropyl or the group IIIa is other than halomethyl, 1-haloethyl and 1-halopropyl, and salts thereof.

The invention relates preferably to compounds of formula IX wherein
the radicals R' and R" are identical or different hydroxy-protecting groups,
one of the radicals $R_{1a}$ and $R_{2a}$ is a group $R_5$ and the other is lower alkanoyl, such as especially formyl or acetyl, or a group of formula —alk—N(R'$_8$)—X—R'$_7$ (IIc), —alk—N$^+$(R'$_8$)(R$_9$)—X—R'$_7$ A$^-$ (IId), —alk—O—X—R'$_7$ (IIe), —alk—S—X—R'$_7$ (IIf) or —alk—$Y_1$ (IIIa), $Y_1$ is hydroxy, halogen, lower alkanesulfonyloxy, sulfonyloxy or a group of formula —N(R'$_8$)—H, R'$_7$ is a group $R_7$, protected carboxy or protected carbamoyl and R'$_8$ is a group $R_8$ or an amino-protecting group,
$R_{2a}$ is a group $R_5$,
$R_3$, $R_4$ and $R_5$ are each independently of the other hydrogen, $C_1$–$C_4$alkyl, halogen having an atomic number of up to and including 35, cyano or nitro,
$R_6$ is amino,
$R_7$ is carboxy; $C_1$–$C_4$alkoxycarbonyl; phenyl-$C_1$–$C_4$alkoxycarbonyl that is unsubstituted or substituted by $C_1$–$C_4$alkyl, such as methyl, $C_1$–$C_4$alkoxy, hydroxy, halogen having an atomic number of up to and including 35 and/or by trifluoromethyl; carbamoyl; phenylcarbamoyl that is unsubstituted or substituted by $C_1$–$C_4$alkyl, $C_1$–$C_4$alkoxy, hydroxy, halogen having an atomic number of up to and including 35, nitro, carboxy, $C_1$–$C_4$alkoxycarbonyl, phenyl, phenyloxy and/or by trifluoromethyl; tetrazolyl or phosphono,
$R_8$ is hydrogen or, together with X and the nitrogen atom bonding $R_8$ and X, forms a pyrrolidinylene, piperidinylene or piperazinylene radical,
alk is $C_1$–$C_4$alkylene and
X is carbonyl, $C_1$–$C_4$alkylene, $C_1$–$C_4$alkylidene, amino-$C_1$–$C_4$alkylidene, carboxy-$C_1$–$C_4$-alkylidene or, with the N($R_8$) group, ω-aza-α-oxo-$C_3$–$C_5$alkylene or ω-aza-α-oxo-$C_3$–$C_5$-alkenylene each bonded via the α-carbon atom, phenyl-$C_1$–$C_4$alkylidene, such as 2-phenylethylidene, or in formula Ic, together with $R_8$ and the nitrogen atom bonding $R_8$ and X, forms a pyrrolidinylene, piperidinylene or piperazinylene radical, and salts thereof.

The invention relates preferably to compounds of formula IX wherein
the radicals R' and R" are identical or different lower alkyl groups, $R_{1a}$ is a group of formula (IIIa) wherein $Y_1$ is hydroxy, halogen or a group of formula —N(R'$_8$)—H wherein R'$_8$ is a group $R_8$,
$R_2a$ is a group $R_5$,
$R_3$, $R_4$ and $R_5$ are each independently of the other hydrogen, $C_1$–$C_4$alkyl, halogen having an atomic number of up to and including 35, cyano or nitro, and
alk is $C_1$–$C_4$alkylene,
and salts thereof.

The invention relates also to pharmaceutical compositions comprising the compounds according to the invention or pharmaceutically acceptable salts thereof as active ingredients, and to processes for the preparation thereof.

The pharmaceutical compositions according to the invention, which comprise the compounds according to the invention or pharmaceutically acceptable salts thereof, are for enteral, such as oral and also rectal, and parenteral administration to (a) warm-blooded animal(s), the compositions comprising the pharmacological active ingredient alone or together with a pharmaceutically acceptable carrier. The daily dose of the active ingredient depends upon age and individual condition and upon the mode of administration.

The novel pharmaceutical compositions comprise, for example, from approximately 10% to approximately 80%, preferably from approximately 20% to approximately 60%, active ingredient. Pharmaceutical compositions according to the invention for enteral or parenteral administration are, for example, those in unit dose forms, such as dragées, tablets, capsules or suppositories, and also ampoules. They are prepared in a manner known per se, for example by means of conventional mixing, granulating, confectioning, dissolving or lyophilizing processes. For example, pharmaceutical compositions for oral administration can be obtained by combining the active ingredient with solid carriers, optionally granulating a resulting mixture, and processing the mixture or granules, if desired or necessary, after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, if desired disintegrators, such as the above-mentioned starches, and also carboxymethyl starch, cross-linked polyvinylpyrrolidone, agar, alginic acid or a salt thereof, such as sodium alginate. Excipients are especially flow agents, flowconditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical compositions are hard gelatin capsules and also soft, sealed capsules consisting of gelatin and a plasticizer, such as glycerol or sorbitol. The hard gelatin capsules may comprise the active ingredient in the form of granules, for example in admixture with fillers, such as lactose, binders, such as starches, and/or glidants, such as talc or magnesium stearate, and if desired stabilizers. In soft capsules the active ingredient is preferably dissolved or suspended in suitable liquids, such as fatty oils, paraffin oil or liquid polyethylene glycols, it likewise being possible to add stabilizers.

Suitable rectally administrable pharmaceutical compositions are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules which comprise a combination of the active ingredient with a base material. Suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions which comprise viscosity-increasing substances, for example sodium carboxymethylcellulose, sorbitol and/or dextran, and optionally also stabilizers.

The dose of the active ingredient depends upon the species of warm-blooded animal, age and individual condition and also upon the mode of administration. In a normal case the approximate daily dose for oral administration to a patient weighing about 75 kg is estimated to be from approximately 10 mg to approximately 500 mg.

The following Examples serve to illustrate the invention; temperatures are given in degrees Celsius, pressures in mbar.

EXAMPLE 1

N-(7-Bromo-2,3-dioxo-1,2,3,4-tetrahydroquinoxalin-5-ylmethyl)-glycine Hydrobromide 380 mg (0.921 mmol) of N-(7-bromo-2,3-dimethoxy-quinoxalin-5-ylmethyl)-glycine tert-butyl ester are dissolved in 6 ml of an approximately 25% solution of hydrogen bromide in acetic acid and the solution is stirred for two hours at 70° C. The mixture is cooled to 20° C. and diluted with diethyl ether. The solid is filtered off and washed with diethyl ether. After drying under a high vacuum, the title compound is obtained in the form of a white powder.

$^1$H-NMR (250 MHz, DMSO-D$_6$+5% D$_2$O) δ=7.42, 7.37 (2d, 2H), 4.32 (s, 2H), 3.91 (s, 2H). MS: 328.2 (M+H)$^+$. M.p.=281° C. (decomp.).

The starting material can be prepared, for example, as follows:

a) 5-Bromo-2.3-diamino-toluene

A solution of 15 g (64.9 mmol) of 4-bromo-2-methyl-6-nitro-aniline in 300 ml of ethanol is hydrogenated in the presence of 1.5 g of Raney nickel for 4 hours at approximately 27° C. The reaction mixture is then filtered and concentrated by evaporation. The title compound is obtained in the form of a brown oil.

$^1$H-NMR (250 MHz, CDCl$_3$) δ=6.76, 6.73 (2d, 2H), 3.22 (s, 2NH$_2$), 2.14 (s, Me).

b) 7-Bromo-5-methyl-1,4-dihydroquinoxaline-2.3-dione 13.05 g (64.9 mmol) of 5-bromo-2,3-diamino-toluene and 6.42 g (1.1 equiv.) of oxalic acid are stirred at reflux for 16 hours in 2N hydrochloric acid. The mixture is cooled and the solid is filtered off and washed with water. The title compound is obtained in the form of a brown solid.

$^1$H-NMR (250 MHz, DMSO) δ=11.98, 11.32 (2s, 2NH), 7.13 (s, 2H), 2.33 (s, Me).

c) 7-Bromo-2,3-dichloro-5-methyl-quinoxaline 17 g (66.6 mmol) of 7-bromo-5-methyl-1,4-dihydro-quinoxaline-2,3-dione are stirred in 80 ml of phosphorus oxychloride for 5 hours at reflux and for 40 hours at 20° C. The mixture is concentrated by evaporation and dried under a high vacuum. A saturated potassium carbonate solution is carefully added to the residue, and the solid is filtered off and washed with water. The title compound is obtained in the form of a brown solid.

$^1$H-NMR (250 MHz, DMSO) δ=8.16,7.99 (2d, 2H), 2.63 (s, Me).

d) 7-Bromo-5-methyl-2,3-dimethoxy-quinoxaline 2.97 g (129.5 mmol) of sodium are dissolved in 100 ml of methanol. The solution is added to 18.9 g (64.7 mmol) of 7-bromo-5-methyl-2,3-dichloro-quinoxaline in 60 ml of methanol and the mixture is heated at reflux for 20 hours. The mixture is cooled and 15 ml of water are added. The solid is filtered off and washed with methanol and water. The title compound is obtained in the form of a beige solid.

$^1$H-NMR (250 MHz, DMSO) δ=7.73, 7.58 (2d, 2H), 4.05, 4.03 (2s, 2Me), 2.58 (s, Me).

e) 7-Bromo-5-bromomethyl-2,3-dimethoxy-quinoxaline 15 g (53 mmol) of 7-bromo-5-methyl-2,3-dimethoxy-quinoxaline, 9.9 g (1.05 equiv.) of N-bromosuccinimide and 0.87 g (0.1 equiv.) of azo-isobutyronitrile are dissolved in 100 ml of carbon tetrachloride and the solution is stirred at reflux for 24 hours. The solid is filtered off and the filtrate is diluted with dichloromethane, then washed once with each of water and brine. The organic phase is dried over magnesium sulfate and concentrated by evaporation. The residue is recrystallized from ethyl acetate and hexane. The title compound is obtained in the form of light-orange crystals.

$^1$H-NMR (250 MHz, CDCl$_3$) δ=7.90, 7.68 (2d, 2H), 4.95 (s, 2H), 4.20, 4.13 (2s, 2Me).

f) N-(7-Bromo-2,3-dimethoxy-quinoxalin-5-ylmethyl)-glycine tert-butyl ester 850 mg (2.35 mmol) of 7-bromo-5-bromomethyl-2,3-dimethoxy-quinoxaline, 0.982 ml of triethylamine and 719 mg of glycine tert-butyl ester hydrochloride are dissolved in 15 ml of acetonitrile and the solution is stirred at reflux for 18 hours. The mixture is concentrated by evaporation and the residue is dissolved in diethyl ether and washed with aqueous 5% sodium carbonate solution and brine. The organic phases are combined, dried over magnesium sulfate and concentrated by evaporation. The residue is chromatographed on silica gel with ethyl acetate and petroleum ether (1:2). The title compound is obtained in the form of a yellow oil.

$^1$H-NMR (250 MHz, CDCl$_3$) δ=7.88, 7.57 (2d, 2H), 4.20 (s, 2H), 4.15, 4.12 (2s, 2Me), 3.32 (s, 2H), 1.42 (s, 9H).

EXAMPLE 2

The following compounds are also prepared in a manner analogous to that described under Example 1:

N-(7-bromo-2,3-dioxo-1,2,3,4-tetrahydroquinoxalin-5-ylmethyl)-β-alanine hydrobromide, m.p.=271° C. (decomp.);

N-(7-bromo-2,3-dioxo-1,2,3,4-tetrahydroquinoxalin-5-ylmethyl)-(L)-glutamic acid hydrobromide, m.p.=220° C. (decomp.);

N-(7-bromo-2,3-dioxo-1,2,3,4-tetrahydroquinoxalin-5-ylmethyl)-(L)-phenylalanine hydrobromide, m.p.=249° C. (decomp.);

α-N-(7-bromo-2,3-dioxo-1,2,3,4-tetrahydroquinoxalin-5-ylmethyl)-(L)-lysine dihydrobromide, m.p.=256° C. (decomp.);

N-(7-bromo-2,3-dioxo-1,2,3,4-tetrahydroquinoxalin-5-ylmethyl)-piperidine-2-carboxylic acid ethyl ester hydrobromide, m.p.=240° C. (decomp.);

N-(7-bromo-2,3-dioxo-1,2,3,4-tetrahydroquinoxalin-5-ylmethyl)-piperidine-4-carboxylic acid ethyl ester hydrobromide, m.p.>250° C.;

N-(7-bromo-2,3-dioxo-1,2,3,4-tetrahydroquinoxalin-5-ylmethyl)-piperidine-3-carboxylic acid ethyl ester hydrobromide, m.p.>260° C.

EXAMPLE 3

The following compounds are prepared in a manner analogous to that described under Example 1 but starting from 7-bromo-5-bromomethyl-2,3-dimethoxy-8-nitro-quinoxaline instead of 7-bromo-5-bromomethyl-2,3-dimethoxy-quinoxaline:

7-bromo-5-(5-nitro-benzimidazol-1-ylmethyl)-1,4-dihydro-quinoxaline-2,3-dione hydrobromide, m.p.=246° C. (decomp.);

7-bromo-5-(6-nitro-benzimidazol-1-ylmethyl)-1,4-dihydro-quinoxaline-2,3-dione hydrobromide, m.p.=278° C. (decomp.);

N-(7-bromo-2,3-dioxo-8-nitro-1,2,3,4-tetrahydroquinoxalin-5-ylmethyl)-4-dimethylamino-piperidine dihydrobromide, m.p.=209° C. (decomp.);

N-(7-bromo-2,3-dioxo-8-nitro-1,2,3,4-tetrahydroquinoxalin-5-ylmethyl)-1,2,3,4-tetrahydroquinoline hydrobromide, m.p.=213° C. (decomp.);

N-(7-bromo-2,3-dioxo-8-nitro-1,2,3,4-tetrahydroquinoxalin-5-ylmethyl)-β-alanine hydrobromide, m.p.=254° C. (decomp.);

α-N-(7-bromo-2,3-dioxo-8-nitro-1,2,3,4-tetrahydroquinoxalin-5-ylmethyl)-(L)-lysine dihydrobromide, m.p.=180° C. (decomp.);

N-(7-bromo-2,3-dioxo-8-nitro-1,2,3,4-tetrahydroquinoxalin-5-ylmethyl)-(L)-phenylalanine hydrobromide, m.p.=218° C. (decomp.);

N-(7-bromo-2,3-dioxo-8-nitro-1,2,3,4-tetrahydroquinoxalin-5-ylmethyl)-glycine hydrobromide, m.p.=238° C. (decomp.); and N-(7-bromo-2,3-dioxo-8-nitro-1,2,3,4-tetrahydroquinoxalin-5-ylmethyl)-piperidine-4-carboxylic acid ethyl ester hydrobromide, m.p.=260° C. (decomp.).

The starting material can be prepared, for example, as follows:

a) 7-Bromo-5-bromomethyl-2,3-dimethoxy-8-nitro-quinoxaline 20 ml of sulfuric acid are cooled to 0° C. and then 5 g (13.8 mmol) of 7-bromo-5-bromomethyl-2,3-dimethoxy-quinoxaline are added. After a further 15 minutes, 1.46 g (1.05 equiv.) of potassium nitrate are added and the mixture is stirred for 15 hours at 20° C. The mixture is poured onto ice, and the solid is filtered off and washed with water. The title compound is obtained in the form of a beige solid.

$^1$H-NMR (250 MHz, DMSO-D$_6$) δ=8.14 (s, H), 5.09 (s, 2H), 4.12, 3.99 (2s, 2Me).

EXAMPLE 4

The following compounds are also prepared in a manner analogous to that described under Example 1 but starting from 5-bromomethyl-2,3-dimethoxy-7-nitro-quinoxaline instead of 7-bromo-5-bromomethyl-2,3-dimethoxy-quinoxaline:

N-(2,3-dioxo-7-nitro-1,2,3,4-tetrahydroquinoxalin-5-ylmethyl)-piperidine-4-carboxylic acid ethyl ester hydrobromide, m.p.=287° C. (decomp.);

N-(2,3-dioxo-7-nitro-1,2,3,4-tetrahydroquinoxalin-5-ylmethyl)-β-alanine hydrobromide, m.p.=241° C. (decomp.);

α-N-(2,3-dioxo-7-nitro-1,2,3,4-tetrahydroquinoxalin-5-ylmethyl)-(D)-lysine dihydrobromide, m.p.=185° C. (decomp.);

N-(2,3-dioxo-7-nitro-1,2,3,4-tetrahydroquinoxalin-5-ylmethyl)-glycine hydrobromide, m.p.=271° C. (decomp.);

N-(2,3-dioxo-7-nitro-1,2,3,4-tetrahydroquinoxalin-5-ylmethyl)-(L)-glutamic acid hydrobromide, m.p.=143° C. (decomp.);

N-(2,3-dioxo-7-nitro-1,2,3,4-tetrahydroquinoxalin-5-ylmethyl)-(L)-phenylaianine hydrobromide, m.p.=204° C. (decomp.); and α-N-(2,3-dioxo-7-nitro-1,2,3,4-tetrahydroquinoxalin-5-ylmethyl)-(L)-lysine dihydrobromide, m.p.=150° C. (decomp.).

The starting material, 5-bromomethyl-2,3-dimethoxy-7-nitro-quinoxaline, can be prepared, for example, as follows:

A$_1$) 5-Bromomethyl-2,3-dimethoxy-quinoxaline

The title compound can be prepared in a manner analogous to that described under Examples 1c, 1d and 1e, starting from 5-methyl-2,3-dioxo-1,2,3,4-tetrahydroquinoxaline (CAS registry number 61875-33-0).

B$_1$) 5-Bromomethyl-2,3-dimethoxy-7-nitro-quinoxaline 25 ml of sulfuric acid are cooled to 0° C. and then 9.5 g (33.55 mmol) of 5-bromomethyl-2,3-dimethoxy-quinoxaline are added. After a further 10 minutes, 3.39 ml (1 equiv.) of isopropyl nitrate are added and the mixture is stirred at 0° C. for 1 hour. The mixture is poured onto ice, and the solid is filtered off and washed with water. The title compound is obtained in the form of a beige solid.

$^1$H-NMR (250 MHz, DMSO-D$_6$) δ 8.62, 8.40 (2d, 2H), 5.02 (s, 2H), 4.27, 4.19 (2s, 2Me).

5-Bromomethyl-2,3-dimethoxy-7-nitro-quinoxaline can also be prepared as follows:

a2) 5-Methyl-7-nitro-quinoxaline-2,3-dione

A mixture of 9.3 g (55.63 mmol) of 2,3-diamino-5-nitro-toluene and 14 g of oxalic acid in 93 ml of 6N HCl is heated at reflux for 30 minutes and then stirred at room temperature overnight to complete the reaction. The suspension is filtered and then washed with water, taken up in 250 ml of 2N NaOH and heated at reflux until a homogeneous solution is formed. After cooling, the mixture is acidified to pH 3 and the resulting 5-methyl-7-nitro-quinoxaline-2,3-dione is filtered off.

b2) 2,3-Dichloro-5-methyl-7-nitro-quinoxaline 62 ml of POCl$_3$ are added to the 5-methyl-7-nitro-quinoxaline-2,3-dione obtained according to a2) and the mixture is heated at reflux for 18 hours. The excess POCl$_3$ is removed under reduced pressure. The residue is neutralized with 10% aqueous sodium carbonate solution, filtered and dried.

c2) 2,3-Dimethoxy-5-methyl-7-nitro-quinoxaline

The crude 2,3-dichloro-5-methyl-7-nitro-quinoxaline obtained according to b2 is taken up in a solution of 1.24 g (27 mmol) of sodium in 140 ml of methanol and heated at boiling for 4 hours. After cooling, the mixture is concentrated using a rotary evaporator, neutralized with 2N HCl, extracted with ethyl acetate, dried over sodium sulfate, filtered and concentrated by rotary evaporation. Filtration over silica gel using methylene chloride as eluant yields the title compound in the form of yellowish crystals. M.p.: 167–168° C., TLC: hexane/ethyl acetate 9/1: Rf=0.40.

d2) 5-Bromomethyl-2,3-dimethoxy-7-nitro-quinoxaline

A suspension of 0.249 g (1.0 mmol) of 2,3-dimethoxy-5-methyl-7-nitro-quinoxaline, 0.178 g (1 mmol) of N-bromosuccinimide and 0.016 g (0.1 mmol) of azo-isobutyronitrile in 3 ml of CCl$_4$ is heated at reflux for 20 hours. The reaction mixture is washed with water and brine and concentrated using a rotary evaporator. Crystallization from ethyl acetate yields the title compound. TLC: hexane/ ethyl acetate 6/1: Rf=0.63, $^1$H-NMR (CDCl$_3$): δ 8.64 (d, J=3, 1H), 8.41 (d, J=3, 1H), 5.02(s, 2H), 4.27(s, 3H), 4.20 (s, 3H).

EXAMPLE 5

The following compounds are also prepared in a manner analogous to that described under Example 1 but starting from 6-methyl-7-nitro-1,4-dihydroquinoxaline-2,3-dione instead of 7-bromo-5-methyl-1,4-dihydroquinoxaline-2,3-dione:

N-(2,3-dioxo-7-nitro-1,2,3,4-tetrahydroquinoxalin-6-ylmethyl)-β-alanine hydrobromide, m.p.=305° C. (decomp.);

α-N-(2,3-dioxo-7-nitro-1,2,3,4-tetrahydroquinoxalin-6-ylmethyl)-(L)-lysine dihydrobromide, m.p.=230° C. (decomp.);

N-(2,3-dioxo-7-nitro-1,2,3,4-tetrahydroquinoxalin-6-ylmethyl)-(L)-phenylalanine hydrobromide, m.p.=228° C. (decomp.);

N-(2,3-dioxo-7-nitro-1,2,3,4-tetrahydroquinoxalin-6-ylmethyl)-(L)-glutamic acid hydrobromide, m.p.=235° C. (decomp.);

N-(2,3-dioxo-7-nitro-1,2,3,4-tetrahydroquinoxalin-5-ylmethyl)-glycine hydrobromide, m.p.=270° C. (decomp.);

N-(2,3-dioxo-7-nitro-1,2,3,4-tetrahydroquinoxalin-6-ylmethyl)-piperidine-4-carboxylic acid hydrochloride, m.p.=255° C. (decomp.);

N-(2,3-dioxo-7-nitro-1,2,3,4-tetrahydroquinoxalin-6-ylmethyl)-piperidine-4-carboxylic acid ethyl ester, m.p.=288–289° C. (decomp.).

EXAMPLE 6

N-(7-Bromo-2,3-dioxo-1,2,3,4-tetrahydroquinoxalin-5-ylmethyl)-piperidine-4-carboxylic acid 1.28 g (3.12 mmol) of N-(7-bromo-2,3-dioxo-1,2,3,4-tetrahydroquinoxalin-5-ylmethyl)-piperidine-4-carboxylic acid ethyl ester hydrobromide (penultimate compound in Example 2) are stirred at 20° C. for 16 hours in 12 ml of 2N sodium hydroxide solution. The mixture is acidified with 2N hydrochloric acid, and the resulting solid is filtered off and washed with water and diethyl ether. The title compound is obtained in the form of a white solid.

$^1$H-NMR (250 MHz, DMSO-D$_6$+10% D$_2$O) δ 7.45, 7.38 (2d, 2H), 4.46 (s, 2H), 3.4 (m, 2H), 3.0 (m, 2H), 2.05 (m, 2H), 1.9 (m, H), 1.7 (m, H). MS: 381 (M$^1$). M.p.>300° C.

EXAMPLE 7

N-(7-Bromo-2,3-dioxo-1,2,3,4-tetrahydroquinoxalin-5-ylmethyl)-piperidine-4-carboxylic acid phenylamide 382 mg (1 mmol) of N-(7-bromo-2,3-dioxo-1,2,3,4-tetrahydroquinoxalin-5-ylmethyl)-piperidine-4-carboxylic acid (Example 6), 186 mg (2 equiv.) of aniline, 480 mg (2.5 equiv.) of N-(3-dimethylaminopropyl)-N'-ethyl-carbodiimide hydrochloride and 384 mg (2.5 equiv.) of 1-hydroxy-benzotriazole are stirred at 20° C. in dried dimethylformamide for 48 hours. The mixture is poured into water and extracted three times with 100 ml of dichloromethane. The organic phases are combined and concentrated by evaporation. The residue is dissolved in 30 ml of dichloromethane and the solution is stirred for 30 minutes. The white solid is filtered off, washed with dichloromethane and dried.

$^1$H-NMR (250 MHz, DMSO-D$_6$) 12.0, 11.8 (2s, 2NH), 9.9 (s, NH), 7.6 (d, 2H), 7.30–7.15 (m, 4H), 7.01 (t, H), 3.77 (s, 2H), 2.95 (m, 2H), 2.38 (m, 1H), 2.05 (m, 2H), 1.85–1.60 (m, 4H). MS: 456 (M$^1$). M.p.>250° C.

EXAMPLE 8

The following compounds are also prepared in a manner analogous to that described under Examples 6 and 7:

N-(7-bromo-2,3-dioxo-8-nitro-1,2,3,4-tetrahydroquinoxalin-5-ylmethyl)-piperidine-4-carboxylic acid hydrochloride, m.p.=278° C. (decomp.);

N-(2,3-dioxo-7-nitro-1,2,3,4-tetrahydroquinoxalin-5-ylmethyl)-piperidine-4-carboxylic acid hydrochloride, m.p.=294° C. (decomp.);

N-(7-bromo-2,3-dioxo-1,2,3,4-tetrahydroquinoxalin-5-ylmethyl)-piperidine-2-carboxylic acid hydrochloride, m.p.=225–240° C. (decomp.);

N-(7-bromo-2,3-dioxo-1,2,3,4-tetrahydroquinoxalin-5-ylmethyl)-piperidine-3-carboxylic acid, m.p.>250° C.;

N-(7-bromo-2,3-dioxo-1,2,3,4-tetrahydroquinoxalin-5-yimethyl)-piperidine-3-carboxylic acid phenylamide hydrochloride, m.p.>260° C.; and N-(7-bromo-2,3-dioxo-1,2,3,4-tetrahydroquinoxalin-5-ylmethyl)-piperidine-2-carboxylic acid phenylamide.

EXAMPLE 9

5-Aminomethyl-7-bromo-2.3-dioxo-1,2,3,4-tetrahydroquinoxaline hydrochloride 150 mg (0.5 mmol) of 5-aminomethyl-7-bromo-2,3-dimethoxy-1,2,3,4-tetrahydroquinoxaline are dissolved in 3 ml of acetic acid and 3 ml of 48% hydrogen bromide solution in acetic acid. After 18 hours at 20° C., the mixture is diluted with diethyl ether, and the solid is filtered off and washed with diethyl ether.

$^1$H-NMR (250 MHz, DMSO-D$_6$) δ 12.15, 11.75 (2s, 2NH), 8.10 (br, NH$_2$), 7.42, 7.35 (2d, 2H), 4.28, 4.20 (m, 2H). M.p.>250° C.

The starting material can be prepared, for example, as follows:

a) 5-Azidomethyl-7-bromo-2,3-dimethoxy-1,2,3,4-tetrahydroquinoxaline 743 mg (2 equiv.) of sodium azide are added at 20° C. to 2.07 g (5.72 mmol) of 7-bromo-5-bromomethyl-2,3-dimethoxy-quinoxaline in 25 ml of dimethylformamide. After 3 hours, the mixture is poured into water, extracted with diethyl ether, washed with water and brine and dried with magnesium sulfate. The solvent is concentrated by evaporation.

$^1$H-NMR(250 MHz, CDCl$_3$) δ 7.92, 7.58 (2d, 2H), 4.80 (s, 2H), 4.18, 4.13 (2s, 2Me).

b) 5-Aminomethyl-7-bromo-2,3-dimethoxy-1,2,3,4-tetrahydroquinoxaline 4.47 g (13.8 mmol) of 5-azidomethyl-7-bromo-2,3-dimethoxy-1,2,3,4-tetrahydroquinoxaline are dissolved in 35 ml of tetrahydrofuran, and 3.98 g (1.1 equiv.) of triphenylphosphine are added. The mixture is stirred at 20° C. for 4 hours. 746 mg of water are added and the mixture is stirred for a further three hours. The solid is filtered off and the filtrate is extracted with ethyl acetate and sodium carbonate solution. The organic phases are combined, washed with brine, dried over magnesium sulfate and concentrated by evaporation. The residue is chromatographed on silica gel with ethyl acetate/petroleum ether (1:1).

$^1$H-NMR (250 MHz, CDCl$_3$) δ 7.85, 7.53 (2d, 2H), 4.22 (s, 2H), 4.12 (s, 2Me).

EXAMPLE 10

3-[(7-Bromo-2,3-dioxo-1,2,3,4-tetrahydroquinoxalin-5-ylmethyl)-carbamoyl]-acrylic acid ethyl ester 351 mg (1 mmol) of 5-aminomethyl-7-bromo-2,3-dioxo-1,2,3,4-tetrahydroquinoxaline hydrochloride, (Example 2) 217 mg (1.5 equiv.) of fumaric acid monoethyl ester, 0.210 ml of triethylamine, 383 mg (2 equiv.) of N-(3-dimethylaminopropyl)-N'-ethyl-carbodiimide hydrochloride and 270 mg (2 equiv.) of 1-hydroxy-benzotriazole are stirred at 20° C. in dried dimethylformamide for 18 hours. The mixture is poured into 700 ml of water and 3 ml of 1 N hydrochloric acid and stirred for 15 minutes. The solid is filtered off, washed with water and dried.

$^1$H-NMR (250 MHz, DMSO-D$_6$) δ 12.0, 11.4 (2s, 2NH), 9.18 (t, NH), 7.23, 7.18 (2d, 2H), 7.05, 6.64 (2d, 2H), 4.50 (d, 2H), 4.18 (q, 2H), 1.24 (t, 3H). MS: 395 (M). M.p.= 288–293° C.

EXAMPLE 11
3-[(7-Bromo-2,3-dioxo-1,2,3,4-tetrahydroquinoxalin-5-ylmethyl)-carbamoyl]-acrylic acid 144 mg (0.36 mmol) of 3-[(7-bromo-2,3-dioxo-1,2,3,4-tetrahydroquinoxalin-5-ylmethyl)-carbamoyl]-acrylic acid ethyl ester (Example 10) and 76 mg of lithium hydroxide hydrate are dissolved in 18 ml of tetrahydrofuran/water (2:1) and the solution is stirred for 18 hours. 50 ml of water are added, the tetrahydrofuran is concentrated by evaporation and the solution is acidified with 1 N hydrochloric acid. The solid is filtered off, washed with water and dried.

$^1$H-NMR (250 MHz, DMSO-D$_6$) δ 12.9 (COOH), 12.05, 11.38 (2s, 2NH), 9.17 (t, NH), 7.24, 7.18 (2d, 2H), 6.98, 6.60 (2d, 2H), 4.50 (d, 2H). MS: 367 (M$^+$). M.p.>250° C.

EXAMPLE 12
3-[(7-Bromo-2,3-dioxo-1,2,3,4-tetrahydroquinoxalin-5-ylmethyl)-carbamoyl]acrylic acid phenylamide The title compound is prepared in a manner analogous to that described under Example 7 but starting from 3-[(7-bromo-2,3-dioxo-1,2,3,4-tetrahydroquinoxalin-5-ylmethyl)-carbamoyl]-acrylic acid (Example 11) instead of N-(7-bromo-2,3-dioxo-1,2,3,4-tetrahydroquinoxalin-5-ylmethyl)-piperidine-4-carboxylic acid hydrobromide. M.p.>250° C.

EXAMPLE 13
The following compounds are also prepared in a manner analogous to that described under Examples 9 to 12:
N-(7-bromo-2,3-dioxo-1,2,3,4-tetrahydroquinoxalin-5-ylmethyl)-2-(3-phenyl-ureido)-acetamide, m.p.>300° C.;
{[(7-bromo-2,3-dioxo-1,2,3,4-tetrahydroquinoxalin-5-ylmethyl)-carbamoyl]-methyl}-carbamic acid tert-butyl ester, m.p.=238–242° C. (decomp.);
{[(7-bromo-2,3-dioxo-1,2,3,4-tetrahydroquinoxalin-5-ylmethyl)-carbamoyl]-methyl}-carbamic acid benzyl ester, m.p.=225–230° C. (decomp.).

EXAMPLE 14
7-Bromo-2,3-dioxo-1,2,3,4-tetrahydroquinoxalin-5-ylmethoxyacetic acid 1.14 g (3.81 mmol) of 7-bromo-5-hydroxymethyl-2,3-dimethoxy-quinoxaline, 840 ml (1.5 equiv.) of bromoacetic acid tert-butyl ester and 65 mg (0.05 equiv.) of tetrabutylammonium hydrogen sulfate are stirred in 40 ml of benzene and 4 ml of 50% sodium hydroxide solution for 18 hours. 100 ml of water and 100 ml of diethyl ether are added to the mixture, the organic phase is separated off and the aqueous phase is extracted once more with diethyl ether. The organic phases are combined, washed with brine, dried over magnesium sulfate and concentrated by evaporation. The residue is dissolved in 30 ml of acetic acid and 10 ml of 2N hydrochloric acid, is heated at reflux for 2 hours and cooled to 20° C. 200 ml of water are added, and the solid is filtered off, washed with water and dried.

$^1$H-NMR (250 MHz, DMSO-D$_6$) 12.0, 11.45 (2s, 2NH), 7.30, 7.28 (2d, 2H), 4.62 (s, 2H), 4.19 (s, 2H). MS: 328 (M$^+$) M.p.>250° C.

The starting material can be prepared, for example, as follows:
a) 7-Bromo-5-hydroxymethyl-2,3-dimethoxy-quinoxaline 11.5 g (31.85 mmol) of 7-bromo-5-bromomethyl-2,3-dimethoxy-quinoxaline are suspended at 20° C. in 100 ml of dioxane. 16.4 g (164 mmol) of calcium carbonate in 100 ml of water are then added and the mixture is heated at reflux for 24 hours. The dioxane is concentrated by evaporation and 300 ml of dichloromethane are added. The salt is filtered off, the organic phase is washed with brine and concentrated by evaporation and the residue is chromatographed on silica gel with ethyl acetate and hexane (1:1).

$^1$H-NMR (250 MHz, DMSO-D$_6$) 7.78, 7.68 (2d, 2H), 5.40 (t, OH), 4.96 (d, 2H), 4.02 (s, 2Me).

EXAMPLE 15
7-Bromo-2,3-dioxo-5-hydroxymethyl-1,2,3,4-tetrahydroquinoxaline 450 mg (1.5 mmol) of 7-bromo-5-hydroxymethyl-2,3-dimethoxy-quinoxaline are dissolved in 30 ml of acetic acid and 10 ml of 2N hydrochloric acid, and the solution is heated at reflux for 2 hours and cooled to 20° C. The solid is filtered off, washed with water and dried.

$^1$H-NMR (250 MHz, DMSO-D$_6$) 7.28, 7.19 (2d, 2H), 5.5 (br, OH), 4.62 (s, 2H). MS: 270 (M$^+$). M.p.>250° C.

EXAMPLE 16
7-Bromo-2,3-dioxo-1,2,3,4-tetrahydroquinoxalin-5-ylmethoxvacetic acid ethyl ester 450 mg (1.37 mmol) of 7-bromo-2,3-dioxo-1,2,3,4-tetrahydroquinoxalin-5-ylmethoxyacetic acid (Example 14) are suspended in 20 ml of ethanol. 0.5 ml of sulfuric acid is added and the mixture is heated at reflux, under nitrogen, for 2 hours. After cooling to 20° C., 80 ml of diethyl ether are added and the solid is filtered off, washed with diethyl ether and dried.

$^1$H-NMR (250 MHz, DMSO-D$_6$) 12.0, 11.1 (2s, 2NH), 7.28, 7.26 (2d, 2H), 4.63 (s, 2H), 4.23 (s, 2H), 4.20 (q, 2H), 1.22 (t, 3H). MS: 356 (M$^+$). M.p.=250–252° C.

EXAMPLE 17
(7-Bromo-2,3-dioxo-1,2,3,4-tetrahydroquinoxalin-5-ylmethoxy)-N-phenyl-acetamide The title compound is prepared in a manner analogous to that described under Example 7 but starting from 7-bromo-2,3-dioxo-1,2,3,4-tetrahydroquinoxalin-5-ylmethoxyacetic acid instead of N-(7-bromo-2,4-dioxo-1,2,3,4-tetrahydroquinoxalin-5-ylmethyl)-piperidine-3-carboxylic acid hydrobromide. M.p.>250° C.

EXAMPLE 18
7-Bromo-2,3-dioxo-1,2,3,4-tetrahydroquinoxalin-5-ylmethylsulfanylacetic acid ethyl ester 1.5 ml (4 mmol) of a 21% solution of sodium ethanolate in ethanol are diluted with 10 ml of ethanol under nitrogen. 601 mg (5 mmol) of thioglycolic acid ethyl ester are added at 0° C. and the mixture is heated to 20° C. After one hour, 1.09 g (3 mmol) of 7-bromo-5-bromomethyl-2,3-dimethoxy-quinoxaline, 10 ml of ethanol and 10 ml of tetrahydrofuran are added. The mixture is stirred for 18 hours, acidified with 2 ml of 2N hydrochloric acid and concentrated by evaporation. The residue is extracted with ethyl acetate and 0.1N hydrochloric acid, and the combined organic phases are washed with 10% sodium carbonate solution and brine, dried over magnesium sulfate and concentrated by evaporation. The residue is dissolved in 20 ml of a 33% solution of hydrogen bromide in acetic acid, and the solution is heated at 130° C. for 20 minutes and cooled to approximately 80° C. 20 ml of ethanol are added with stirring and the solution is left to stand at 5° C. for 18 hours. The crystals are filtered off, washed with cold ethanol and dried.

¹H-NMR (250 MHz, DMSO-D₆) 12.02, 11.42 (2s, 2NH), 7.22, 7.15 (2d, 2H), 4.0 (m, 4H), 3.22 (s, 2H), 1.18 (t, Me). MS: 372 (M⁺). M.p.=251–253° C.

EXAMPLE 19

7-Bromo-2,3-dioxo-1,2,3,4-tetrahydroquinoxalin-5-ylmethylsulfanylacetic acid 500 mg (1.34 mmol) of 7-bromo-2,3-dioxo-1,2,3,4-tetrahydroquinoxalin-5-ylmethylsulfanylacetic acid ethyl ester (Example 18) are suspended in 20 ml of tetrahydrofuran and 10 ml of water, and 225 mg (4 equiv.) of lithium hydroxide hydrate are added. The mixture is stirred at 20° C. for 48 hours. The tetrahydrofuran is concentrated by evaporation, 60 ml of water are added and the solution is acidified with 1 N hydrochloric acid. The solid is filtered off, washed with water and dried.

¹H-NMR (250 MHz, DMSO-D₆) 12.7 (br, COOH), 12.03, 11.48 (2s, 2NH), 7.22, 7.18 (2d, 2H), 3.98 (s, 2H), 3.17 (s, 2H). MS: 344 (M⁺). M.p.>250° C.

EXAMPLE 20

(7-Bromo-2,3-dioxo-1,2,3,4-tetrahydroquinoxalin-5-ylmethylsulfanyl)-N-phenylacetamide The title compound is prepared in a manner analogous to that described under Example 7 but starting from (7-bromo-2,3-dioxo-1,2,3,4-tetrahydroquinoxalin-5-ylmethylsulfanyl)-acetic acid instead of N-(7-bromo-2,4-dioxo-1,2,3,4-tetrahydroquinoxalin-5-ylmethyl)-piperidine-3carboxylic acid.

¹H-NMR (250 MHz, DMSO-D6) 12.02, 11.52 (2s, 2NH), 10.1 (s, NH), 7.58 (d, 2H), 7.32 (m, 2H), 7.28, 7.20 (2d, 2H), 7.08 (t, 1H), 4.05 (s, 2H), 3.22 (s, 2H). MS: 419 (M⁺). M.p.>250° C.

EXAMPLE 21

2-Amino-3-(7-bromo-2,3-dioxo-1,2,3,4-tetrahydroquinoxalin-5-yl)-propionic acid ethyl ester hydrobromide 1.55 g (3.26 mmol) of 2-amino-3-(7-bromo-2,3-dimethoxy-quinoxalin-5-yl)-propionic acid ethyl ester hemi-oxalate are dissolved in a 33% solution of HBr in acetic acid and the solution is heated at 130° C. for one hour. The mixture is cooled to 20° C. and diluted with diethyl ether. The solid is filtered off and washed with diethyl ether. After drying, the title compound is obtained in the form of a white powder.

¹H-NMR (DMSO-D6) δ=12.1 (s, NH), 8.35 (br), 7.25, 7.20 (2d, 2H), 4.20–4.03 (m, 3H), 3.25 (m, 2H), 1.10 (t, 3H); MS (FAB): 356 (M+H⁺). M.p.>280° C.

The starting material can be prepared, for example, as follows:

a) 2-Amino-3-(7-bromo-2.3-dimethoxy-quinoxalin-5-yl)-propionic acid ethyl ester hemi-oxalate 2.49 g (18 mmol) of potassium carbonate and 1.6 g (6 mmol) of N-benzhydrylidene-glycine ethyl ester are added at room temperature under nitrogen to a suspension of 1.81 g (5 mmol) of 7-bromo-5-bromomethyl-2,3-dimethoxy-quinoxaline and 193 mg (0.6 equiv.) of tetra-n-butylammonium bromide in 10 ml of acetonitrile. The reaction mixture is stirred under reflux for 20 hours and then cooled to room temperature. The solid is filtered off and washed with acetonitrile, the solvent is concentrated by evaporation and the residue is dissolved with 1.35 g (15 mmol) of oxalic acid in 25 ml of acetone and 1 ml of water.

The solution is stirred at room temperature for 18 hours, and the solid is filtered off, washed with acetone, suspended in 100 ml of water and stirred for ten minutes. The solid is filtered off again, washed with water and acetone and dried.

¹H-NMR (DMSO-D₆) δ=7.87, 7.58 (2d, 2H), 4.33 (t, 1H), 4.08, 4.03 (2s, 2Me), 3.98 (q, 2H), 3.61, 3.47 (2dd, 2H), 0.94 (t, 3H).

EXAMPLE 22

2-Amino-3-(7-bromo-2,3-dioxo-1,2,3,4-tetrahydroquinoxalin-5-yl)-propionic acid hydrochloride 368 mg (5 equiv.) of lithium hydroxide hydrate are added to 767 mg (1.75 mmol) of 2-amino-3-(7-bromo-2,3-dioxo-1,2,3,4tetrahydroquinoxalin-5-yl)-propionic acid ethyl ester hydrobromide (Example 21) in 60 ml of tetrahydrofuran/water (2:1). The reaction mixture is stirred at room temperature for 72 hours. The tetrahydrofuran is concentrated by evaporation and the solution is acidified with 1 N hydrochloric acid. The solid is filtered off, washed with water and dried.

¹H-NMR (D₂O+NaOD) δ=6.88, 6.66 (2d, 2H), 3.19, 2.92, 2.45 (3dd, 3H); MS (FD): 327 (M⁺). M.p.>250° C.

EXAMPLE 23

N-(7-Bromo-2,3-dioxo-1,2,3,4-tetrahydroquinoxalin-5-ylmethyl)-oxalamic acid ethyl ester 254 mg (0.79 mmol) of N-(7-bromo-2,3-dimethoxyquinoxalin-5-ylmethyl)-oxalamic acid ethyl ester are dissolved in 6 ml of an approximately 25% solution of hydrogen bromide in acetic acid, and the solution is stirred at room temperature for 16 hours. The mixture is diluted with diethyl ether, and the solid is filtered off and washed with diethyl ether. After drying under a high vacuum, the title compound is obtained in the form of a beige solid.

¹H-NMR (250 MHz, DMSO-D₆+5% D₂O) δ=7.24, 7.19 (2d, 2H), 4.40 (s, 2H), 4.23 (q, 2H), 1.27 (t, 3H). M.p.=192° C. (decomp.).

The starting material can be prepared, for example, as follows:

a) N-(7-Bromo-2,3-dimethoxy-quinoxalin-5-ylmethyl)-oxalamic acid ethyl ester 300 mg (1 mmol) of 5-aminomethyl-7-bromo-2,3-dimethoxyquinoxaline hydrochloride are suspended in 10 ml of THF and the suspension is cooled to 0° C. 0.183 ml (1.3 equiv.) of triethylamine is added and then 0.123 ml (1.1 equiv.) of oxalic acid monoethyl ester chloride is added dropwise in the course of 30 minutes. The mixture is stirred at 0° C. for 2 hours, then at 20° C. for 16 hours and is concentrated by evaporation. The residue is stirred in diethyl ether, and the solid is filtered off, washed with water and diethyl ether and dried.

¹H-NMR (250 MHZ, CDCl₃) δ=8.12 (t, NH), 7.90, 7.58 (2d, 2H), 4.81 (d, 2H), 4.32 (q, 2H), 4.19, 4.14 (2s, 2Me), 1.38 (t, 3H).

EXAMPLE 24

N-(7-Bromo-2,3-dioxo-1,2,3,4-tetrahydroquinoxalin-5-ylmethyl)-malonamic acid methyl ester The title compound is prepared in a manner analogous to that described under Example 23. M.p.>300° C.

EXAMPLE 25

N-(7-Bromo-2,3-dioxo-1,2,3,4-tetrahydroquinoxalin-5-ylmethyl)-oxalamic acid

The title compound is prepared in a manner analogous to that described under Example 21 starting from N-(7-bromo- 2,3-dimethoxy-quinoxalin-5-ylmethyl)-oxalamic acid. M.p.=265° C. (decomp.).

The starting material can be prepared, for example, as follows:

a) N-(7-Bromo-2,3-dimethoxyquinoxalin-5-ylmethyl)-oxalamic acid 276 mg of N-(7-bromo-2,3-dimethoxy-quinoxalin-5-ylmethyl)-oxalamic acid ethyl ester and 150 mg of potassium carbonate are suspended in 2 ml of water and 5 ml of methanol. The mixture is stirred for 20 hours and acidified with 1 N HCl, and the solid is filtered off and washed with methanol and diethyl ether. M.p.>300° C.

EXAMPLE 26

N-(7-Bromo-2,3-dioxo-1,2,3,4-tetrahydroquinoxalin-5-ylmethyl)-malonamic acid

The title compound is prepared in a manner analogous to that described under Example 25. M.p.>300° C.

EXAMPLE 27

Furan-2-carboxylic acid (7-bromo-2,3-dioxo-1,2,3,4-tetrahydroquinoxalin-5-ylmethyl)-amide 310 mg (0.79 mmol) of furan-2-carboxylic acid (7-bromo-2,3-dimethoxy-quinoxalin-5-ylmethyl)-amide are dissolved in 6 ml of an approximately 25% solution of hydrogen bromide in acetic acid, and the solution is stirred at room temperature for 16 hours. The mixture is diluted with diethyl ether, and the solid is filtered off and washed with diethyl ether. After drying under a high vacuum, the title compound is obtained in the form of a beige solid.

$^1$H-NMR (250 MHz, DMSO-D$_6$) δ=12.01, 11.42 (2s, 2NH), 9.12 (t, NH), 7.91 (d, 1H), 7.22 (m, 3H), 6.68 (t, 1H), 4.50 (d, 2H). MS (FAB): 364 (M$^+$). M.p.=216° C. (decomp.).

The starting material can be prepared, for example, as follows:

a) Furan-2-carboxylic acid (7-bromo-2,3-dimethoxy-quinoxalin-5-ylmethyl)-amide 300 mg (1 mmol) of 5-aminomethyl-7-bromo-2,3-dimethoxy-quinoxaline hydrochloride, 124 mg (1.1 equiv.) of furan-2-carboxylic acid, 212 mg (1.1 equiv.) of N-(3-dimethylaminopropyl)-N'-ethyl-carbodiimide hydrochloride and 12.2 mg (0.1 equiv.) of 4-dimethylamino-pyridine are stirred in dried THF at 20° C. for 20 hours. The mixture is poured onto water, and the solid is filtered off and washed with water and diethyl ether. After drying under a high vacuum, the title compound is obtained in the form of a beige solid.

$^1$H-NMR (250 MHz, CDCl$_3$) δ=7.89 (d, 1H), 7.62 (d, 1H), 7.40 (d, 1H), 7.29 (t, NH), 7.13 (d, 1H), 6.49 (t, 1H), 5.01 (d, 2H), 4.20, 4.14 (2s, 2Me).

EXAMPLE 28

The following compounds are also prepared in a manner analogous to that described under Example 23 or 27:

cyclopropanecarboxylic acid (7-bromo-2,3-dioxo-1,2,3,4-tetrahydroquinoxalin-5-ylmethyl)-amide, m.p.=250° C. (decomp.);

2-amino-N-(7-bromo-2,3-dioxo-1,2,3,4-tetrahydroquinoxalin-5-ylmethyl)-acetamide hydrobromide, m.p.=293° C. (decomp.);

N-(7-bromo-2,3-dioxo-1,2,3,4-tetrahydroquinoxalin-5-ylmethyl)-3,5-bistrifluoromethyl-benzamide, m.p.>300° C.;

N-(7-bromo-2,3-dioxo-1,2,3,4-tetrahydroquinoxalin-5-ylmethyl)-benzamide, m.p.=210° C. (decomp.).

EXAMPLE 29

N-(7-Bromo-2,3-dioxo-1,2,3,4-tetrahydroquinoxalin-5-ylmethyl)-acetamide 50 mg (0.19 mmol) of 5-aminomethyl-7-bromo-2,3-dioxo-1,2,3,4-tetrahydroquinoxaline hydrochloride are suspended in 4 ml of N,N-dimethylformamide and stirred at 20° C. for 24 hours with 0.02 ml (1.2 equiv.) of acetic anhydride and 0.059 ml (2.2 equiv.) of triethylamine. The solvent is concentrated by evaporation, and the solid is suspended in diethyl ether, filtered off and washed with methanol and diethyl ether. After drying under a high vacuum, the title compound is obtained in the form of a white solid.

$^1$H-NMR (250 MHz, DMSO-D$_6$) δ=12.02, 11.48 (2NH), 8.65 (t, NH), 7.22, 7.18 (2d, 2H), 4.35 (d, 2H), 1.93 (s, Me). MS (ESP) 310 (M$^+$–1). M.p.>300° C.

EXAMPLE 30

The following compound is also prepared in a manner analogous to that described under Example 29:

N-(7-bromo-2,3-dioxo-1,2,3,4-tetrahydroquinoxalin-5-ylmethyl)-trifluoroacetamide, m.p.>300° C.

EXAMPLE 31

The following can also be prepared in a manner analogous to that described in Examples 1 to 29:

N-(2,3-dioxo-7-nitro-1,2,3,4-tetrahydroquinoxalin-5-ylmethyl)-(L)-tyrosine hydrobromide, m.p.=264° C. (decomp.);

N-(2,3-dioxo-7-nitro-1,2,3,4-tetrahydroquinoxalin-5-ylmethyl)-tert-leucine hydrobromide, m.p.=208° C. (decomp.);

N-(2,3-dioxo-7-nitro-1,2,3,4-tetrahydroquinoxalin-5-ylmethyl)-(L)-proline hydrobromide, m.p.=279° C. (decomp.);

N-(2,3-dioxo-7-nitro-1,2,3,4-tetrahydroquinoxalin-5-ylmethyl)-(L)-alanine hydrobromide, m.p.=229° C. (decomp.);

N-(2,3-dioxo-7-nitro-1,2,3,4-tetrahydroquinoxalin-5-ylmethyl)-(D)-alanine hydrobromide, m.p.=228° C. (decomp.);

N-(2,3-dioxo-7-nitro-1,2,3,4-tetrahydroquinoxalin-5-ylmethyl)-sarcosine hydrobromide, m.p.=280° C. (decomp.);

N-(2,3-dioxo-7-nitro-1,2,3,4-tetrahydroquinoxalin-5-ylmethyl)-(L)-valine hydrobromide, m.p.=226° C. (decomp.);

N-(2,3-dioxo-7-nitro-1,2,3,4-tetrahydroquinoxalin-5-ylmethyl)-oxalamic acid methyl ester;

N-(2,3-dioxo-7-nitro-1,2,3,4-tetrahydroquinoxalin-5-ylmethyl)-oxalamic acid, m.p.=255° C. (decomp.);

4-[(7-bromo-2,3-dioxo-1,2,3,4-tetrahydroquinoxalin-5-ylmethyl)-carbamoyl]-butyric acid methyl ester, m.p.>250° C. (decomp.);

N-(2,3-dioxo-7-nitro-1,2,3,4-tetrahydroquinoxalin-5-ylmethyl)-N-benzyl-glycine ethyl ester hydrobromide, and N-(2,3-dioxo-7-nitro-1,2,3,4-tetrahydroquinoxalin-5-ylmethyl)-N-benzyl-glycine hydrochloride, m.p.=205° C. (decomp.).

EXAMPLE 32

N-(2,3-Dioxo-7-nitro-1,2,3,4-tetrahydroquinoxalin-5-ylmethyl)-acetamide 103 mg (0.34 mmol) of N-(2,3-dimethoxy-7-nitro-quinoxalin-5-ylmethyl)-acetamide are stirred in 3 ml of a 25% solution of hydrogen bromide in acetic acid for 24 hours at 50° C. The reaction mixture is diluted with diethyl ether, and the solid is filtered off, washed with diethyl ether and dried. M.p.=269–272° C. (decomp.).

The starting material can be prepared, for example, as follows:

a) N-(2,3-Dimethoxy-7-nitro-quinoxalin-5-ylmethyl)-acetamide 111 mg (0.437 mmol) of 5-aminomethyl-2,3-dimethoxy-7-nitro-quinoxaline, obtainable in a manner analogous to that described in Example 9 but starting from 5-bromomethyl-2,3-dimethoxy-7-nitro-quinoxaline, are stirred with 0.046 ml (1.1 equiv.) of acetic anhydride and 0.073 ml (1.2 equiv.) of triethylamine in 5 ml of N,N-diethylformamide at room temperature for 24 hours. The reaction mixture is diluted with diethyl ether, and the solid is filtered off, washed with diethyl ether and dried.

$^1$H-NMR (DMSO-$D_6$, 250 MHz): 8.52 (t, NH), 8.42, 8.16 (2d, 2H), 4.79 (d, 2H), 4.15, 4.12 (2s, 2Me), 1.98 (s, Me).

EXAMPLE 33

The following can also be prepared in a manner analogous to that described in Examples 21 to 32:

N-(7-bromo-2,3-dioxo-1,2,3,4-tetrahydroquinoxalin-5-ylmethyl)-phenylacetamide, m.p.>250°°C.;

N-(7-bromo-2,3-dioxo-1,2,3,4-tetrahydroquinoxalin-5-ylmethyl)-3-phenyl-propionamide, m.p.=237° C.;

N-(7-bromo-2,3-dioxo-1,2,3,4-tetrahydroquinoxalin-5-ylmethyl)-thiophene-2-carboxylic acid amide, m.p.>250° C.;

N-(7-bromo-2,3-dioxo-1,2,3,4-tetrahydroquinoxalin-5-ylmethyl)-3-thienyl-acetamide, m.p.>260° C.; and N-(7-bromo-2,3-dioxo-1,2,3,4-tetrahydroquinoxalin-5-ylmethyl)-3-methoxyphenylacetamide, m.p.>250° C.

EXAMPLE 34

N-(2,3-Dioxo-7-nitro-1,2,3,4-tetrahydroquinoxalin-5-ylmethyl)-N-methylbenzylamine hydrobromide 213 mg (0.53 mmol) of N-(2,3-dimethoxy-7-nitro-quinoxalin-5-ylmethyl)-N-methylbenzylamine are dissolved in 4 ml of an approximately 25% solution of hydrogen bromide in acetic acid, and the solution is stirred at room temperature for 20 hours. The mixture is diluted with diethyl ether and then stirred for 10 minutes, and the solid is filtered off and washed with diethyl ether and a small amount of water. After drying under a high vacuum, the title compound is obtained in the form of a beige solid.

$^1$H-NMR (DMSO-$D_6$, 250 MHz): 12.17,11.8 (2s, 2NH), 9.7 (brs, NH), 7.52 (m, Ph+H), 7.38 (d, H), 4.8-4.15 (m, 4H), 2.5 (s, Me); MS(El): 373 (M$^+$). M.p.=208–212° C. (decomp.).

Alternatively, the title compound can be prepared as follows:

213 mg (0.53 mmol) of N-(2,3-dimethoxy-7-nitro-quinoxalin-5-ylmethyl)-N-methylbenzylamine are heated at reflux in 10 ml of 2N aqueous hydrochloric acid for 18 hours. The reaction mixture is concentrated by evaporation, and the solid is suspended in diethyl ether and a small amount of water, filtered off and dried. The desired compound is obtained in the form of a beige solid.

The starting material can be prepared, for example, as follows:

a) N-2,3-Dimethoxy-7-nitro-quinoxalin-5-ylmethyl)-N-methyl-benzylamine 200 mg of 5-bromomethyl-2,3-dimethoxy-7-nitro-quinoxaline and 0.016 ml (2.2 equiv.) of N-benzyl-methylamine are dissolved in 10 ml of acetonitrile, and the solution is stirred at reflux for 20 hours. The mixture is concentrated by evaporation, and the residue is dissolved in ethyl acetate and washed in aqueous 5% sodium carbonate solution and brine. The organic phase is dried over magnesium sulfate and the solvent is concentrated by evaporation.

$^1$H-NMR (CDCl$_3$, 250 MHz): 7.84, 7.78 (2d, 2H), 7.4–7.2 (m, Ph), 4.13, 4.08 (2s, 2Me), 4.03, 3.65 (2s, 2CH$_2$), 2.26 (s, Me).

EXAMPLE 35

The following compounds are also prepared in a manner analogous to that described under Example 34:

N-(7-bromo-2,3-dioxo-1,2,3,4-tetrahydroquinoxalin-5-ylmethyl)-furfurylamine hydrobromide, m.p.=282° C. (decomp.);

N-(2,3-dioxo-7-nitro-1,2,3,4-tetrahydroquinoxalin-5-ylmethyl)-2-morpholino-ethylamine hydrobromide, m.p.=228° C. (decomp.);

N-(2,3-dioxo-7-nitro-1,2,3,4-tetrahydroquinoxalin-5-ylmethyl)-diethylamine hydrobromide, m.p.=290° C. (decomp.);

N-(2,3-dioxo-7-nitro-1,2,3,4-tetrahydroquinoxalin-5-ylmethyl)-dimethylamine hydrobromide, m.p.=325° C. (decomp.);

N-(2,3-dioxo-7-nitro-1,2,3,4-tetrahydroquinoxalin-5-ylmethyl)-2-(2-pyddyl)-ethyl-methylamine dihydrobromide, m.p.=205° C. (decomp.);

N-(2,3-dioxo-7-nitro-1,2,3,4-tetrahydroquinoxalin-5-ylmethyl)-cyclopropylamine hydrobromide, m.p.=268° C. (decomp.);

N-(2,3-dioxo-7-nitro-1,2,3,4-tetrahydroquinoxalin-5-ylmethyl)-diethanolamine hydrochloride, m.p.=251° C. (decomp.);

N-(2,3-dioxo-7-nitro-1,2,3,4-tetrahydroquinoxalin-5-ylmethyl)-2-amino-2-thiazoline hydrobromide, m.p.=271° C. (decomp.);

N-(2,3-dioxo-7-nitro-1,2,3,4-tetrahydroquinoxalin-5-ylmethyl)-2-aminopyrazine dihydrobromide, m.p.=183° C. (decomp.);

N-(2,3-dioxo-7-nitro-1,2,3,4-tetrahydroquinoxalin-5-ylmethyl)-2-aminothiazole hydrobromide, m.p.=153° C. (decomp.);

N-(2,3-dioxo-7-nitro-1,2,3,4-tetrahydroquinoxalin-5-ylmethyl)-aniline hydrobromide, m.p.>250° C.;

N-(2,3-dioxo-7-nitro-1,2,3,$^4$-tetrahydroquinoxalin-5-ylmethyl)-4-fluoroaniline hydrobromide, m.p.=218° C. (decomp.);

N-(2,3-dioxo-7-nitro-1,2,3,4-tetrahydroquinoxalin-5-ylmethyl)-3-fluoroaniline hydrobromide, m.p.>250° C.;

N-(2,3-dioxo-7-nitro-1,2,3,4-tetrahydroquinoxalin-5-ylmethyl)-2-fluoroaniline hydrobromide, m.p.=222–235° C.;

[N-(2,3-dioxo-7-nitro-1,2,3,4-tetrahydroquinoxalin-5-ylmethyl)-2-amino-4-thiazolyl]-acetic acid ethyl ester hydrobromide, m.p.=258° C. (decomp.); and

[N-(7-bromo-2,3-dioxo-1,2,3,4-tetrahydroquinoxalin-5-ylmethyl)-2-amino-4-thiazolyl]-acetic acid ethyl ester hydrobromide, MS(El): 438 (M$^+$).

EXAMPLE 36

[N-(2,3-Dioxo-7-nitro-1,2,3,4-tetrahydroquinoxalin-5-ylmethyl)-2-amino-4-thiazolyl]-acetic acid hydrochloride 80 mg (0.2 mmol) of [N-(2,3-dioxo-7-nitro-1,2,3,4-tetrahydroquinoxalin-5-ylmethyl)-2-amino-4-thiazolyl]-acetic acid ethyl ester hydrobromide are stirred in 2 ml of 2N sodium hydroxide solution at room temperature for 16 hours. The mixture is acidified with 3N HCl, and the resulting solid is filtered off and washed with a small amount of water and 2×20 ml of diethyl ether. After drying, the title compound is obtained in the form of a yellow solid.

$^1$H-NMR (DMSO-D$_6$, 250 MHz): 12.4, 12.3 (2s, 2NH), 9.0 (s, NH), 8.09, 8.02 (2d, 2H), 6.75 (s, H), 4.8 (br s, 2H), 3.7 (s, 2H); m.p.=284° C. (decomp.).

EXAMPLE 37

N-(2,3-Dioxo-7-nitro-1,2,3,4-tetrahydroquinoxalin-5-ylmethyl)-N-(2-pyridylmethyl)-glycine dihydrobromide 49 mg (0.1 mmol) of N-(2,3-dimethoxy-7-nitro-quinoxalin-5-ylmethyl)-N-(2-pyridylmethyl)-glycine dihydrochloride are stirred in 2 ml of a 48% solution of hydrogen bromide in acetic acid for 18 hours at 70° C. The mixture is diluted with diethyl ether and the solid is filtered off, washed with diethyl ether and dried. The title compound is obtained in the form of a yellow solid.

$^1$H-NMR (DMSO-D$_6$, 250 MHz): 12.3 (s, 2NH), 8.8, 8.25, 7.72, 7.68 (4m, Py), 7.92, 7.89 (2d, 2H), 4.1 (m, 2H), 3.6 (s, 2H); MS(FAB+) 386 (M+H); m.p.>280° C.

The starting material can be prepared, for example, as follows:

a) N-(2,3-Dimethoxy-7-nitro-quinoxalin-5-ylmethyl)-N-(2-pyridylmethyl)-glycine ethyl ester 150 ml (0.46 mmol) of 5-bromomethyl-2,3-dimethoxy-7-nitro-quinoxaline, 98 mg (1.1 equiv.) of N-(2-pyridylmethyl)-glycine ethyl ester and 0.076 ml (1.2 equiv.) of triethylamine are stirred at reflux in 5 ml of acetonitrile for 20 hours. The mixture is concentrated by evaporation and the residue is suspended in diethyl ether and filtered. After drying, the title compound is obtained in the form of a white powder.

$^1$H-NMR (DMSO-D$_6$, 250 MHz): 8.45, 8.37 (2d, 2H), 8.45, 7.72, 7.43, 7.22 (4m, Py), 4.39 (s, 2H), 4.05 (m, 2Me+2H), 4.0 (s, 2H), 3.53 (s, 2H), 1.18 (t, Me).

b) N-(2,3-Dimethoxy-7-nitro-quinoxalin-5-ylmethyl)-N-(2-pyridylmethyl)-glycine dihydrochloride 80 mg (0.186 mmol) of N-(2,3-dimethoxy-7-nitro-quinoxalin-5-ylmethyl)-N-(2-pyridylmethyl)-glycine ethyl ester and 51 mg (2 equiv.) of potassium carbonate are stirred in 5 ml of methanol and 2 ml of water for 20 hours at room temperature. The mixture is concentrated, acidified with 2N HCl and concentrated by evaporation. The residue is recrystallized from hot ethyl acetate, filtered off, washed with water and diethyl ether and dried.

EXAMPLE 38

N-(2,3-Dioxo-7-nitro-1,2,3,4-tetrahydroquinoxalin-5-ylmethyl)-3-amino-benzoic acid hydrobromide 60 mg (0.156 mmol) of N-[2,3-dimethoxy-7-nitro-quinoxalin-5-ylmethyl]-3-aminobenzoic acid are stirred in 4 ml of approximately 24% HBr in acetic acid for 20 hours at 20° C. The reaction mixture is diluted with diethyl ether and the solid is filtered off and washed with diethyl ether. M.p.=275° C. (decomp.).

The starting material can be prepared, for example, as follows:

a) N-[2,3-Dimethoxy-7-nitro-quinoxalin-5-ylmethyl]-3-amino-benzoic acid 350 mg (1.06 mmol) of 5-bromomethyl-2,3-dimethoxy-7-nitro-quinoxaline, 153 mg (1.05 equiv.) of 3-aminobenzoic acid and 0.165 ml (1.1 equiv.) of triethylamine are combined in 10 ml of acetonitrile, and heated at boiling at reflux for 24 hours. The reacton mixture is concentrated by evaporation, extracted with ethyl acetate and 1 N HCl and washed once with brine. The organic phases are combined, dried over magnesium sulfate and concentrated by evaporation.

$^1$H-NMR (CDCl$_3$, 250 MHz) 8.50, 8.27 (2d, 2H), 7.32, 7.15, 7.10, 6.75 (4m, 4H), 4.85 (s. 2H), 4.13, 4.12 (2s, 2Me).

EXAMPLE 39

N-(2,3-Dioxo-7-nitro-1,2,3,4-tetrahydroquinoxalin-5-ylmethyl)-2-methylaziridine hydrobromide 180 mg (0.59 mmol) of N-(2,3-dimethoxy-7-nitro-quinoxalin-5-ylmethyl)-2-methylaziridine are stirred in a 33% solution of hydrogen bromide in acetic acid for 2 hours at 70° C. The mixture is diluted with diethyl ether and the solid is filtered off and washed with diethyl ether. After drying, the title compound is obtained in the form of a yellow solid. M.p.=241° C. (decomp.).

The starting material can be prepared, for example, as follows:

a) N-(2,3-Dimethoxy-7-nitro-quinoxalin-5-ylmethyl)-2-methylaziridine 200 mg (0.61 mmol) of 5-bromomethyl-2,3-dimethoxy-7-nitro-quinoxaline, 0.086 ml (2 equiv.) of propyleneimine and 0.295 ml (0.3 equiv.) of an aqueous 40% tetrabutylammonium hydroxide solution are stirred in 8 ml of dichloromethane for 20 hours at room temperature. The mixture is concentrated by evaporation and the residue is extracted with ethyl acetate and a 5% sodium carbonate solution. The combined organic phases are washed once with brine, dried over magnesium sulfate and concentrated by evaporation.

$^1$H-NMR (CDCl$_3$, 250 MHz): 8.6 (m, 2H), 4.18 (m, 2Me+H), 3.95 (s, 2H), 3.38 (m, 2H), 1.0 (t, Me).

EXAMPLE 40

N-(2,3-Dioxo-7-nitro-1,2,3,4-tetrahydroguinoxalin-5:ylmethyl)-azetidine hydrobromide, m.p.=265° C. (decomp.), can be prepared in a manner analogous to that described under Example 39.

EXAMPLE 41

N-(2,3-Dioxo-7-nitro-1,2,3,4-tetrahydroquinoxalin-5-ylmethyl)-4-methylpiperidine hydrobromide The title compound can be prepared as described under Example 39 but starting from N-(2,3-dimethoxy-7-nitro-quinoxalin-5-ylmethyl)-4-methylpiperidine instead of N-(2,3-dimethoxy-7-nitro-quinoxalin-5-ylmethyl)-2-methylazirdine. M.p.=296° C. (decomp.).

The starting material can be prepared, for example, as follows:

a) N-2,3-Dimethox-7-nitro-quinoxalin-5-ylmethyl)-4-methylpiperdine 100 mg (0.304 mmol) of 5-bromomethyl-2,3-dimethoxy-7-nitro-quinoxaline, 0.04 ml (1.1 equiv.) of 4-methyl-piperidine and 0.05 ml (1.2 equiv.) of triethylamine are stirred at reflux for 20 hours. The mixture is concentrated by evaporation and the residue is extracted with ethyl acetate and a 5% sodium carbonate solution. The combined organic phases are dried over magnesium sulfate and concentrated by evaporation.

$^1$H-NMR (CDCl$_3$, 250 MHz): 8.58, 8.43 (m, 2H), 4.19, 4.17 (2s, 2Me), 4.06 (s, 2H), 2.97, 2.15, 1.62, 1.40-1.25 (4m, 9H), 0.93 (d, Me).

EXAMPLE 42

The following compounds can also be prepared in a manner analogous to that described under Examples 1 to 41:

N-(2,3-dioxo-7-nitro-1,2,3,4-tetrahydroquinoxalin-5-ylmethyl)-N'-(4-methoxyphenyl)-piperazine hydrobromide, m.p.=241° C. (decomp.);

N-(2,3-dioxo-7-nitro-1,2,3,4-tetrahydroquinoxalin-5-ylmethyl)-piperidine hydrobromide, m.p.>300° C.;

N-(2,3-dioxo-7-nitro-1,2,3,4-tetrahydroquinoxalin-5-ylmethyl)-2,6-dimethylpiperidine hydrobromide, m.p.=277° C. (decomp.);

N-(2,3-dioxo-7-nitro-1,2,3,$^4$-tetrahydroquinoxalin-5-ylmethyl)-pyrrolidine hydrobromide, m.p.>300° C.;

N-(2,3-dioxo-7-nitro-1,2,3,4-tetrahydroquinoxalin-5-ylmethyl)-4-piperidone hydrobromide, m.p.=259° C. (decomp.);

N-(2,3-dioxo-7-nitro-1,2,3,4-tetrahydroquinoxalin-5-ylmethyl)-hexamethyleneimine hydrobromide, m.p.= 298° C. (decomp.);

N-(2,3-dioxo-7-nitro-1,2,3,4-tetrahydroquinoxalin-5-ylmethyl)-3-pyrroline hydrobromide, m.p.>300° C.;

N-(2,3-dioxo-7-nitro-1,2,3,4-tetrahydroquinoxalin-5-ylmethyl)-thiomorpholine hydrobromide, m.p.=291 ° C. (decomp.);

N-(2,3-dioxo-7-nitro-1,2,3,4-tetrahydroquinoxalin-5-ylmethyl)-morpholine hydrobromide, m.p.>300° C.;

N-(2,3-dioxo-7-nitro-1,2,3,4-tetrahydroquinoxalin-5-ylmethyl)-thiazolidine hydrobromide, m.p.=250° C. (decomp.);

N-(2,3-dioxo-7-nitro-1,2,3,4-tetrahydroquinoxalin-5-ylmethyl)-3-pyrrolidinole hydrobromide, m.p.=286° C. (decomp.);

N-(2,3-dioxo-7-nitro-1,2,3,4-tetrahydroquinoxalin-5-ylmethyl)-N-methylpiperazine dihydrobromide, m.p.= 295° C. (decomp.);

N-(2,3-dioxo-7-nitro-1,2,3,4-tetrahydroquinoxalin-5-ylmethyl)-2-(2-hydroxyethyl)-piperidine hydrochloride, m.p.=298° C. (decomp.);

N-(2,3-dioxo-7-nitro-1,2,3,4-tetrahydroquinoxalin-5-ylmethyl)-piperazine dihydrobromide, m.p.>300° C.;

N-(2,3-dioxo-7-nitro-1,2,3,4-tetrahydroquinoxalin-5-ylmethyl)-3-azabicyclo[3.2.2]nonane hydrobromide, m.p.=271° C. (decomp.);

N-(2,3-dioxo-7-nitro-1,2,3,4-tetrahydroquinoxalin-5-ylmethyl)-tetrahydropyridine hydrobromide, m.p.=279° C. (decomp.);

N-(2,3-dioxo-7-nitro-1,2,3,4-tetrahydroquinoxalin-5-ylmethyl)-pyrazole hydrobromide, m.p.=298° C. (decomp.);

N-(2,3-dioxo-7-nitro-1,2,3,4-tetrahydroquinoxalin-5-ylmethyl)-3-ethoxycarbonyl-pyrazole hydrobromide, m.p.=195° C.;

[1-(2,3-dioxo-7-nitro-1,2,3,4-tetrahydroquinoxalin-5-ylmethyl)-1H-indol-3-yl]-acetic acid methyl ester hydrobromide, m.p.=230° C.; and N-(2,3-dioxo-7-nitro-1,2,3,4-tetrahydroquinoxalin-5-ylmethyl)-1,2,3,4-tetrahydroquinoline hydrobromide, m.p.=212–215° C.

EXAMPLE 43

N-(7-Bromo-2,3-dioxo-1,2,3,4-tetrahydroquinoxalin-5-ylmethyl)-methanesulfonic acid amide 83 mg (0.31 mmol) of 5-aminomethyl-7-bromo-2,3-dioxo-1,2,3,4-tetrahydroquinoxaline are suspended in 4 ml of DMF. 0.063 ml (1.6 equiv.) of triethylamine and 82 mg (1.4 equiv.) of methanesulfonic anhydride are added and the solution is stirred for 18 hours. The solvent is concentrated by evaporation and the residue is suspended in diethyl ether. The solid is filtered off, washed with water and diethyl ether and dried. The title compound is obtained in the form of a white powder. M.p.>300° C.

EXAMPLE 44

N-Methyl-2-phenylacetic acid (7-bromo-2,3-dioxo-1,2,3,4-tetrahydroquinoxalin-5-ylmethyl)-amide 2 ml of hydrochloric acid (2N in water) are added to a solution of 129 mg (0.3 mmol) of N-methyl-2-phenylacetic acid (7-bromo-2,3-dimethoxy-quino xalin-5-ylmethyl)-amide in 3 ml of THF, and the mixture is heated at boiling point under reflux for 16 hours. After cooling in an ice bath, the precipitate is filtered off and washed with cold water. Colorless crystals are formed from hot DMF overnight in a refrigerator and are filtered off and dried under a high vacuum.

$^1$H-NMR (300 MHz, DMSO-D$_6$) 12.05–11.95 (br.s, 1H), 11.51–11.33 (br.s, 1H), 7.38–7.10 (m, 7H), 4.78 (s, 0.2H), 4.59 (s, 1.8H), 3.82 (s, 1.8H), 3.62 (s, 0.2H), 2.99 (s, 2.7H), 2.82 (s, 0.3H). MS (FAB): 402 (M-), m.p.>260° C.

The starting material can be prepared, for example, as follows:

a) 2-Phenylacetic acid (7-bromo-2,3-dimethoxy-quinoxalin-5-ylmethyl)-amide can be prepared as described under Example 27.

b) N-Methyl-2-phenylacetic acid (7-bromo-2,3-dimethoxy-quinoxalin-5-ylmethyl)-amide A solution of 208 mg (0.5 mmol) of 2-phenylacetic acid (7-bromo-2,3-dimethoxy-quinoxalin-5-ylmethyl)-amide in 4 ml of THF (abs.) is added dropwise in the course of 15 minutes to a suspension of 30.5 mg (0.7 mmol) of sodium hydride suspension in 3 ml of absolute THF. After heating at boiling under reflux for 90 minutes, the mixture is cooled in an ice bath. After the addition of 85 mg (0.6 mmol) of methyl iodide, the suspension is stirred at 0° C. for 1 hour and at room temperature for a further 15 hours. 0.9 g of silica gel is added and the suspension is concentrated, dried and purified on a silica gel column using dichloromethane/hexane/diethyl ether (8:4:1) as eluant. After concentration and drying under a high vacuum, the title compound is obtained in the form of a virtually colorless honey which consists of the cis/trans isomeric mixture in a ratio of approximately 2:3.

$^1$H-NMR (300 MHz, CDCl$_3$) 7.87 (d, 1 Hz, 0.4H), 7.83 (d, 1 Hz, 0.6H), 7.4–7.15 (m, 6H), 5.10 (s, 1.2H), 5.00 (s, 0.8H), 4.15 (s, 1.2H), 4.12 (s, 1.8H), 4.09 (s, 3H), 3.82 (s, 1.2H), 3.75 (s, 0.8H), 3.03 (s, 1.2H), 2.98 (s, 1.8H).

EXAMPLE 45

N-(7-Bromo-2,3-dioxo-1,2,3,4-tetrahydroquinoxalin-5-ylmethyl)-α-amino-phosphonic acid Under a nitrogen atmosphere, 255 mg (0.607 mmol) of N-(7-bromo-2,3-dimethoxy-quinoxalin-5-ylmethyl)-α-aminophosphonic acid dimethyl ester are dissolved in 5 ml of absolute dichloromethane, and 0.33 ml (2.55 mmol) of trimethylsilyl bromide is added at room temperature. After 3 hours' stirring at room temperature, 5 ml of ethanol are added and stirring is continued at room temperature for a further 22 hours. The mixture is then concentrated to dryness. 5 ml of HBr (33% in glacial acetic acid) are added to the beige foam and the mixture is stirred at room temperature for 3 hours before being concentrated to dryness again. The beige residue is taken up in K$_2$CO$_3$ solution (approximately 1 N in water). The pH value is adjusted to 6 with dilute hydrochloric acid and the suspension is filtered while hot. There are added to the filtrate hot DMF and then a small amount of ethanol until the mixture becomes slightly cloudy. The title compound separates out in the form of beige crystals in the course of 3 days.

$^1$H-NMR (300 MHz, D$_2$O) 7.53 (br.s, 1H), 7.47 (br.s, 1H), 4.57 (br.s, 2H), 3.15 (d, 11.8 Hz, 2H); $^{31}$P-NMR 8 ppm; MS (FAB$^+$) 364, 366 [M+H$^+$]$^+$, (FAB$^-$) 362, 364 [M–H$^+$]$^-$; m.p.>270° C.

The starting materials can be prepared, for example, as follows:

a) Tri-N-(7-bromo-2,3-dimethoxy-quinoxalin-5-ylmethyl)-triazine 2.98 g (10 mmol) of (7-bromo-2,3-dimethoxy-quinoxalin-5-yimethyl)-amine are dissolved in 40 ml of ethanol by heating. After cooling to room temperature, 1 ml of formalin solution (37% in water) is added dropwise to the light-yellow solution. When the addition is complete, the product settles out in the form of a colorless precipitate. After 3 hours' stirring, the precipitate is filtered off. After drying under a high vacuum, the title compound is obtained in the form of a colorless amorphous crystalline mass.

$^1$H-NMR (300 MHz, CDCl$_3$) 7.83 (d, 2.3 Hz, 3H), 7.72 (d, 2.3 Hz, 3H), 4.24 (s, 6H), 4.13 (s, 9H), 4.04 (s, 9H), 3.69 (br.s, 6H). MS(FAB): 930, 932.

b) N-(7-Bromo-2,3-dimethoxy-quinoxalin-5-ylmethyl)-α-aminophosphonic acid dimethyl ester At 0° C. under a nitrogen atmosphere, 0.23 ml (2.5 mmol) of dimethyl phosphite, 0.383 ml (2.75 mmol) of triethylamine and 0.476 ml (3.75 mmol) of trimethylsilyl chloride are dissolved in 25 ml of dichloromethane. After 15 minutes' stirring at 0° C., a solution of 0.78 g (0.83 mmol) of tri-N-(7-bromo-2,3-dimethoxy-quinoxalin-5-ylmethyl)-triazine in 25 ml of dichloromethane is added dropwise. After 30 hours' stirring at room temperature, the suspension is poured onto ice-cold hydrochloric acid (0.1 N in water), and 3 parts of ether are added. The organic phase is exhaustively extracted by shaking with 0.1 N aqueous hydrochloric acid. The combined aqueous phases are adjusted to a pH of from 12 to 13 with K$_2$CO$_3$ and extracted 6 times with chloroform. After drying over sodium sulfate and concentration of the organic phase, a yellow oil is obtained which is purified on a silica gel column using an ethyl acetate/dichloromethane/ethanol mixture (10:10:1) as eluant. After concentration and drying under a high vacuum, the title compound is obtained in the form of a light-yellow oil that solidifies in the form of a glass.

$^1$H-NMR (300 MHz, CDCl$_3$) 7.88 (d, 2.3 Hz, 1H), 7.54 (d, 2.3 Hz, 1H), 4.25 (s, 2H), 4.15 (s, 3H), 4.14 (s, 3H), 3.78 (d, 10 Hz, 6H), 2.95 (d, 13.1 Hz, 2H), MS(ES$^+$) 422, 420 (MH$^+$).

EXAMPLE 46

1-(7-Nitro-2,3-dioxo-1,2,3,4-tetrahydroquinoxalin-5-ylmethyl)-3-(4-methoxyphenyl)-urea The title compound can be prepared as described under Example 39 but starting from N-(2,3-dimethoxy-7-nitro-quinoxalin-5-ylmethyl)-3-(4methoxyphenyl)-urea instead of N-(2,3-dimethoxy-7-nitro-quinoxalin-5-ylmethyl)-2-methylaziridine; FAB-MS: M$^+$=385; TLC: ethyl acetate/methanol (3:1) R$_f$=0.5.

The starting material can be prepared, for example, as follows:

a) N-(2,3-Dimethoxy-7-nitro-quinoxalin-5-ylmethyl)-3-(4-methoxyphenyl)-urea 62 mg (0.416 mmol) of 4-methoxyphenyl isocyanate are added at room temperature to a suspension of 100 mg (0.379 mmol) of 5-aminomethyl-2,3-dimethoxy-7-nitro-quinoxaline in 2 ml of tert-butyl methyl ether, and the mixture is stirred for 3 hours. The suspension is then filtered off, and the filter residue is washed with tert-butyl methyl ether and dried under a high vacuum. The title compound is obtained in the form of a beige solid.

$^1$H-NMR (CDCl$_3$, 200 MHz): 8.47, 8.26 (2d, 2H), 7.70 (s, NH), 7.22 (d, 2H), 6.74 (d, 2H), 6.15 (m, NH), 4.89 (d, CH$_2$), 4.11, 4.09 (2s, 2Me), 3.70 (s, Me).

EXAMPLE 47

The following compounds are also prepared in a manner analogous to that described under Example 46:

1-(7-nitro-2,3-dioxo-1,2,3,4-tetrahydroquinoxalin-5-yl methyl)-3-(2-methoxyphenyl)-urea, FAB-MS: M$^+$=385; TLC: ethyl acetate/methanol (3:1) R$_f$=0.5;

1-(7-nitro-2,3-dioxo-1,2,3,4-tetrahydroquinoxalin-5-ylmethyl)-3-(2-ethoxycarbonylethyl)-urea;

1-(7-nitro-2,3-dioxo-1,2,3,4-tetrahydroquinoxalin-5-yl methyl)-3-(2-carboxyethyl)-urea, FAB-MS: M$^+$=351, TLC: ethyl acetate/methanol (1:3) R$_f$=0.67;

1-(7-nitro-2,3-dioxo-1,2,3,4-tetrahydroquinoxalin-5-ylmethyl)-3-phenyl-urea, FAB-MS: M+=355; TLC: ethyl acetate/methanol (3:1) R$_f$=0.70; and 1-(7-nitro-2,3-dioxo-1,2,3,4-tetrahydroquinoxalin-5-ylmethyl)-3-(4-trifluoromethyloxyphenyl)-urea, FAB-MS: M$^+$=439; TLC: ethyl acetate/methanol (3:1) R$_f$=0.50.

EXAMPLE 48

N-(7-Nitro-2,3-dioxo-1,2,3,4-tetrahydroquinoxalin-5-ylmethyl)-valeric acid amide The title compound can be prepared as described under Example 39 but starting from N-(2,3-dimethoxy-7-nitro-quinoxalin-5-ylmethyl)-valeric acid amide instead of N-(2,3-dimethoxy-7-nitro-quinoxalin-5-ylmethyl)-2-methylaziridine; FAB-MS: M$^+$=320; $^1$H-NMR (DMSO-D$_6$, 200 MHz): 12.23, 11.82 (2s, 2 NH) 8.73 (t, NH), 7.94, 7.89 (2d, 2H), 4.46 (d, CH$_2$), 2.20 (t, CH$_2$), 1.53 (quint., CH$_2$), 1.28 (hex., CH$_2$), 0.87 (t, CH$_3$). TLC: ethyl acetate/methanol (1:1 +2% acetic acid) R$_f$=0.80.

The starting material can be prepared, for example, as follows:

a) N-(2,3-Dimethoxy-7-nitro-quinoxalin-5-ylmethyl)-valeric acid amide

79 μl (0.567 mmol) of triethylamine and 55 μl (0.454 mmol) of n-valeroyl chloride are added to a suspension of 100 mg (0.378 mmol) of 5-aminomethyl-2,3-dimethoxy-7-nitro-quinoxaline in 2 ml of tert-butyl methyl ether and the mixture is stirred at room temperature for 16 hours. The mixture is then taken up in dichloromethane, washed with 1 N hydrochloric acid and with 1 N sodium hydroxide solution, dried over sodium sulfate and concentrated by evaporation. The title compound is obtained in the form of a yellowish powder.

EXAMPLE 49

The following compounds are also prepared in a manner analogous to that described under Example 48:

N-(7-nitro-2,3-dioxo-1,2,3,4-tetrahydroquinoxalin-5-yl methyl)naphthoic acid amide, FAB-MS: M$^+$=390; TLC: ethyl acetate/methanol (1:1+2% acetic acid) R$_f$=0.80;

N-(7-nitro-2,3-dioxo-1,2,3,4-tetrahydroquinoxalin-5-ylmethyl)-3,3-dimethyl-butyramide, FAB-MS: M$^+$=334; TLC: ethyl acetate/methanol (1:1+2% acetic acid) R$_f$=0.67;

N-(7-nitro-2,3-dioxo-1,2,3,4-tetrahydroquinoxalin-5-ylmethyl)-(3-acetoxy)-benzamide;

N-(7-nitro-2,3-dioxo-1,2,3,4-tetrahydroquinoxalin-5-ylmethyl)-(2-hydroxy)-benzoic acid amide, ESCl$^+$-MS: (M+H)$^+$=357; TLC: ethyl acetate/methanol (1:1+2% acetic acid) R$_f$0.33.

EXAMPLE 50

N-(7-Nitro-2,3-dioxo-1,2,3,4-tetrahydroquinoxalin-5-ylmethyl)-2-methoxy-acetamide The title compound can be prepared as described under Example 39 but starting from N-(2,3-dimethoxy-7-nitro-quinoxalin-5-ylmethyl)-2-methoxy acetamide instead of N-(2,3-dimethoxy-7-nitro-quinoxalin-5-ylmethyl)-2-methylaziridine; FAB-MS: M$^+$=308. TLC: ethyl acetate/methanol (1:1+2% acetic acid) R$_f$=0.80.

The starting material can be prepared, for example, as follows:

a) N-(2,3-Dimethoxy-7-nitro-quinoxalin-5-ylmethyl)-2-methoxy-acetamide

The title compound can be prepared as described under Example 27a) but starting from 5-aminomethyl-2,3-dimethoxy-7-nitro-quinoxaline and 2-methoxyacetic acid instead of 5-aminomethyl-7-bromo-2,3-dimethoxy-quinoxaline hydrochloride and furan-2-carboxylic acid.

EXAMPLE 51

The following compounds are also prepared in a manner analogous to that described under Example 50:

N-(7-nitro-2,3-dioxo-1,2,3,4-tetrahydroquinoxalin-5-yl methyl)-N',N'-dimethyl-glycinamide, APCl$^+$-MS: (M+H)$^+$=321; TLC: methanol/acetic acid (9:1) R$_f$=0.29;

N-(7-nitro-2,3-dioxo-1,2,3,4-tetrahydroquinoxalin-5-ylmethyl)-3,4,5-trimethoxy-benzamide, ESCl$^-$-MS: (M+H)$^+$=429; TLC: ethyl acetate/methanol (1:1+2% acetic acid) R$_f$=0.30;

N-(7-nitro-2,3-dioxo-1,2,3,4-tetrahydroquinoxalin-5-ylmethyl)-3,5-dimethoxy-4-hydroxy-benzamide, FAB-MS: M$^+$=416; TLC: ethyl acetate/methanol (1:1+2% acetic acid) R$_f$=0.90;

N-(7-nitro-2,3-dioxo-1,2,3,4-tetrahydroquinoxalin-5-ylmethyl)-N'-acetyl-glycinamide, FAB-MS: M$^+$=335; TLC: ethyl acetate/methanol (1:1+2% acetic acid) R$_f$=0.80;

N-(7-nitro-2,3-dioxo-1,2,3,4-tetrahydroquinoxalin-5-ylmethyl)-N'-carbamoyl-glycinamide, FAB-MS: M$^+$=336; TLC: ethyl acetate/methanol (1:1+2% acetic acid) R$_f$=0.60;

4-[N-(7-nitro-2,3-dioxo-1,2,3,4-tetrahydroquinoxalin-5-ylmethyl)sulfamoyl]-benzamide, ESCl$^+$-MS: (M+H)$^+$=420; TLC: methanol/acetic acid (9:1) R$_f$=0.88;

2-amino-3-methyl-N-(7-nitro-2,3-dioxo-1,2,3,4-tetrahydroquinoxalin-5-ylmethyl)-butyramide, ESCl$^+$-MS: (M+H)$^+$=336; TLC: methanol/acetic acid (9:1) R$_f$=0.68;

2-amino-3-hydroxy-N-(7-nitro-2,3-dioxo-1,2,3,4-tetrahydroquinoxalin-5-ylmethyl)-butyramide, ESCl$^+$-MS: (M+H)$^+$=338; TLC: methanol/acetic acid (9:1) R$_f$=0.48;

2-amino-4-carboxy-N-(7-nitro-2,3-dioxo-1,2,3,4-tetrahydroquinoxalin-5-ylmethyl)-butyramide, FAB-MS: M$^+$=365; TLC: methanol/acetic acid (9:1) R$_f$=0.39;

N-(7-nitro-2,3-dioxo-1,2,3,4-tetrahydroquinoxalin-5-ylmethyl)-N$_\epsilon$-acetyl-tryptophanamide hydrobromide, FAB-MS: M$^+$=464; TLC: methanol/acetic acid (9:1) R$_f$=0.25;

2-amino-N-(7-nitro-2,3-dioxo-1,2,3,4-tetrahydroquinoxalin-5-ylmethyl)-L-serine-amide, ESCl$^+$-MS: (M+H)$^+$=324; TLC: methanol/acetic acid (9:1) R$_f$=0.50;

2-amino-N-(7-nitro-2,3-dioxo-1,2,3,4-tetrahydroquinoxalin-5-ylmethyl)-D-serine-amide;

2-L-amino-3-carbamoyl-N-(7-nitro-2,3-dioxo-1,2,3,4-tetrahydroquinoxalin-5-ylmethyl)-propionic acid amide, FAB-MS: M$^+$=351; TLC: ethyl acetate/methanol (1:1+2% acetic acid) R$_f$=0.90;

2-D-amino-3-carbamoyl-N-(7-nitro-2,3-dioxo-1,2,3,4-tetrahydroquinoxalin-5-ylmethyl)-propionic acid amide;

L-N-(7-nitro-2,3-dioxo-1,2,3,4-tetrahydroquinoxalin-5-yl methyl)-histidine-amide; and D-N-(7-nitro-2,3-dioxo-1,2,3,4-tetrahydroquinoxalin-5-ylmethyl)-histidine-amide.

EXAMPLE 52

N-(7-Nitro-2,3-dioxo-1,2,3,4-tetrahydroquinoxalin-5-ylmethyl)-succinic acid amide The title compound can be prepared as described under Example 39 but starting from N-(2,3-dimethoxy-7-nitro-quinoxalin-5-ylmethyl)-succinic acid amide instead of N-(2,3-dimethoxy-7-nitro-quinoxalin-5-ylmethyl)-2-methylaziridine; FAB-MS: M$^+$=336; TLC: ethyl acetate/methanol (1:1+2% acetic acid) R$_f$=0.48.

The starting material can be prepared, for example, as follows:

a) N-(2,3-Dimethoxy-7-nitro-quinoxalin-5-ylmethyl)-succinic acid amide

55 μl (0.397 mmol) of triethylamine and 40 mg (0.397 mmol) of succinic anhydride are added to a suspension of 100 mg (0.378 mmol) of 5-aminomethyl-2,3-dimethoxy-7-nitro-quinoxaline in 2 ml of tert-butyl methyl ether and the mixture is stirred for 3 hours at room temperature. The mixture is then filtered and the residue is washed twice with tert-butyl methyl ether. The filter residue is chromatographed on silica gel with dichloromethane/methanol/acetic acid (95:4.5:0.5). The title compound is obtained in the form of a beige powder.

EXAMPLE 53

The following compounds are also prepared in a manner analogous to that described under Example 52:

N-(7-nitro-2,3-dioxo-1,2,3,4-tetrahydroquinoxalin-5-yl methyl)-phthalic acid amide;

N-(7-nitro-2,3-dioxo-1,2,3,4-tetrahydroquinoxalin-5-ylmethyl)-glutaric acid amide, FAB-MS: M$^+$=350; TLC: ethyl acetate/methanol (1:1+2% acetic acid) R$_f$=0.70;

N-(7-nitro-2,3-dioxo-1,2,3,4-tetrahydroquinoxalin-5-ylmethyl)-N-methyl-succinic acid amide, FAB-MS: M$^+$=350; TLC: methylene chloride/methanol/acetic acid (80:18:2) R$_f$=0.46.

EXAMPLE 54

N-(7-Nitro-2,3-dioxo-1,2,3,4-tetrahydroquinoxalin-5-ylmethyl)-N-(2-diethylaminoethyl)-amine dihydrobromide The title compound can be prepared as described under Example 39 but starting from N-(2,3-dimethoxy-7-nitro-quinoxalin-5-ylmethyl)-N-(2diethylaminoethyl)-amine instead of N-(2,3-dimethoxy-7-nitro-quinoxalin-5-ylmethyl)-2-methylaziridine; FAB-MS: M$^+$=335; TLC: methanol/water (5:1) R$_f$=0.16.

The starting material can be prepared, for example, as follows:

a) N-(2,3-Dimethoxy-7-nitro-quinoxalin-5-ylmethyl)-N-(2-diethylaminoethyl)-amine The title compound can be prepared as described under Example 39 a), that is to say from 5-bromomethyl-2,3-dimethoxy-7-nitro-quinoxaline and 2-diethylaminoethylamine. The title compound is obtained in the form of a colorless oil.

EXAMPLE 55

The following compounds are prepared in a manner analogous to that described under Example 54:

N-(7-nitro-2,3-dioxo-1,2,3,4-tetrahydroquinoxalin-5-yl methyl)-N-methyl-amine hydrobromide;

N-(7-nitro-2,3-dioxo-1,2,3,4-tetrahydroquinoxalin-5-ylmethyl)-N-(1,1-dioxo-2,3,4,5-tetrahydro-thien-3-yl)-amine hydrobromide, FAB-MS: M$^+$=354; TLC: methanol/acetic acid (9:1) R$_f$=0.69;

N-(7-nitro-2,3-dioxo-1,2,3,4-tetrahydroquinoxalin-5-yl methyl)-N-methyl-N-(2-hydroxyethyl)-amine hydrobromide;

N-(7-nitro-2,3-dioxo-1,2,3,4-tetrahydroquinoxalin-5-yl methyl)-N-(3,4-methylenedioxybenzyl)-amine hydrobromide, APCl$^+$-MS: (M+H)$^+$=371; TLC: methanol/acetic acid (9:1) R$_f$=0.70;

N-(7-nitro-2,3-dioxo-1,2,3,4-tetrahydroquinoxalin-5-ylmethyl)-N-methyl-N-methoxy-amine hydrobromide, ESCl$^+$-MS: (M+H)$^+$=281; TLC: methanol/acetic acid (9:1) R$_f$=0.86;

N-(7-nitro-2,3-dioxo-1,2,3,4-tetrahydroquinoxalin-5-ylmethyl)-N-isopropyl-amine hydrobromide, APCl$^+$-MS: (M+H)$^+$=279; TLC: methanol/acetic acid (9:1) R$_f$=0.53;

N-(7-nitro-2,3-dioxo-1,2,3,4-tetrahydroquinoxalin-5-ylmethyl)-N'-acetyl-ethylenediamine hydrobromide, FAB-MS: M$^+$=321; TLC: methanol/acetic acid (9:1) R$_f$=0.40;

cis-2-[N-(7-nitro-2,3-dioxo-1,2,3,4-tetrahydroquinoxalin-5-ylmethyl)amino]-cyclohexane-1-carboxamide hydrobromide, FAB-MS: M$^+$=359; TLC: methanol/acetic acid (9:1) R$_f$=0.50;

N-(7-nitro-2,3-dioxo-1,2,3,4-tetrahydroquinoxalin-5-ylmethyl)-N-methyl-taurine hydrobromide, FAB-MS: M$^+$=357; TLC: methanol/acetic acid (9:1) R$_f$=0.69;

cis-3-[N-(7-nitro-2,3-dioxo-1,2,3,4-tetrahydroquinoxalin-5-ylmethyl)amino]-cyclohexane-1-carboxylic acid hydrobromide, FAB-MS: M$^+$=362; TLC: methanol/acetic acid (9:1) R$_f$=0.70;

3-[N-(7-nitro-2,3-dioxo-1,2,3,4-tetrahydroquinoxalin-5-ylmethyl)amino]-3-phenyl-propionic acid hydrobromide, ESCl$^+$-MS: (M+H)$^+$=385; TLC: methanol/acetic acid (9:1) R$_f$=0.34;

cis-2-[N-(7-nitro-2,3-dioxo-1,2,3,4-tetrahydroquinoxalin-5-ylmethyl)amino]-cyclopentane-carboxylic acid hydrobromide;

N-(7-nitro-2,3-dioxo-1,2,3,4-tetrahydroquinoxalin-5-ylmethyl)-pyrrolidin-2-one, FAB-MS: M$^+$=304; TLC: ethyl acetate/methanol (2:1+2% acetic acid) R$_f$=0.60;

N-(7-nitro-2,3-dioxo-1,2,3,4-tetrahydroquinoxalin-5-ylmethyl)-pyrrolidine-4-(4-chlorophenyl)-2-one, FAB-MS: M$^+$=414; TLC: methanol/water (10:1) R$_f$=0.78;

N-(7-nitro-2,3-dioxo-1,2,3,4-tetrahydroquinoxalin-5-ylmethyl)-N-(1-acetoxy-2-methyl-prop-2-yl)-amine hydrobromide, FAB-MS: M$^+$=350; TLC: methanol/acetic acid (9:1) R$_f$=0.86;

N-(7-nitro-2,3-dioxo-1,2,3,4-tetrahydroquinoxalin-5-ylmethyl)-N-cyclohexyl-N-methyl-amine hydrobromide, FAB-MS: M$^+$=332; TLC: methanol/acetic acid (9:1) R$_f$=0.70; and N-(7-nitro-2,3-dioxo-1,2,3,4-tetrahydroquinoxalin-5-ylmethyl)-N-(1,1-dimethyl-2-hydroxyethyl)-amine hydrochloride, ESCl$^+$-MS: (M+H)$^+$=309; TLC: methanol/acetic acid (9:1) R$_f$=0.62.

EXAMPLE 56 cis-2-[N-(7-Nitro-2,3-dioxo-1,2,3,4-tetrahydroquinoxalin-5-ylmethyl)amino]-cyclohexane-1-carboxylic acid hydrobromide The title compound can be prepared as described under Example 39 but starting from cis-2-[N-(2,3-dimethoxy-7-nitro-quinoxalin-5-ylmethyl)amino]-cyclohexane-1-carboxylic acid instead of N-(2,3-dimethoxy-7-nitro-quinoxalin-5-ylmethyl)-2-methylaziridine;

m.p.=249–251° C.; ESCl MS: (M−H)$^+$=361; TLC: methanol/acetic acid (9:1) R$_f$=0.1–0.45.

The starting material can be prepared, for example, as follows:

a) 2,3-Dimethoxy-quinoxaline-5-carbaldehyde 17 ml (188 mmol) of 2-nitropropane are added to a solution of 3.7 g (163 mmol) of sodium in 700 ml of methanol. After 5 minutes' stirring, 35.5 g (125.4 mmol) of solid 2,3-dimethoxy-5-bromomethyl-quinoxaline are added. The mixture is heated at reflux for 1 hour, a homogeneous solution being formed. After cooling, the solution is concentrated under reduced pressure. The residue is taken up in ethyl acetate and 1 N HCl, the phases are separated and the organic phase is washed with water and brine, dried over sodium sulfate and concentrated. The title compound is isolated in the form of white crystals by crystallization from ethyl acetate.

M.p. 137–140° C.; TLC (EtOAc/hexane 1:3): R$_f$=0.45.

b) 2,3-Dimethoxy-7-nitro-quinoxaline-5-carbaldehyde 44 ml of 100% nitric acid, 44 ml of 97% sulfuric acid and 44 ml of trifluoroacetic anhydride are added in succession to a solution, cooled to 0° C., of 22 g (100.8 mmol) of 2,3-dimethoxy-quinoxaline-5-carbaldehyde in 88 ml of trifluoroacetic acid. The mixture is maintained at 0° C. for 2 hours and is then carefully poured onto a mixture of 4N NaOH and ice. The temperature should not exceed 20° C. The mixture is extracted with ethyl acetate. The organic phase is washed with an aqueous 1 N NaOH solution, water and brine and dried over sodium sulfate. Crystallization of the crude product yields the title compound in the form of light-yellow crystals. M.p.: 147–149° C.; TLC (EtOAc/hexane 1:3): R$_f$=0.25.

c) cis-2-[N-(2,3-Dimethoxy-7-nitro-quinoxalin-5-ylmethyl)amino]-cyclohexane-1-carboxylic acid 105 mg (0.588 mmol) of cis-2-amino-cyclohexanecarboxylic acid and 82 μl (0.588 mmol) of triethylamine are added in succession to a solution of 129 mg (0.490 mmol) of 2,3-dimethoxy-7-nitro-quinoxaline-5-carbaldehyde in 1 ml of dichloromethane and 2 ml of ethanol. After 3 hours' stirring at room temperature, 1 g of anhydrous sodium sulfate is added to the suspension and the mixture is stirred for a further 20 hours at room temperature. The thick suspension is diluted with 0.5 ml of ethanol and 46 mg (1.23 mmol) of sodium borohydride are added. After 3 hours' stirring, there are added 0.5 ml of acetone and 10 minutes later 0.3 ml of acetic acid and filtration is carried out. The filter residue is washed with ethanol and dichloromethane. The filtrate is chromatographed on silica gel first with dichloromethane/ethyl acetate (97:3) and then with dichloromethane/methanol/glacial acetic acid (90:9:1). The title compound is obtained in the form of a white powder.

EXAMPLE 57

The following compounds are also prepared in a manner analogous to that described under Example 56:

N-(7-nitro-2,3-dioxo-1,2,3,4-tetrahydroquinoxalin-5-yl methyl)-amino-methanephosphonic acid hydrobromide;

N-(7-nitro-2,3-dioxo-1,2,3,4-tetrahydroquinoxalin-5-yl methyl)-amino-(3-methoxyphenyl)-methanephosphonic acid hydrochloride, FAB-MS: M$^+$=436; HPLC: CH$_3$CN/H$_2$O+0.1% trifluoroacetic acid 20:80 R$_t$4.2 min. (NucleosiL$_1$00. C$_{18}$, 5 μM, 250×4.6 mm);

[(7-nitro-2,3-dioxo-1,2,3,4-tetrahydroquinoxalin-5-y-methylamino)-(3-hydroxy-phenyl)-methyl]-phosphonic acid hydrobromide, FAB-MS: M$^+$=422; HPLC: CH$_3$CN/H$_2$O+0.1% trifluoroacetic acid 20:80 R$_t$=2.9 min. (NucleosiL$_1$00. C$_{18}$, 5 μM, 250×4.6 mm);

N-(7-nitro-2,3-dioxo-1,2,3,4-tetrahydroquinoxalin-5-ylmethyl)-N-[(4-diethoxy-phosphoryl)-benzyl]-amine hydrochloride, ESCl$^-$-MS: (M−H)$^+$=421; TLC: methylene chloride/methanol/acetic acid (9:0.5:0.5) R$_f$=0.28;

N-(7-nitro-2,3-dioxo-1,2,3,4-tetrahydroquinoxalin-5-ylmethyl)-3-amino-propane-1-phosphonic acid hydrobromide;

N-(7-nitro-2,3-dioxo-1,2,3,4-tetrahydroquinoxalin-5-yl methyl)-2-amino-ethanesulfonic acid hydrobromide;

N-(7-nitro-2,3-dioxo-1,2,3,4-tetrahydroquinoxalin-5-yl methyl)-2-amino-2-phenyl-ethanecarboxylic acid hydrobromide;

cis-2-[N-(7-nitro-2,3-dioxo-1,2,3,4-tetrahydroquinoxalin-5-ylmethyl)amino]-cyclopentane-1-carboxylic acid hydrobromide;

trans-2-[N-(7-nitro-2,3-dioxo-1,2,3,4-tetrahydroquinoxalin-5-yl methyl)amino]-cyclopropane-1-phosphonic acid hydrobromide;

N-(7-nitro-2,3-dioxo-1,2,3,4-tetrahydroquinoxalin-5-yl methyl)-amino-(3-pyridyl)-methanephosphonic acid hydrochloride;

N-(7-nitro-2,3-dioxo-1,2,3,4-tetrahydroquinoxalin-5-yl methyl)-3-amino-1-carboxy-propane-1-phosphonic acid hydrobromide; and 4-[N-(7-nitro-2,3-dioxo-1,2,3,4-tetrahydroquinoxalin-5-ylmethyl)amino]-butyric acid, FAB-MS: M$^+$=322; TLC: methanol/acetic acid (9:1) R$_f$=0.30.

EXAMPLE 58

N-(7-Nitro-2,3-dioxo-1,2,3,4-tetrahydroquinoxalin-5-ylmethylaminomethyl)-tetrazole hydrochloride 160 mg (0.461 mmol) of N-(2,3-dimethoxy-7-nitro-quinoxalin-5-ylmethylaminomethyl)-tetrazole are stirred at reflux for 20 hours in 6 ml of 2N aqueous HCl. The reaction mixture is cooled and the resulting solid is filtered off and washed with diethyl ether.

M.p.=230° C. (decomp.).

a) N-(2,3-Dimethoxy-7-nitro-quinoxalin-5-ylmethyl)-aminoacetonitrile 300 mg (0.914 mmol) of 5-bromomethyl-2,3-dimethoxy-7-nitro-quinoxaline, 338 mg (4 equiv.) of aminoacetonitrile hydrochloride and 0.66 ml (4 equiv.) of Hünig base are stirred at reflux for 20 hours in 10 ml of acetonitrile. The reaction mixture is concentrated by evaporation and the residue is extracted with ethyl acetate and an approximately 5% sodium carbonate solution. The combined organic phases are washed once with brine, dried over magnesium sulfate and concentrated by evaporation. The resulting brown oil is chromatographed on silica gel (ethyl acetate/petroleum ether 1:2, then 1:1) and the title compound is obtained in the form of a yellowish solid.

b) N-(2,3-Dimethoxy-7-nitro-quinoxalin-5-ylmethylaminomethyl)-tetrazole 140 mg (0.461 mmol) of N-(2,3-dimethoxy-7-nitro-quinoxalin-5-ylmethyl)-aminoacetonitrile, 50 mg (0.43 equiv.) of dibutyltin oxide and 0.244 ml (4 equiv.) of trimethylsilyl azide are stirred at reflux for 16 hours in 6 ml of toluene. The reaction mixture is cooled and the title compound is filtered off in the form of a brown solid.

EXAMPLE 59

N-(7-Nitro-2,3-dioxo-1,2,3,4-tetrahydroauinoxalin-5-ylmethyl)-2-amino-ethaneghosphonic acid hydrobromide 380 mg (0.949 mmol) of N-(2,3-dimethoxy-7-nitro-quinoxalin-5-ylmethyl)-2-amino-ethanephosphonic acid dimethyl ester and 1.23 ml (10 equiv.) of trimethylsilyl bromide are dissolved in 20 ml of dichloromethane and the solution is stirred for 90 minutes at room temperature. The reaction mixture is concentrated by evaporation and the residue is stirred at 40° C. for 17 hours in 6 ml of an approximately 33% hydrogen bromide solution in acetic acid. The reaction mixture is diluted with diethyl ether and the solid is filtered off, washed thoroughly with diethyl ether and dried. The title compound is obtained in the form of a yellowish solid. M.p.=235° C. (decomp.).

The starting materials can be prepared, for example, as follows:

a) N-(2,3-Dimethoxy-7-nitro-auinoxalin-5-ylmethyl)-2-aminoethanephosghonic acid dimethyl ester 0.19 ml (1.2 equiv.) of triethylamine, 0.215 ml (1.5 equiv.) of trimethylchlorosilane and 0.104 ml of dimethyl phosphite are dissolved in dichloromethane at 0° C. and the solution is stirred for 20 minutes. A solution of 329 mg (1.1 35 mmol) of 2,3-dimethoxy-5-ethylidene-aminomethyl-7-nitro-quinoxaline in dichloromethane is added to the reaction mixture and stirring is carried out at 0° C. for 5 hours and then at room temperature for 12 hours. The solution is diluted with water and extracted three times with dichloromethane. The organic phases are combined, dried over magnesium sulfate and concentrated by evaporation. The title compound is obtained in the form of a yellow solid.

b) 2,3-Dimethoxy-5-ethylideneaminomethyl-7-nitro-guinoxaline 300 mg (1.135 mmol) of 2,3-dimethoxy-5-aminomethyl-7-nitro-quinoxaline, 500 mg (3.7 equiv.) of magnesium sulfate and 200 mg (1.28 equiv.) of potassium carbonate are suspended in 20 ml of dichloromethane at room temperature. After 15 minutes, 0.13 ml of acetaldehyde is added, and the reaction mixture is stirred at room temperature for 7 hours, then filtered and concentrated by evaporation.

EXAMPLE 60

2-(2,3-Dioxo-7-nitro-1,2,3,4-tetrahydroquinoxalin-5-ylmethoxy)-acetic acid 270 mg (0.711 mmol) of 2-(2,3-dimethoxy-7-nitro-quinoxalin-5-ylmethoxy)-acetic acid tert-butyl ester are dissolved in 6 ml of an approximately 16% hydrogen bromide solution in acetic acid and the solution is stirred at room temperature for 20 hours. The reaction mixture is diluted with diethyl ether and the solid is filtered off, washed with diethyl ether and dried. The title compound is obtained in the form of a solid (m.p.>300° C.).

The starting material can be prepared, for example, as follows:

a) 2-(2,3-Dimethoxy-7-nitro-quinoxalin-5-ylmethoxy)-acetic acid tert-butyl ester 300 mg (1.13 mmol) of 2,3-dimethoxy-5-hydroxymethyl-7-nitro-quinoxaline are placed in 8 ml of tetrahydrofuran and cooled to 0° C. 52 mg (1.05 equiv.) of approximately 55% NaH in oil are added and the mixture is stirred for 30 minutes at 0° C. 0.2 ml (1.5 equiv.) of bromo-acetic acid tert-butyl ester is added and after 20 minutes the ice-bath is removed. The reaction mixture is stirred at room temperature for 20 hours, diluted with water and extracted with ethyl acetate. The combined organic phases are washed once with brine, dried over magnesium sulfate and concentrated by evaporation. The residue is chromatographed (SiO$_2$, ethyl acetate/petroleum ether 1:3) and the title compound is obtained in the form of a solid (340 mg).

b) 2,3-Dimethoxy-5-hydroxymethyl-7-nitro-quinoxaline

The title compound is prepared as described in Example 14a) but starting from 5-bromomethyl-2,3-dimethoxy-7-nitro-quinoxaline.

EXAMPLE 61

2-(7-Nitro-2,3-dioxo-1,2,3,4-tetrahydroquinoxaline-5-methoxy)-propionic acid

The title compound is prepared in a manner analogous to that described in Example 60 but starting from 2-bromopropionic acid tert-butyl ester; m.p.=268° C. (decomp.).

EXAMPLE 62

N-(7-Nitro-2,3-dioxo-1,2,3,4-tetrahydroquinoxalin-5-ylmethyl)-4-amino-pyridinium bromide 212 mg (0.5 mmol) of 4-amino-1-(2,3-dimethoxy-7-nitro-quinoxalin-5-yl methyl)-pyridinium bromide are stirred in 3 ml of a 48% solution of hydrogen bromide in glacial acetic acid for 18 hours at room temperature. The brownish reaction mixture is diluted with 7 ml of diethyl ether and then stirred for 10 minutes. The resulting solid is filtered off, washed with a small amount of diethyl ether and dried. The title compound is obtained in the form of a yellow solid having a melting point of>245° C. (decomp.).

The starting material can be prepared, for example, as follows:

a) 4-Amino-1-(2,3-dimethoxy-7-nitro-quinoxalin-5-ylmethyl)-pyridinium bromide

A solution of 197 mg (0.6 mmol) of 5-bromomethyl-2,3-dimethoxy-7-nitro-quinoxaline in 2 ml of dichloromethane is added at room temperature to a suspension of 282 mg (3 mmol) of 4-aminopyridine in 1 ml of dichloromethane and 3 ml of acetonitrile and the mixture is then stirred for 3.5 hours at room temperature. The resulting precipitate is filtered off and then washed on the filter with a small amount of acetonitrile. The title compound is obtained in the form of a colorless powder.

EXAMPLE 63

N-(7-Nitro-2,3-dioxo-1,2,3,4-tetrahydroquinoxalin-5-ylmethyl)-3-amino-pyridinium bromide The title compound can be prepared in a manner analogous to that described in Example 62 but starting from 3-aminopyridine; m.p.>248° C. (decomp.).

EXAMPLE 64

N-(7-Nitro-2,3-dioxo-1,2,3,4-tetrahydroquinoxalin-5-ylmethyl)-2-amino-pyridinium bromide The title compound can be prepared in a manner analogous to that described in Example 62 but starting from 2-aminopyridine; m.p.>350° C. (decomp.).

EXAMPLE 65

3-(7-Chloro-2,3-dioxo-quinoxalin-5-yl)-propan-1-ol

The title compound is obtained in a manner analogous to that described in Example 15 by heating 3-(7-chloro-2,3-dimethoxy-quinoxalin-5-yl)-propan-1-ol with acetic acid/2N hydrochloric acid.

The starting material can be prepared, for example, as follows:

a) 5-Iodo-2,3,7-trichloro-quinoxaline 406.9 g (1.953 mol) of phosphorus pentachloride are added to a mixture of 195.9 g (0.93 mol) of 7-chloro-5-iodo-quinoxaline-dione in 1200 ml of phosphorus oxychloride and the mixture is stirred under reflux for 18 hours. The excess phosphorus oxychloride is distilled off from the reaction mixture at a bath temperature of 150° C. The residue is poured onto 6000 ml of ice-water and the resulting suspension is stirred for 2 hours, filtered with suction and then washed with a large amount of water. The filter residue is dried in vacuo at 60° C. 205.89 g (89.4%) of 5-iodo-2,3,7-trichloro-quinoxaline are obtained in the form of pale brown, crude crystals which can be reacted further without further purification.

b) 7-Chloro-2,3-dimethoxy-5-iodo-quinoxaline 205 g (0.828 mol) of 5-iodo-2,3,7-trichloro-quinoxaline are placed in 2255 ml of methanol at room temperature, and 463.9 ml of an approximately 5.4 molar solution of sodium methanolate in methanol are added. The reaction mixture is then heated to reflux and stirred for 18 hours. The reaction mixture is cooled to 0° C. and the suspension is filtered with suction. The filter residue is then washed with methanol and dried in vacuo at 60° C., and the crude product is purified by means of continuous extraction with diethyl ether. 96.4 g (48.8%) of 7-chloro-2,3-dimethoxy-5-iodo-quinoxaline having a melting point of 94–96° C. are obtained.

c) 3-(7-Chloro-2,3-dimethoxy-quinoxalin-5-yl)-prop-2-yn-1-ol 12.9 g (36.8 mmol) of 7-chloro-2,3-dimethoxy-5-iodo-quinoxaline, 7.6 ml (128.4 mmol) of propargyl alcohol, 2.1 g (3 mmol) of bis(triphenylphosphine)-palladium dichloride, 6.6 ml (47.4 mmol) of triethylamine and 0.34 g (1.8 mmol) of cuprous iodide are placed in 125 ml of dimethylformamide and heated to a bath temperature of 70° C. The reaction mixture is then stirred for 3.5 hours at that temperature and then cooled to room temperature. Ethyl acetate is added to the reaction mixture and extraction is carried out with water, 1N hydrochloric acid and brine. The aqueous phases are washed with ethyl acetate. The organic phases are combined, dried over sodium sulfate, filtered with suction and concentrated. Chromatography of the crude product on silica gel with hexane/ethyl acetate (3:1) yields 1.1 g of 3-(7-chloro-2,3-dimethoxy-quinoxalin-5-yl)-prop-2-yn-1-ol in the form of brown crystals having a melting point of 137–140° C.

d) 3-(7-Chloro-2,3-dimethoxy-quinoxalin-5-yl)-propan-1-ol 2.05 g (7.36 mmol) of 3-(7-chloro-2,3-dimethoxy-quinoxalin-5-yl)-prop-2-yn-1-ol are hydrogenated at normal pressure in 20 ml of tetrahydrofuran with approximately 0.4 g of Raney nickel until twice the molar amount of hydrogen has been absorbed. The hydrogenated mixture is filtered with suction over a glass fiber filter and the filtrate is concentrated. 2.04 g (98%) of 3-(7-chloro-2,3-dimethoxy-quinoxalin-5-yl)-propan-1-ol are obtained in the form of beige crystals having a melting point of 104–105° C.

EXAMPLE 66

4-(7-Chloro-2,3-dioxy-1,2,3,4-tetrahydro-quinoxalin-5-yl)butanol

The title compound is obtained in a manner analogous to that described in Example 65 via 4-(7-chloro-2,3-dimethoxy-1,2,3,4-tetrahydro-quinoxalin-5-yl)butanol, there being used in step c), instead of propargyl alcohol, the corresponding amount of but-3-ynol.

EXAMPLE 67

N-[3-(7-Chloro-2,3-dioxo-1,2,3,4-tetrahydroquinoxalin-5-yl)propyl]-glycine hydrobromide The title compound is obtained in a manner analogous to that described in Example 1 by reacting 5-(3-bromopropyl)-7-chloro-2,3-dimethoxy-quinoxaline with triethylamine and glycine tert-butyl ester hydrochloride and triethylamine in acetonitrile, followed by hydrolysis.

The starting material can be prepared, for example, as follows:

a) 5-(3-Bromopropyl)-7-chloro-2,3-dimethoxy-quinoxaline 0.5 g (1.77 mmol) of 3-(7-chloro-2,3-dimethoxy-quinoxalin-5-yl)-propan-1-ol and 0.287 g (1.77 mmol) of 1,1'-carbonyldiimidazole are placed in 5 ml of acetonitrile under $N_2$. 0.75 ml of allyl bromide is added, and the mixture is then stirred at room temperature for 30 minutes and at reflux for 2 hours. The reaction mixture is cooled to room temperature, diethyl ether is added and extraction is carried out with water, 0.1N hydrochloric acid, saturated sodium hydrogen carbonate solution and brine. The aqueous phases are then washed with diethyl ether. The organic phases are combined, dried over sodium sulfate, filtered over a layer of silica gel and concentrated. 0.438 g (79.9%) of 5-(3-bromopropyl)-7-chloro-2,3-dimethoxy-quinoxaline is obtained in the form of a yellow oil which is used further without further purification.

EXAMPLE 68

N-(7-Nitro-2,3-dioxo-1,2,3,4-tetrahydroquinoxalin-5-ylmethyl)-N-methyl-amine

The title compound is obtained in a manner analogous to that described in Example 34 by treating N-(7-nitro-2,3-dimethoxy-1,2,3,4-tetrahydroquinoxalin-5-ylmethylene)-N-methyl-amine with a 25% solution of hydrogen bromide in acetic acid.

The starting material can be prepared, for example, as follows:

a) N-(7-Nitro-2,3-dimethoxy-1,2,3,4-tetrahydroquinoxalin-5-ylmethyl)-N-methyl-amine N-(7-Nitro-2,3-dimethoxy-1,2,3,4-tetrahydroquinoxalin-5-ylmethylene)-N-methyl-imine is reduced with sodium borohydride in ethanol to form the title compound.

b) 7-Bromo-5-formyl-2,3-dimethoxy-quinoxaline 1.38 g (60 mmol) of sodium are dissolved in portions, at 0° C. under $N_2$, in 200 ml of methanol. At 0° C., 5.85 ml (65 mmol) of 2-nitropropane are added dropwise. 18.1 g (50 mmol) of 5-(bromomethyl)-7-bromo-2,3-dimethoxy-quinoxaline are then added. The beige suspension is heated to reflux and stirred for 1 hour. The reaction mixture is poured onto 600 ml of water and the methanol is distilled off. The residue is extracted twice with ethyl acetate, and the organic phases are dried over sodium sulfate and filtered with suction. The filtrate is concentrated and the residue is dried under a high vacuum. 7-Bromo-5-formyl-2,3-dimethoxy-quinoxaline is obtained in the form of beige crystals having a melting point of 179–182° C.

c) N-(7-Nitro-2,3-dimethoxy-1,2,3,4-tetrahydroquinoxalin-5-ylmethylene)-N-methyl-imine The title compound is obtained by customary condensation of 7-bromo-5-formyl-2,3-dimethoxy-quinoxaline with methylamine.

d) N-(7-Nitro-2,3-dimethoxy-1,2,3,4-tetrahydroquinoxalin-5-ylmethylene)-N-methyl-amine The title compound is obtained by reducing N-(7-nitro-2,3-dimethoxy-1,2,3,4-tetrahydroquinoxalin-5-ylmethylene)-N-methyl-imine in customary manner, for example by means of sodium borohydride in tetrahydrofuran.

EXAMPLE 69

N-(7-Nitro-2,3-dioxo-1,2,3,4-tetrahydroquinoxalin-5-ylmethyl)-N-triethyl-ammonium bromide The title compound can be prepared as described under Example 39 but starting from N-(2,3-dimethoxy-7-nitro-quinoxalin-5-ylmethyl)-N-triethyl-ammonium bromide instead of N-(2,3-dimethoxy-7-nitro-quinoxalin-5-ylmethyl)-2-methylaziridine; $ESCl^-$-MS: $(M-H)^+$=361; TLC: methanol/acetic acid (9: 1) $R_f$=0.1–0.45.

The starting material can be prepared, for example, as follows:

a) N-(2,3-Dimethoxy-7-nitro-quinoxalin-5-ylmethyl)-N-triethyl-ammonium bromide 0.795 g (3.65 mmol) of bis-tert-butoxycarbonyl-amine and 641 μl (4.58 mmol) of triethylamine are added in succession to a solution of 1.0 g (3.05 mmol) of 5-bromomethyl-2,3-dimethoxy-7-nitro-quinoxaline in 5 ml of dimethylformamide. After 4 hours' stirring at 50° C., 10 ml of tert-butyl methyl ether are added to the suspension, filtration is carried out and the filter residue is washed with tert-butyl methyl ether. The title compound is obtained as an unexpected by-product in the form of white crystals.

EXAMPLE 70

3-[1-(2,3-Dimethoxy-7-nitro-quinoxalin-5-yl)-ethylamino] propionic acid ethyl ester A solution of 0.139 g (0.5 mmol) of 1-(2,3-dimethoxy-7-nitro-quinoxalin-5-yl)-ethanone, 0.071 g (0.5 mmol) of ⊖-alanine ethyl ester hydrochloride and 0.082 g (0.5 mmol) of sodium acetate in 50 ml of toluene, 2 ml of water and 20 ml of ethanol is concentrated at 250 mbar and 70° C. The product is taken up in a mixture of toluene/ethanol (3:1) and concentrated to dryness by evaporation under reduced pressure.

The residue is taken up in 3 ml of tetrahydrofuran, and 0.023 g (0.6 mmol) of sodium boranate and 1 ml of methanol are added. After 18 hours' stirring at 25° C., the mixture is acidified with 1 N HCl and after 15 minutes is rendered basic again with 10% aqueous sodium hydrogen carbonate solution. The mixture is extracted with ethyl acetate. The organic phase is washed with brine, dried over sodium sulfate and concentrated to dryness by rotary evaporation. Chromatography on silica gel using ethyl acetate/hexane (1:1) as eluant yields the title compound in the form of an oil that solidifies immediately.

TLC (EtOAc/hexane 1:1): $R_f$=0.20 $^1$H-NMR (CDCl$_3$): δ 8.57 (d, J=3 Hz, 1H); 8.39 (d, J=3 Hz, 1H); 4.73 (q, J=7 Hz, 1H); 4.21 (s, 3H); 4.18 (s, 3H); 4.12 (q, J=7 Hz, 2H); 2.86–2.62 (m, 2H); 2.55–2.47 (m, 2H); 2.0–1.7 (br, NH); 1.51 (d, J=7 Hz, 3H); 1.23 (t, J=7 Hz, 3H).

The starting material can be prepared, for example, as follows:

a) 5-Bromo-7-nitro-quinoxaline-2,3-dione

A solution of $Na_2S_2$, prepared by briefly heating 8.91 g (40 mmol) of crystalline sodium sulfide polyhydrate (sodium sulfide content 33–38% by weight) and 1.28 g of sulfur (40 mmol) in a mixture of 40 ml of water and 10 ml of ethanol at reflux under a nitrogen atmosphere, is added to a stirred suspension of 10.48 g (40 mmol) of 2-bromo-4,6-dinitroaniline and 2.08 g (40 mmol) of ammonium chloride in 70 ml of ethanol and 40 ml of water. The mixture is stirred for 30 minutes at 65° C. 40 ml of 2N NaOH are then added dropwise in the course of 30 minutes and the mixture is then stirred for a further 15 minutes at 65° C. After cooling, the reaction mixture is poured onto a mixture of 40 ml of 2N HCl, 100 g of ice and 700 ml of water, stirred for 15 minutes to complete the reaction and is extracted twice with ethyl acetate. The combined organic phases are dried over sodium sulfate, treated with 3 g of animal charcoal with brief heating and filtered over High-Flow®. Concentration using a rotary evaporator yields reddish-brown 3-bromo-5-nitro-1,2-diamine; TLC: ethyl acetate/hexane (1:1): $R_f$=0.40.

Without further purification, the product is heated to 150° C. (bath temperature) with 17 g (135 mmol) of oxalic acid dihydrate and 50 ml of oxalic acid diethyl ester in 100 ml of toluene. Ethanol and water formed in the course of the reaction are distilled off together with toluene during the reaction by way of a short Vigreux column. The mixture is then heated further to 190° C. until no more liquid is distilled over. Excess oxalic acid diethyl ester is removed in vacuo. The olive-green residue is suspended in 100 ml of acetic acid and heated at reflux for 3 hours. After cooling, filtration is carried out and the grey solid is washed with a large amount of acetic acid, water, ethanol and tert-butyl methyl ether. The title compound is obtained.

TLC (EtOAc/HOAc 98:2): $R_f$=0.45 $^1$H-NMR (DMSO-D$_6$): ∈ 812.3 (br, 1H, NH), 11.6 (br, 1H, NH), 8.19 (1H, d, J=2.5 Hz), 7.96 (1H, d, J=2.5 Hz).

b) 2,3-Dimethoxy-5-bromo-7-nitro-quinoxaline

In a manner analogous to that described in Examples 4b2) and 4c2), starting from 5-bromo-7-nitro-quinoxaline-2,3-dione, the title compound is obtained in the form of yellow crystals.

M.p.=171–175° C.; $^1$H-NMR (CDCl$_3$): δ 8.61 (d, J=3 Hz, 1H), 8.58 (d, J=3 Hz, 1H), 4.28 (s, 3H), 4.20 (s, 3H).

c) 1-(2,3-Dimethoxy-7-nitro-quinoxalin-5-yl)-ethanone

A mixture of 3.84 g (12.23 mmol) of 2,3-dimethoxy-5-bromo-7-nitro-quinoxaline, 4.41 g (12.23 mmol) of tributyl-(1-ethoxy-vinyl)-stannane and 0.055 g (0.244 mmol) of Pd(OAc)$_2$ in 50 ml of DMF is stirred for 4 hours at 80° C. Most of the solvent is removed under reduced pressure. The residue is taken up in ethyl acetate, washed with water and brine, dried and concentrated by rotary evaporation. Chromatography over silica gel using methylene chloride/hexane (1:1) as eluant yields the intermediate vinyl ether in the form of a light-yellow solid. That material is stirred for 1 hour in tetrahydrofuran/1 N HCl at 25° C. The mixture is diluted with ethyl acetate, washed three times with brine, dried over sodium sulfate and concentrated by rotary evaporation. The title compound is isolated (using ethyl acetate/hexane) in the form of light-yellow-colored needles.

M.p.: 155–157° C.; TLC (EtOAc/hexane 1:3): $R_f$=0.25.

EXAMPLE 71

3-[1-(7-Nitro-2,3-dioxo-1,2,3,4-tetrahydro-quinoxalin-5-yl)-1-ethylamino]-propionic acid hydrochloride A suspension of 0.13 g (0.34 mmol) of 3-[1-(2,3-dimethoxy-7-nitro-quinoxalin-5-yl)-ethyl-amino]propionic acid ethyl ester in 3 ml of methanol and 2 ml of 2N NaOH is stirred at 25° C. After 1 hour, the mixture is adjusted to pH 4 and extracted with chloroform/ethanol. The combined organic phases are extracted, dried over $Na_2SO_4$ and concentrated by rotary evaporation. The residue is heated at boiling with 4N HCl for 18 hours. The mixture is concentrated to dryness by rotary evaporation. Crystallization from water yields the title compound in the form of light-beige crystals having a melting point of>300° C.

$^1$H-NMR (DMSO-$D_6$): δ 12.4 (s, 2H); 8.32 (d, J=3 Hz, 1H); 8.02 (d, J=3 Hz, 1H); 5.1–4.95 (br, 1H); 3.2–2.9 (br, 2H); 2.67 (t, J=7 Hz); 1.57 (d, J=7 Hz, 3H). MS(ES–): 321 (M–H)$^-$.

EXAMPLE 72

1-[2-(7-Nitro-2,3-dioxo-1,2,3,4-tetrahydro-quinoxalin-5-yl)-ethyl]-piperidine-4-carboxylic acid tert-butyl ester The title compound can be prepared in a manner analogous to that described in Example 1 by reacting (2,3-dimethoxy-7-nitro-quinoxalin-5-yl)-ethyl methanesulfonate with piperidine-4-carboxylic acid tert-butyl ester.

The starting material can be prepared, for example, as follows:

a) 2,3-Dimethoxy-7-nitro-5-vinyl-quinoxaline

A mixture of 3.14 g (1 mmol) of 5-bromo-2,3-dimethoxy-7-nitro-quinoxaline, 6.34 g (2 mmol) of tributylvinylstannane, 1.26 g (3 mmol) of lithium chloride and 1.4 g (0.2 mmol) of bis(triphenylphosphine)-palladium (II) chloride in 20 ml of dimethylformamide is heated for 2 hours at 100° C. The mixture is cooled to room temperature and concentrated to dryness by evaporation under reduced pressure. Purification by flash chromatography using toluene as eluant yields the title compound in the form of a slightly yellowish solid.

b) 2-(2,3-Dimethoxy-7-nitro-quinoxalin-5-yl)-ethanol

The title compound is obtained by customary hydroboration, for example with the dimethyl sulfide/borane complex.

c) 2-(2,3-Dimethoxy-7-nitro-quinoxalin-5-yl)-ethyl methanesulfonate

The title compound is obtained by customary reaction with methanesulfonyl chloride.

EXAMPLE 73

1-[2-(7-Nitro-2,3-dioxo-1,2,3,4-tetrahydro-quinoxalin-5-yl)-ethyl]-piperidine-4-carboxylic acid The title compound can be prepared in a manner analogous to that described in Example 6 but starting from 1-[2-(7-nitro-2,3-dioxo-1,2,3,4-tetrahydro-quinoxalin-5-yl)-ethyl]-piperidine-4-carboxylic acid tert-butyl ester.

EXAMPLE 74

2-[2-(7-Nitro-2,3-dioxo-1,2,3,4-tetrahydro-quinoxalin-5-yl)-ethylamino]-propionic acid methyl ester The title compound is obtained in a manner analogous to that described in Example 72 but starting from alanine methyl ester.

EXAMPLE 75

2-[2-(7-Nitro-2,3-dioxo-1,2,3,4-tetrahydro-quinoxalin-5-yl)-ethylamino]-propionic acid The title compound can be prepared in a manner analogous to that described in Example 22 but starting from 2-[2-(7-nitro-2,3-dioxo-1,2,3,4-tetrahydro-quinoxalin-5-yl)-ethylamino]-propionic acid methyl ester hydrochloride.

EXAMPLE 76

2-Amino-3-(7-nitro-2,3-dioxo-1,2,3,4-tetrahydro-quinoxalin-5-yl)-propionic acid

A suspension of 0.29 g (0.62 mmol) of 2-acetylamino-2-(2,3-dimethoxy-7-nitro-quinoxalin-5-ylmethyl)-malonic acid diethyl ester in 6 ml of 6N hydrochloric acid is heated at reflux for 24 hours and then concentrated to dryness under reduced pressure. After boiling the residue up with water, centrifugation and drying, the title compound is obtained in the form of a yellow powder.

$^1$H-NMR (DMSO-$D_6$): δ 12.3–11.9 (br, 2H), 10.3–9.2 (br), 7.98 (d, J=3 Hz, 1H), 7.90 (d, J=3 Hz, 1H), 3.50–3.45 (m, 1H), 3.40–3.32 (m, 1H), 3.06–2.98 (m, 1H). (ES+)-MS: [M+Na+NH$_4$]$^+$

The starting material can be prepared as follows:

a) 2-Acetylamino-2-(2,3-dimethoxy-7-nitro-quinoxalin-5-ylmethyl)-malonic acid diethyl ester 0.217 g (1 mmol) of diethylacetamido malonate is added to a solution, stirred under argon, of 0.026 g (1.2 mmol) of sodium in 3 ml of ethanol. After 5 minutes, 0.328 g (1 mmol) of 2,3-dimethoxy-5-bromomethyl-7-nitro-quinoxaline is added and the mixture is then stirred for 18 hours at 25° C. The mixture is diluted with ethyl acetate, washed with 1 N hydrochloric acid and then with brine, dried over sodium sulfate and concentrated by rotary evaporation. Chromatography on silica gel using ethyl acetate/hexane (1:2) as eluant yields the title compound in the form of an oil that soon solidifies.

TLC (EtOAc/hexane 1:2): $R_f$=0.35 $^1$H-NMR (CDCl$_3$): δ 8.57 (d, J=3 Hz, 1H), 8.01 (d, J=3 Hz, 1H), 6.34 (s, 1H), 4.36–4.24 (m, 4H), 4.25 (s, 3H), 4.18 (s, 3H), 1.85 (s, 3H), 1.31 (t, J=7 Hz, 6H).

EXAMPLE 77

3-Amino-3-(7-nitro-2,3-dioxo-1,2,3,4-tetrahydro-quinoxalin-5-yl)-propionic acid hydrobromide A solution of 0.15 g (0.39 mmol) of 3-(2,3-dimethoxy-7-nitro-quinoxalin-5-yl)-3-methoxy-carbonylamino-propionic acid in 5 ml of 33% HBr/HOAc is heated for 16 hours at 70° C. After cooling, the grey suspension is diluted with tert-butyl methyl ether and filtered with suction. The title compound is obtained in the form of a grey powder.

$^1$H-NMR (DMSO-$D_6$): δ 12.41 (s,1H), 12.4–11.8 (br, 1H), 8.7–8.3 (br, NH3$^+$), 5.4–5.28 (m, 2H), 3.16–2.96 (m, 2H); FAB-MS: [M+1]$^+$295.

The starting material can be prepared as follows:

a) Methyl [1-(2,3-dimethoxy-7-nitro-quinoxalin-5-yl)-but-3-enyl]carbamate SV-2560

1.26 ml of BF$_3$.OEt$_2$ are added all at once to a suspension, stirred at 0° C., of 2.63 g (10 mmol) of 2,3-dimethoxy-7-nitro-quinoxaline-5-carbaldehyde, 0.75 g (10 mmol) of methyl carbamate and 1.2 g (10.5 mmol) of allyltrimethylsilane in 30 ml of acetonitrile. The mixture is stirred for 30 minutes at 25° C., and is then poured onto 10% aqueous sodium hydrogen carbonate solution and diluted with brine and ethyl acetate. The organic phase is separated off, dried and concentrated by rotary evaporation. Crystallization of the crude product yields the title compound in the form of almost colorless crystals; m.p.=135–136° C.

TLC (EtOAc/hexane 1:3): $R_f$=0.17.

b) 3-(2,3-Dimethoxy-7-nitro-quinoxalin-5-yl)-3-methoxycarbonylamino-propionic acid A mixture of 0.31 g (0.85 mmol) of methyl [1-(2,3-dimethoxy-7-nitro-quinoxalin-5-yl)-but-3-enyl]carbamate, 0.733 9 (3.42 mmol) of sodium iodate (NaIO$_4$) and 0.01 g of ruthenium oxide (RuO$_2$) in 5 ml of acetonitrile, 5 ml of carbon tetrachloride and 5 ml of water is stirred vigorously for 4 hours at 25° C. The mixture is then filtered off over High-Flow® and then washed with ethyl acetate and water. The organic phase is washed in succession with 1 N hydrochloric acid and brine, dried over sodium sulfate and concentrated by rotary evaporation. The residue is again mixed with 0.50 g of sodium iodate, 0.005 g of ruthenium oxide in a mixture of 5 ml of water, 5 ml of acetonitrile and 5 ml of carbon tetrachloride and is stirred vigorously for a further 1 hour. The mixture is filtered over High-Flow®, then washed with ethyl acetate and water. The organic phase is separated off, washed with brine, dried over sodium sulfate and concentrated by rotary evaporation. Crystallization of the crude product from tert-butyl methyl ether yields the title compound in the form of grey crystals. TLC (EtOAc/HOAc 98:2): $R_f$=0.52. $^1$H-NMR (CDCl$_3$): δ 8.61 (d, J=3 Hz, 1H), 8.32 (d, J=3 Hz, 1H), 6.36–6.28 (m, 1H), 6.02–5.88 (m, 1H), 4.23 (s, 3H), 4.19 (s, 3H), 3.68 (s, 3H), 3.18–3.09 (m, 2H).

EXAMPLE 78

The following can also be prepared in a manner analogous to that described in Examples 1 to 77:

N-(2,3-dioxo-7-nitro-1,2,3,4-tetrahydroquinoxalin-5-ylmethyl)-4-trifluoromethylpiperidine hydrobromide, m.p.=273° C. (decomp.);

N-(2,3-dioxo-7-nitro-1,2,3,4-tetrahydroquinoxalin-5-ylmethyl)-2-aminobenzimidazole hydrobromide, m.p.>300° C.;

N-(2,3-dioxo-7-nitro-1,2,3,4-tetrahydroquinoxalin-5-ylmethyl)-diisopropylamine hydrobromide, m.p.=284° C. (decomp.);

N-(2,3-dioxo-7-nitro-1,2,3,4-tetrahydroquinoxalin-5-ylmethyl)-4-n-propylpiperidine hydrobromide, m.p.=286° C.;

N-(2,3-dioxo-7-nitro-1,2,3,4-tetrahydroquinoxalin-5-ylmethyl)-4-amino-n-butylphosphonic acid hydrobromide, MS(ES+): (M+H)$^+$=373;

N-(2,3-dioxo-7-nitro-1,2,3,4-tetrahydroquinoxalin-5-ylmethyl)-N-methyl-4-amino-n-butyl-phosphonic acid hydrobromide, MS(ES+): (M+H)+=387;

N-(2,3-dioxo-7-nitro-1,2,3,4-tetrahydroquinoxalin-5-ylmethyl)-N-methyl-12-amino-n-dodecanoic acid, m.p.=232–238° C. (decomp.);

N-(7-nitro-2,3-dioxo-1,2,3,4-tetrahydroquinoxalin-5-ylmethyl)-4-hydroxy-3-methoxy-benzylamine, m.p.>270° C.;

N-[1-(7-nitro-2,3-dioxo-1,2,3,4-tetrahydroquinoxalin-5-ylmethyl)-piperidin-4-yl-methyl]-methanesulfonamide hydrobromide, (ES)-MS: 410 [M–H];

N-[1-(7-nitro-2,3-dioxo-1,2,3,4-tetrahydroquinoxalin-5-ylmethyl)-piperidin-4-yl-methyl]-acetamide hydrobromide, (ES)-MS: 374 [M–H];

N-[1-(7-nitro-2,3-dioxo-1,2,3,4-tetrahydroquinoxalin-5-ylmethyl)-piperidin-4-yl-methyl]-nicotinamide bishydrobromide, (ES)-MS: 437 [M–H];

N-(7-nitro-2,3-dioxo-1,2,3,4-tetrahydroquinoxalin-5-ylmethyl)-4-(4-fluorobenzoyl)-piperidine, (AP)-MS: 425 [M–H];

{3-[(7-nitro-2,3-dioxo-1,2,3,4-tetrahydroquinoxalin-5-ylmethyl)-amino]-2-oxo-2,3,4,5-tetrahydro-benzo[.b.]azepin-1-yl}-acetic acid hydrobromide, (ES$^+$)-MS: 454 [M+H]$^+$;

4-(7-nitro-2,3-dioxo-1,2,3,4-tetrahydroquinoxalin-5-ylmethyl)-piperazine-2-carboxylic acid;

N-(7-nitro-2,3-dioxo-1,2,3,4-tetrahydroquinoxalin-5-ylmethyl)-(3-chloro-phenyl)-sulfonamide, m.p.>270° C.;

N-(7-nitro-2,3-dioxo-1,2,3,4-tetrahydroquinoxalin-5-ylmethyl)-(3-carboxy-phenyl)-sulfonamide, m.p.>270° C.;

4-(7-nitro-2,3-dioxo-1,2,3,4-tetrahydroquinoxalin-5-ylmethyl)-4-methyl-3,5-dioxo-piperazine, (AP)-MS: 346 [M–H];

4-{[(7-nitro-2,3-dioxo-1,2,3,4-tetrahydroquinoxalin-5-ylmethyl)-amino]-methyl}-benzenesulfonamide hydrochloride, m.p.>270° C.;

N-(7-nitro-2,3-dioxo-1,2,3,4-tetrahydroquinoxalin-5-ylmethyl)-2-oxo-azepin-3-yl-amine hydrobromide, m.p.>270° C.;

4-{[(7-nitro-2,3-dioxo-1,2,3,4-tetrahydroquinoxalin-5-ylmethyl)-amino]-methyl}-benzoic acid hydrochloride, m.p.>270° C.;

4-[(7-nitro-2,3-dioxo-1,2,3,4-tetrahydroquinoxalin-5-ylmethyl)-amino]-benzoic acid hydrochloride, m.p.>270° C.;

5-[(7-nitro-2,3-dioxo-1,2,3,4-tetrahydroquinoxalin-5-ylmethyl)-amino]-3H-imidazole-4-carboxylic acid amide, m.p.>270° C.;

N-(7-nitro-2,3-dioxo-1,2,3,4-tetrahydroquinoxalin-5-ylmethyl)-3,5-dimethyl-morpholine hydrobromide, m.p.>300° C.;

N-(7-nitro-2,3-dioxo-1,2,3,4-tetrahydroquinoxalin-5-ylmethyl)-4,4-ethylenedioxy-piperidine hydrochloride, m.p.=290° C. (decomp.);

N-(7-nitro-2,3-dioxo-1,2,3,4-tetrahydroquinoxalin-5-ylmethyl)-3-methyl-piperidine hydrobromide, m.p.>300° C. (decomp.);

N-(7-nitro-2,3-dioxo-1,2,3,4-tetrahydroquinoxalin-5-ylmethyl)-4-hydroxy-piperidine hydrochloride, m.p.=290° C. (decomp.);

N-(7-nitro-2,3-dioxo-1,2,3,4-tetrahydroquinoxalin-5-ylmethyl)-2-hydroxymethyl-pyrrolidine hydrochloride, m.p.=247° C. (decomp.);

N-(7-nitro-2,3-dioxo-1,2,3,4-tetrahydroquinoxalin-5-ylmethyl)-2-acetoxymethyl-pyrrolidine hydrobromide, m.p.=175° C. (decomp.);

N-(7-nitro-2,3-dioxo-1,2,3,4-tetrahydroquinoxalin-5-ylmethyl)-4-hydroxy-pyrrolidine-2-carboxylic acid hydrochloride, m.p.=241° C. (decomp.);

N-(7-nitro-2,3-dioxo-1,2,3,4-tetrahydroquinoxalin-5-ylmethyl)-3-hydroxy-piperidine hydrochloride, m.p.>300° C.;

2-(7-nitro-2,3-dioxo-1,2,3,4-tetrahydroquinoxalin-5-ylmethylamino)-(L)-butyric acid hydrochloride, m.p.=238° C. (decomp.);

2-(7-nitro-2,3-dioxo-1,2,3,4-tetrahydroquinoxalin-5-ylmethylamino)-(L)-butyric acid methyl ester hydrobromide, m.p.=218° C. (decomp.);

2-(7-nitro-2,3-dioxo-1,2,3,4-tetrahydroquinoxalin-5-ylmethylamino)-isobutyric acid hydrochloride, m.p.>300° C.;

2-(7-nitro-2,3-dioxo-1,2,3,4-tetrahydroquinoxalin-5-ylmethylamino)-isobutyric acid methyl ester hydrobromide, m.p.=243° C. (decomp.);

1-(7-nitro-2,3-dioxo-1,2,3,4-tetrahydroquinoxalin-5-ylmethylamino)-cyclopropane-1-carboxylic acid hydrochloride, m.p.=254° C. (decomp.);

N-[N-(7-nitro-2,3-dioxo-1,2,3,4-tetrahydroquinoxalin-5-ylmethyl)-N-methyl)-(L)-alanine hydrochloride, m.p.=277° C. (decomp.);

N-(7-nitro-2,3-dioxo-1,2,3,4-tetrahydroquinoxalin-5-ylmethyl)-leucine;

N-(7-nitro-2,3-dioxo-1,2,3,4-tetrahydroquinoxalin-5-ylmethyl)-(L)-threonine hydrobromide, m.p.=215° C. (decomp.);

N-(7-nitro-2,3-dioxo-1,2,3,4-tetrahydroquinoxalin-5-ylmethyl)-2-methyl-β-alanine hydrochloride, m.p.=238° C. (decomp.);

N-(7-nitro-2,3-dioxo-1,2,3,4-tetrahydroquinoxalin-5-ylmethyl)-4-picolylamine dihydrobromide, m.p.=218° C. (decomp.);

N-(7-nitro-2,3-dioxo-1,2,3,4-tetrahydroquinoxalin-5-ylmethyl)-2-picolytamine dihydrobromide, m.p.=229° C. (decomp.);

N-(7-nitro-2,3-dioxo-1,2,3,4-tetrahydroquinoxalin-5-ylmethyl)-aminoacetonitrile hydrobromide, m.p.=275° C. (decomp.);

N-(7-nitro-2,3-dioxo-1,2,3,4-tetrahydroquinoxalin-5-ylmethyl)-4-benzylidenepiperidine hydrobromide, m.p.=242° C. (decomp.);

N-(7-nitro-2,3-dioxo-1,2,3,4-tetrahydroquinoxalin-5-ylmethyl)-4-phenylpiperidine-4-carboxylate hydrochloride, m.p.>280° C.;

N-(7-nitro-2,3-dioxo-1,2,3,4-tetrahydroquinoxalin-5-ylmethyl)-4-carbamoylpiperidine hydrobromide, m.p.>300° C.;

N-(7-nitro-2,3-dioxo-1,2,3,4-tetrahydroquinoxalin-5-ylmethyl)-3-methyl-β-alanine hydrochloride, m.p.=298° C. (decomp.);

N-(7-nitro-2,3-dioxo-1,2,3,4-tetrahydroquinoxalin-5-ylmethyl)-4-phenyl-4-methoxycarbonyl-piperidine hydrobromide, m.p.=258° C. (decomp.);

N-(7-nitro-2,3-dioxo-1,2,3,4-tetrahydroquinoxalin-5-ylmethyl)-iminodiacetic acid hydrochloride, m.p.=257° C. (decomp.);

N-(7-nitro-2,3-dioxo-1,2,3,4-tetrahydroquinoxalin-5-ylmethyl)-1,2,3,4-tetrahydroisoquinoline hydrobromide, m.p.=300° C. (decomp.);

N-(7-nitro-2,3-dioxo-1,2,3,4-tetrahydroquinoxalin-5-ylmethyl)-2-aminobenzothiazole hydrobromide, m.p.=272° C. (decomp.);

1-(7-nitro-2,3-dioxo-1,2,3,4-tetrahydroquinoxalin-5-ylmethylamino)ethanephosphonic acid;

N-(7-nitro-2,3-dioxo-1,2,3,4-tetrahydroquinoxalin-5-ylmethyl)-N-acetyl-(L)-alanine;

N-(7-nitro-2,3-dioxo-1,2,3,4-tetrahydroquinoxalin-5-ylmethyl)-4-phenyl-piperidine hydrobromide, m.p.>230° C.;

N-(7-nitro-2,3-dioxo-1,2,3,4-tetrahydroquinoxalin-5-ylmethyl)-4-hydroxymethyl-piperidine hydrochloride, m.p.=248° C. (decomp.);

N-(7-nitro-2,3-dioxo-1,2,3,4-tetrahydroquinoxalin-5-ylmethyl)-2-hydroxymethylpiperidine hydrochloride, m.p.=286° C. (decomp.);

N-(7-nitro-2,3-dioxo-1,2,3,4-tetrahydroquinoxalin-5-ylmethyl)-4-(1-hydroxyethyl)-piperidine hydrochloride, m.p.=238° C. (decomp.);

N-(7-nitro-2,3-dioxo-1,2,3,4-tetrahydroquinoxalin-5-ylmethyl)-4-methoxy-piperidine hydrochloride, m.p.>300° C.;

N-(7-nitro-2,3-dioxo-1,2,3,4-tetrahydroquinoxalin-5-ylmethyl)-2-methyl-piperdine;

N-(7-nitro-2,3-dioxo-1,2,3,4-tetrahydroquinoxalin-5-ylmethyl)-4-methoxy-4-methyl-piperidine;

N-(7-nitro-2,3-dioxo-1,2,3,4-tetrahydroquinoxalin-5-ylmethyl)-4,4-dimethoxy-piperidine;

N-(7-nitro-2,3-dioxo-1,2,3,4-tetrahydroquinoxalin-5-ylmethyl)-(L)-serine hydrochloride, m.p.=228° C. (decomp.);

N-(7-nitro-2,3-dioxo-1,2,3,4-tetrahydroquinoxalin-5-ylmethyl)-O-acetyl-(L)-serine hydrobromide, m.p.=250° C. (decomp.);

N-(7-nitro-2,3-dioxo-1,2,3,4-tetrahydroquinoxalin-5-ylmethyl)-azepin-2-one;

N-(7-nitro-2,3-dioxo-1,2,3,4-tetrahydroquinoxalin-5-ylmethyl)-piperidin-2-one;

1-(7-nitro-2,3-dioxo-1,2,3,4-tetrahydroquinoxalin-5-ylmethyl)-2-ethyl-4-methyl-imidazole;

N-(7-nitro-2,3-dioxo-1,2,3,4-tetrahydroquinoxalin-5-ylmethyl)-4-oxo-pyrrolidine-2-carboxylic acid;

N-(7-nitro-2,3-dioxo-1,2,3,4-tetrahydroquinoxalin-5-yl methyl)-2-amino-5-bromo-pyrimidine hydrobromide, m.p.>274° C.;

N-(7-nitro-2,3-dioxo-1,2,3,4-tetrahydroquinoxalin-5-yl methyl)-5-amino-2-methoxy-pyridine hydrobromide, m.p.>300° C.;

N-(7-nitro-2,3-dioxo-1,2,3,4-tetrahydroquinoxalin-5-yl methyl)-2-aminopyrimidine hydrobromide, m.p.>300° C.;

N-(7-nitro-2,3-dioxo-1,2,3,4-tetrahydroquinoxalin-5-yl methyl)-2-amino-pyridine hydrobromide, m.p.>300° C.;

N-(7-nitro-2,3-dioxo-1,2,3,4-tetrahydroquinoxalin-5-yl methyl)-3-amino-pyridine hydrobromide, m.p.=213° C. (decomp.);

N-(7-nitro-2,3-dioxo-1,2,3,4-tetrahydroquinoxalin-5-yl methyl)-2-amino-4-methyl-pyrimidine hydrobromide, m.p.=200° C. (decomp.);

N-(7-nitro-2,3-dioxo-1,2,3,4-tetrahydroquinoxalin-5-yl methyl)-3-amino-5-tert-butylisoxazole, m.p.=148–150° C. (decomp.);

N-(7-nitro-2,3-dioxo-1,2,3,4-tetrahydroquinoxalin-5-yl methyl)-2-amino-4,5-dicyano-imidazole hydrobromide, m.p.>300° C.;

N-(7-nitro-2,3-dioxo-1,2,3,4-tetrahydroquinoxalin-5-yl methyl)-N,N,N-triethyl-ammonium bromide;

1-(7-nitro-2,3-dioxo-1,2,3,4-tetrahydroquinoxalin-5-ylmethyl)-1,2,4-triazole-3-carboxylic acid;

1-(7-nitro-2,3-dioxo-1,2,3,4-tetrahydroquinoxalin-5-ylmethyl)-1,2,4-trazole-5-carboxylic acid;

4-(7-nitro-2,3-dioxo-1,2,3,4-tetrahydroquinoxalin-5-ylmethyl)-1,2,4-triazole-3-carboxylic acid;

1-(7-nitro-2,3-dioxo-1,2,3,4-tetrahydroquinoxalin-5-ylmethyl)-1,2,3-triazole-4,5-dicarboxylic acid;

1-(7-nitro-2,3-dioxo-1,2,3,4-tetrahydroquinoxalin-5-ylmethyl)-1,2,4-triazole;

1-(7-nitro-2,3-dioxo-1,2,3,4-tetrahydroquinoxalin-5-ylmethyl)-1,2,4-triazole-5-carboxylic acid ethyl ester;

2-(7-nitro-2,3-dioxo-1,2,3,4-tetrahydroquinoxalin-5-ylmethyl)-1,2,3-triazole-4,5-dicarboxylic acid;

1-(7-nitro-2,3-dioxo-1,2,3,4-tetrahydroquinoxalin-5-ylmethyl)-1,2,3-triazole-4,5-dicarboxylic acid dimethyl ester;

1-(7-nitro-2,3-dioxo-1,2,3,4-tetrahydroquinoxalin-5-ylmethyl)-1,2,3-triazole-4-carboxylic acid amide;

1-(chloro-2,3-dioxo-1,2,3,4-tetrahydroquinoxalin-5-ylmethyl)-1,2,3-triazole-4-carboxylic acid amide;

1-(7-nitro-2,3-dioxo-1,2,3,4-tetrahydroquinoxalin-5-ylmethyl)-1,2,3-triazole-4,5-dicarboxylic acid dimethyl ester, m.p.=173–175° C.;

2-(7-nitro-2,3-dioxo-1,2,3,4-tetrahydroquinoxalin-5-ylmethyl)-1,2,3-triazole-4,5-dicarboxylic acid, m.p.=290° C. (decomp.);

1-(7-nitro-2,3-dioxo-1,2,3,4-tetrahydroquinoxalin-5-ylmethyl)-imidazole-2,4,5-tricarboxylic acid;
P-benzyl-(7-nitro-2,3-dioxo-1,2,3,4-tetrahydroquinoxalin-5-yl)-methanephosphinic acid;
P-methyl-(7-nitro-2,3-dioxo-1,2,3,4-tetrahydroquinoxalin-5-yl)-methanephosphinic acid;
N-(7-nitro-2,3-dioxo-1,2,3,4-tetrahydroquinoxalin-5-yl)-carbamoylmethanephosphonic acid;
1-(7-nitro-2,3-dioxo-1,2,3,4-tetrahydroquinoxalin-5-ylmethyl)-2-oxo-1,2-dihydropyridine;
2-(7-nitro-2,3-dioxo-1,2,3,4-tetrahydroquinoxalin-5-ylmethyl)-1,2,3,4-tetrahydroisoquinolin-1-one;
1-(7-nitro-2,3-dioxo-1,2,3,4-tetrahydroquinoxalin-5-ylmethyl)-2,3,4,5-tetrahydro-1H-1-benzazepin-2-one;
N-(7-nitro-2,3-dioxo-1,2,3,4-tetrahydroquinoxalin-5-ylmethyl)-2-oxo-3-phenyl-piperidine;
N-(7-nitro-2,3-dioxo-1,2,3,4-tetrahydroquinoxalin-5-ylmethyl)-2-oxo-5-phenyl-piperidine;
N-(7-nitro-2,3-dioxo-1,2,3,4-tetrahydroquinoxalin-5-ylmethyl)-5-methyl-pyrrolidin-2-one;
4-(2-oxoimidazolidin-1-yl)-N-(7-nitro-2,3-dioxo-1,2,3,4-tetrahydroquinoxalin-5-ylmethyl)piperidine;
N-{2-[N-(7-nitro-2,3-dioxo-1,2,3,4-tetrahydroquinoxalin-5-ylmethyl)amino]ethyl}-pyrrolidin-2-one;
N-(7-nitro-2,3-dioxo-1,2,3,4-tetrahydroquinoxalin-5-ylmethyl)-3-phenyl-pyrrolidin-2-one;
N-(7-nitro-2,3-dioxo-1,2,3,4-tetrahydroquinoxalin-5-ylmethyl)-4-(4-fluorobenzoyl)-piperidine;
N-(7-bromo-2,3-dioxo-1,2,3,4-tetrahydroquinoxalin-5-ylmethyl)-2-oxo-2-phenyl-acetamide;
N-(7-bromo-2,3-dioxo-1,2,3,4-tetrahydroquinoxalin-5-ylmethyl)-2-propyl-pentanoic acid amide;
N-(7-bromo-2,3-dioxo-1,2,3,4-tetrahydroquinoxalin-5-ylmethyl)-(4-methylfuran)-2-carboxylic acid amide;
N-(7-bromo-2,3-dioxo-1,2,3,4-tetrahydroquinoxalin-5-ylmethyl)-thiophene-3-carboxylic acid amide, m.p.>250° C.;
N-(7-bromo-2,3-dioxo-1,2,3,4-tetrahydroquinoxalin-5-ylmethyl)-imidazole-4-carboxylic acid amide;
N-(7-bromo-2,3-dioxo-1,2,3,4-tetrahydroquinoxalin-5-ylmethyl)-3-(thien-3-yl)-acrylic acid amide;
N-(7-bromo-2,3-dioxo-1,2,3,4-tetrahydroquinoxalin-5-ylmethyl)-2-phenylisobutyric acid amide;
N-(7-bromo-2,3-dioxo-1,2,3,4-tetrahydroquinoxalin-5-ylmethyl)-1-phenylcyclopropane-carboxylic acid amide;
N-(7-bromo-2,3-dioxo-1,2,3,4-tetrahydroquinoxalin-5-ylmethyl)-2-phenylpropionic acid amide;
N-(7-bromo-2,3-dioxo-1,2,3,4-tetrahydroquinoxalin-5-ylmethyl)-2-phenylglycolic acid amide;
N-(7-bromo-2,3-dioxo-1,2,3,4-tetrahydroquinoxalin-5-yimethyl)-(3,4-dimethoxyphenyl)-acetamide, m.p.>280° C.;
N-(7-bromo-2,3-dioxo-1,2,3,4-tetrahydroquinoxalin-5-ylmethyl)-(4-chlorophenyl)acetamide;
N-(7-bromo-2,3-dioxo-1,2,3,4-tetrahydroquinoxalin-5-ylmethyl)-(3-chlorophenyl)acetamide;
N-(7-bromo-2,3-dioxo-1,2,3,4-tetrahydroquinoxalin-5-ylmethyl)-(2-chlorophenyl)acetamide;
N-(7-bromo-2,3-dioxo-1,2,3,4-tetrahydroquinoxalin-5-ylmethyl)-(3-methylthiophene)-2-carboxylic acid amide, m.p.>280° C.;
N-(7-bromo-2,3-dioxo-1,2,3,4-tetrahydroquinoxalin-5-ylmethyl)-(5-methylthiophene)-2-carboxylic acid amide, m.p.>280° C.;
N-(7-bromo-2,3-dioxo-1,2,3,4-tetrahydroquinoxalin-5-ylmethyl)-(1-methylpyrrole)-2-carboxylic acid amide, m.p.>280° C.;
N-(7-bromo-2,3-dioxo-1,2,3,4-tetrahydroquinoxalin-5-ylmethyl)-nicotinic acid amide hydrochloride, m.p.=272° C. (decomp.);
N-(7-bromo-2,3-dioxo-1,2,3,4-tetrahydroquinoxalin-5-ylmethyl)-(4-nitrophenyl)acetamide, m.p.>270° C.;
N-(7-bromo-2,3-dioxo-1,2,3,4-tetrahydroquinoxalin-5-yl methyl)-(3-nitrophenyl)acetamide, m.p.>270° C.;
N-(7-bromo-2,3-dioxo-1,2,3,4-tetrahydroquinoxalin-5-ylmethyl)-(2-nitrophenyl)acetamide, m.p.>270° C.;
N-(7-bromo-2,3-dioxo-1,2,3,4-tetrahydroquinoxalin-5-ylmethyl)-(3,4-methylenedioxyphenyl)acetamide, m.p.>270° C.;
N-(7-bromo-2,3-dioxo-1,2,3,4-tetrahydroquinoxalin-5-ylmethyl)-(3-phenyloxyphenyl)acetamide;
N-(7-bromo-2,3-dioxo-1,2,3,4-tetrahydroquinoxalin-5-ylmethyl)-picolinic acid amide;
7-bromo-2,3-dioxo-1,2,3,4-tetrahydroquinoxalin-5-ylmethylaminomethanephosphonic acid, m.p.>270° C.;
1-(7-bromo-2,3-dioxo-1,2,3,4-tetrahydroquinoxalin-5-ylmethylamino)ethanephosphonic acid;
N-(7-bromo-2,3-dioxo-1,2,3,4-tetrahydroquinoxalin-5-ylmethyl)-N-benzyloxycarbonyl-aminomethanephosphonic acid;
N-(7-bromo-2,3-dioxo-1,2,3,4-tetrahydroquinoxalin-5-ylmethyl)benzylurethane;
N-(7-bromo-2,3-dioxo-1,2,3,4-tetrahydroquinoxalin-5-ylmethyl)-phenylurethane;
N-(7-bromo-2,3-dioxo-1,2,3,4-tetrahydroquinoxalin-5-ylmethyl)-N-phenylacetyl-aminomethanephosphonic acid;
N-(7-bromo-2,3-dioxo-1,2,3,4-tetrahydroquinoxalin-5-ylmethyl)-N-phenylacetyl-glycine;
3-acetyl-1-(7-nitro-2,3-dioxo-1,2,3,4-tetrahydroquinoxalin-5-ylmethyl)-pyrrole hydrobromide, m.p.=225° C. (decomp.);
1-(7-nitro-2,3-dioxo-1,2,3,4-tetrahydroquinoxalin-5-ylmethyl)-pyrrole-3-carboxylic acid ethyl ester hydrobromide, m.p.=195° C. (decomp.);
N-methyl-N-(7-bromo-2,3-dioxo-1,2,3,4-tetrahydroquinoxalin-5-ylmethyl)-phenylacetamide, m.p.>260° C.;
N-(7-bromo-2,3-dioxo-1,2,3,4-tetrahydroquinoxalin-5-ylmethyl)-3-acetoxypyrrolidine hydrobromide, m.p.=246° C.;
N-(7-bromo-2,3-dioxo-1,2,3,4-tetrahydroquinoxalin-5-yimethyl)-3-hydroxypyrrolidine hydrochloride, m.p.=263° C.;
1-(7-nitro-2,3-dioxo-1,2,3,4-tetrahydroquinoxalin-5-ylmethyl)-pyrrole-3-carboxylic acid;
1-(7-nitro-2,3-dioxo-1,2,3,4-tetrahydroquinoxalin-5-ylmethyl)-pyrrole-2-carboxylic acid;
1-(7-nitro-2,3-dioxo-1,2,3,4-tetrahydroquinoxalin-5-ylmethyl)-pyrrole-2-carboxylic acid tert-butyl ester;
1-(7-nitro-2,3-dioxo-1,2,3,4-tetrahydroquinoxalin-5-ylmethyl)-indol-3-ylacetic acid;
1-(7-nitro-2,3-dioxo-1,2,3,4-tetrahydroquinoxalin-5-ylmethyl)-indol-3-ylacetic acid ethyl ester;
1-(7-nitro-2,3-dioxo-1,2,3,4-tetrahydroquinoxalin-5-ylmethyl)-indo-3-ylcarboxylic acid;
1-(7-nitro-2,3-dioxo-1,2,3,4-tetrahydroquinoxalin-5-ylmethyl)-indole-2-carboxylic acid tert-butyl ester;
1-(7-nitro-2,3-dioxo-1,2,3,4-tetrahydroquinoxalin-5-ylmethyl)-indole-2-carboxylic acid;
1-(7-nitro-2,3-dioxo-1,2,3,4-tetrahydroquinoxalin-5-yimethyl)-imidazole hydrobromide, m.p.>300° C.;
1-(7-nitro-2,3-dioxo-1,2,3,4-tetrahydroquinoxalin-5-ylmethyl)-4-hydroxymethyl-imidazole;

1-[1-(7-nitro-2,3-dioxo-1,2,3,4-tetrahydroquinoxalin-5-ylmethyl)imidazol-4-yl]acetic acid;
1-(7-nitro-2,3-dioxo-1,2,3,4-tetrahydroquinoxalin-5-ylmethyl)-4-methyl-imidazole hydrobromide, m.p.>300° C.;
1-(7-nitro-2,3-dioxo-1,2,3,4-tetrahydroquinoxalin-5-ylmethyl)-2-methyl-imidazole hydrobromide, m.p.>300° C,;
1-(7-nitro-2,3-dioxo-1,2,3,4-tetrahydroquinoxalin-5-ylmethyl)-2-ethyl-imidazole hydrobromide, m.p.>300° C.;
1-(7-nitro-2,3-dioxo-1,2,3,4-tetrahydroquinoxalin-5-ylmethyl)pyrazole hydrobromide, m.p.>300° C.;
1-(7-nitro-2,3-dioxo-1,2,3,4-tetrahydroquinoxalin-5-ylmethyl)-3,5-dimethyl-pyrazole hydrobromide, m.p.>300° C.;
2-(7-nitro-2,3-dioxo-1,2,3,4-tetrahydroquinoxalin-5-ylmethyl)-1,2,4-triazole hydrobromide, m.p.>250° C.;
1-(7-nitro-2,3-dioxo-1,2,3,4-tetrahydroquinoxalin-5-ylmethyl)pyrrole;
1-(7-nitro-2,3-dioxo-1,2,3,4-tetrahydroquinoxalin-5-ylmethyl)-piperazin-3-one;
1-(7-nitro-2,3-dioxo-1,2,3,4-tetrahydroquinoxalin-5-ylmethyl)-oxazolidin-2-one;
1-(7-nitro-2,3-dioxo-1,2,3,4-tetrahydroquinoxalin-5-ylmethyl)-4-methyl-piperazine-3,5-dione;
3-(7-nitro-2,3-dioxo-1,2,3,4-tetrahydroquinoxalin-5-ylmethyl)-2,3,5,6-tetrahydro-4H-1,2-oxazine;
N-(7-nitro-2,3-dioxo-1,2,3,4-tetrahydroquinoxalin-5-ylmethyl)-anthranilic acid;
N-(7-nitro-2,3-dioxo-1,2,3,4-tetrahydroquinoxalin-5-ylmethyl)-anthranilic acid methyl ester;
N-(7-nitro-2,3-dioxo-1,2,3,4-tetrahydroquinoxalin-5-ylmethyl)-anthranilic acid ethyl ester;
1-(7-nitro-2,3-dioxo-1,2,3,4-tetrahydroquinoxalin-5-ylmethyl)-2-benzyl-4-acetylamino-piperidine;
1-(7-nitro-2,3-dioxo-1,2,3,4-tetrahydroquinoxalin-5-ylmethyl)-2-phenyl-4-acetylamino-piperidine;
{3-(7-nitro-2,3-dioxo-1,2,3,4-tetrahydroquinoxalin-5-ylmethylamino)-2-oxo-1,2,3,4-tetrahydro-benzo[b]azepin-1-yl}-acetic acid;
N-(7-nitro-2,3-dioxo-1,2,3,4-tetrahydroquinoxalin-5-ylmethyl)-N-isopropyl-N-(quinolin-4-ylmethyl)-amine;
4-(7-nitro-2,3-dioxo-1,2,3,4-tetrahydroquinoxalin-5-ylmethylamino)-5-phenyl-pent-1-ene;
2-(7-nitro-2,3-dioxo-1,2,3,4-tetrahydroquinoxalin-5-ylmethyl)-N-(4-nitrophenyl)-acetamide;
N-[N-(7-nitro-2,3-dioxo-1,2,3,4-tetrahydroquinoxalin-5-ylmethyl)glycyl]glycine;
N-[N-(7-nitro-2,3-dioxo-1,2,3,4-tetrahydroquinoxalin-5-ylmethyl)glycyl]-N-methyl-glycine;
1-[N-(7-nitro-2,3-dioxo-1,2,3,4-tetrahydroquinoxalin-5-ylmethyl)glycyl]-pyrrolidine-2-carboxylic acid;
N-[N-(7-nitro-2,3-dioxo-1,2,3,4-tetrahydroquinoxalin-5-ylmethyl)glycyl]phenylalanine;
2-(7-nitro-2,3-dioxo-1,2,3,4-tetrahydroquinoxalin-5-ylmethylamino)-alanine;
3-(7-nitro-2,3-dioxo-1,2,3,4-tetrahydroquinoxalin-5-ylmethylamino)-propanol hydrochloride;
3-(7-nitro-2,3-dioxo-1,2,3,4-tetrahydroquinoxalin-5-ylmethylamino)-ethanol hydrochloride;
N-(7-nitro-2,3-dioxo-1,2,3,4-tetrahydroquinoxalin-5-ylmethyl)-5-dimethylamino-naphthalene-sulfonamide;
N-(7-nitro-2,3-dioxo-1,2,3,4-tetrahydroquinoxalin-5-ylmethyl)-2-benzyl-azidine;
2-[2-(7-nitro-2,3-dioxo-1,2,3,4-tetrahydroquinoxalin-5-yl)ethylamino]-acetic acid;
1-[2-(7-nitro-2,3-dioxo-1,2,3,4-tetrahydroquinoxalin-5-yl)ethyl]piperidine;
1-[2-(7-nitro-2,3-dioxo-1,2,3,4-tetrahydroquinoxalin-5-yl)ethyl]piperidin-4-one;
1-[2-(7-nitro-2,3-dioxo-1,2,3,4-tetrahydroquinoxalin-5-yl)ethyl]pyrrolidin-3-ol;
1-[2-(7-nitro-2,3-dioxo-1,2,3,4-tetrahydroquinoxalin-5-yl)ethyl]piperidine-4-carboxylic acid;
1-[?-(7-nitro-2,3-dioxo-1,2,3,4-tetrahydroquinoxalin-5-yl)ethyl]-4-acetylamino-piperidine;
1-[2-(7-nitro-2,3-dioxo-1,2,3,4-tetrahydroquinoxalin-5-yl)ethyl]pyrrolidine-2,5-dione;
1-[2-(7-nitro-2,3-dioxo-1,2,3,4-tetrahydroquinoxalin-5-yl)ethyl]piperidine-2,6-dione;
1-[2-(7-nitro-2,3-dioxo-1,2,3,4-tetrahydroquinoxalin-5-yl)ethyl]pyrrolidine;
N-{2-[2-(7-nitro-2,3-dioxo-1,2,3,4-tetrahydroquinoxalin-5-yl)ethyl]}-N-(pyrazin-2-yl)-amine;
N-{2-[2-(7-nitro-2,3-dioxo-1,2,3,4-tetrahydroquinoxalin-5-yl)ethyl]}-N-(thiazol-2-yl)-amine;
N-{2-[2-(7-nitro-2,3-dioxo-1,2,3,4-tetrahydroquinoxalin-5-yl)ethyl]}-quinoline-4-carboxylic acid amide;
N-[2-(7-nitro-2,3-dioxo-1,2,3,4-tetrahydroquinoxalin-5-yl)ethyl]-methanesulfonic acid amide;
N-[2-(7-nitro-2,3-dioxo-1,2,3,4-tetrahydroquinoxalin-5-yl)ethyl]-benzenesulfonic acid amide;
N-[2-(7-nitro-2,3-dioxo-1,2,3,4-tetrahydroquinoxalin-5-yl)ethyl]-acetamide; and
N-[2-(7-nitro-2,3-dioxo-1,2,3,4-tetrahydroquinoxalin-5-yl)ethyl]-(4-methoxy)-benzamide.

EXAMPLE 79

Tablets, each comprising 50 mg of active ingredient, for example 7-bromo-2,3-dioxo-1,2,3,4-tetrahydroquinoxalin-5-ylmethoxyacetic acid or a salt thereof, can be prepared as follows:

| Composition (10000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch and the mixture is moistened with an ethanolic solution of the gelatin and granulated through a sieve. After drying, the remainder of the potato starch, the magnesium stearate, the talc and the silicon dioxide are mixed in and the mixture is compressed to form tablets, each weighing 145.0 mg and comprising 50.0 mg of active ingredient; the tablets may, if desired, be provided with breaking notches for finer adaptation of the dose.

EXAMPLE 80

A sterile-filtered aqueous gelatin solution which comprises 20% cyclodextrins as solubilizer and which comprises 3 mg of 7-bromo-2,3-dioxo-1,2,3,4-tetrahydroquinoxalin-5-ylmethoxyacetic acid or of a salt, for example the sodium salt, thereof as active ingredient, is mixed under aseptic conditions, with heating, with a sterile gelatin solution that comprises phenol as preservative in such a manner that 1.0 ml of solution has the following composition:

| active ingredient | 3 mg |
|---|---|
| gelatin | 150.0 mg |
| phenol | 4.7 mg |
| dist. water with 20% cyclodextrins as solubilizer | 1.0 ml |

EXAMPLE 81

For the preparation of a sterile dry substance for injection, comprising 5 mg of 7-bromo-2,3-dioxo-1,2,3,4-tetrahydroquinoxalin-5-ylmethoxyacetic acid or of a salt, for example the sodium salt, thereof, 5 mg of one of the compounds of formula I mentioned in the preceding Examples as active ingredient are dissolved in 1 ml of an aqueous solution comprising 20 mg of mannitol and 20% cyclodextrins as solubilizer. The solution is sterile-filtered and introduced under aseptic conditions into a 2 ml ampoule, is deep-frozen and lyophilized. Before use, the lyophilizate is dissolved in 1 ml of distilled water or 1 ml of physiological saline solution. The solution is administered intramuscularly or intravenously. This formulation can also be introduced into double-chamber injection ampoules.

EXAMPLE 82

10000 film-coated tablets, each comprising 100 mg of 7-bromo-2,3-dioxo-1,2,3,4-tetrahydroquinoxalin-5-ylmethoxyacetic acid or a salt, for example the sodium salt, thereof, can be prepared as follows:

| active ingredient | 1000 g |
|---|---|
| corn starch | 680 g |
| colloidal silicic acid | 200 g |
| magnesium stearate | 20 g |
| stearic acid | 50 g |
| sodium carboxymethyl starch | 250 g |
| water | q.s. |

A mixture of one of the compounds of formula I mentioned in the preceding Examples as active ingredient, 50 g of corn starch and the colloidal silicic acid is processed with starch paste consisting of 250 g of corn starch and 2.2 kg of demineralized water to form a moist mass. The moist mass is forced through a sieve having a mesh size of 3 mm and is dried at 45° C. for 30 minutes in a fluidized bed dryer. The dried granules are pressed through a sieve having a mesh size of 1 mm, are mixed with a previously sieved mixture (1 mm sieve) of 330 g of corn starch, the magnesium stearate, the stearic acid and the sodium carboxymethyl starch, and are compressed to form slightly biconvex tablets.

EXAMPLE 83

In a manner analogous to that described in Examples 79 to 82, it is also possible to prepare pharmaceutical preparations comprising a different compound according to any one of Examples 1 to 78.

What is claimed is:
1. A 2,3-dioxo-1,2,3,4-tetrahydro-quinoxalinyl derivative of formula I

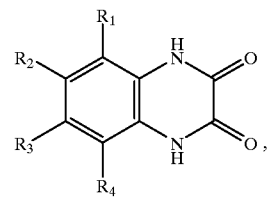

wherein
one of the radicals $R_1$ and $R_2$ is a group $R_5$ and the other is a group of formula —alk—N($R_8$)—X—$R_7$ (Ic) or —alk—N$^+$($R_8$)($R_9$)—X—$R_7$ A$^-$ (Id), $R_3$, $R_4$ and $R_5$ are each independently of the others hydrogen, lower alkyl, halogen, trifluoromethyl, cyano or nitro, $R_7$ is hydrogen; an aliphatic, cycloaliphatic or heterocycloaliphatic radical; cyano; acyl derived from carbonic acid or from a semiester or semiamide of carbonic acid, from sulfuric acid or from an aliphatic or aromatic sulfonic acid or from phosphoric acid or from a phosphonic acid ester; amino that is unsubstituted or aliphatically or araliphatically substituted and/or substituted by aliphatic, araliphatic or aromatic acyl; or an aromatic or heteroaromatic radical, $R_8$ is hydrogen; an aliphatic or araliphatic radical; or acyl derived from an aliphatic or araliphatic carboxylic acid or from an aliphatic or araliphatic semiester of carbonic acid, $R_7$, $R_8$ and $R_9$, together with X and the nitrogen atom bonding $R_8$, $R_9$ and X, form an unsubstituted or substituted quaternary heteroaryl radical bonded via the quaternary nitrogen atom, with A$^-$ being the anion of a protonic acid, alk is lower alkylene, and X (unless, together with the nitrogen atom bonding $R_8$, $R_9$ and X, it forms part of an optionally substituted quaternary heteroaryl radical is a divalent aliphatic, cycloaliphatic or araliphatic radical or a direct bond, with the proviso that in compounds of formula I wherein $R_1$, $R_3$ and $R_4$ are hydrogen and $R_2$ is a group of formula Ic, when alk is ethylene the group —N($R_8$)—X—$R_7$ is other than amino, dipropyl-amino and N-(2-phenylethyl)-N-propyl-amino, or a salt thereof.

2. A compound of formula I according to claim 1, wherein one of the radicals $R_1$ and $R_2$ is a group $R_5$ and the other is a group of formula —alk—N($R_8$)—X—$R_7$ (Ic) and —alk—N$^+$($R_8$)($R_9$)—X—$R_7$ A$^-$ (Id), —alk—O—X—$R_7$ (Ie) or —alk—S—X—$R_7$ (If), $R_3$, $R_4$ and $R_5$ are each independently of the others hydrogen, lower alkyl, halogen, trifluoromethyl, cyano or nitro, $R_7$ is hydrogen, lower alkyl, amino-lower alkyl, lower alkylamino-lower alkyl, di-lower alkylamino-lower alkyl, lower alkanoylamino-lower alkyl, hydroxy-lower alkyl, lower alkanoyloxy-lower alkyl, polyhalo-lower alkyl, lower alkoxy-lower alkyl, hydroxy-lower alkoxy-lower alkyl, lower alkoxy-lower alkoxy-lower alkyl or polyhalo-lower alkoxy-lower alkyl, 3- to 8-membered cycloalkyl, carboxycycloalkyl, lower alkoxycarbonylcycloalkyl, aminocycloalkyl or mono- or di-lower alkylaminocycloalkyl, pyrrolidino, oxopyrrolidinyl, carboxypyrrolidino, piperidino, carboxypiperidino, lower alkoxycarbonylpiperidino, morpholino or thiomorpholino, carboxy, lower alkoxycarbonyl; phenyl-lower alkoxycarbonyl that is unsubstituted or substituted by lower alkyl, lower alkoxy, hydroxy, halogen and/or by trifluoromethyl; carbamoyl, cyano, lower alkylcarbamoyl, di-lower alkylcarbamoyl, lower alkoxycarbonyl-lower alkylcarbamoyl, carboxy-lower alkylcarbamoyl, carbamoyl-lower alkylcarbamoyl, N-carbamoyl-lower alkyl-N-lower alkyl-carbamoyl; phenylcarbamoyl that is unsubstituted or substituted by lower alkyl, lower alkoxy, polyhalo-lower alkoxy, hydroxy, halogen, nitro, carboxy, lower alkoxycarbonyl, phenyl, phenyloxy and/or by trifluoromethyl; sulfo, lower alkanesulfonyl; benzylsulfonyl that is unsubstituted or substituted by lower alkyl, lower alkoxy, halogen, trifluoromethyl, carboxy and/or by lower alkoxycarbonyl; unsubstituted or di-lower alkylamino-substituted naphthalenesulfonyl, phosphono, tri-lower alkylphosphono, amino, lower alkylamino, di-lower alkylamino, lower alkanoylamino; phenyl-lower alkylamino, benzoylamino or naphthoylamino that is unsubstituted or substituted by lower alkyl, lower alkoxy, halogen and/or by trifluoromethyl; ureido, amidino; phenyl or naphthyl that is unsubstituted or substituted by lower alkyl, lower alkoxy, lower alkylenedioxy, lower alkylidenedioxy, hydroxy, lower alkoxycarbonyl, carboxy, carbamoyl, sulfamoyl, lower alkoxycarbonylamino, lower alkanoyl, halogen and/or by trifluoromethyl; furyl, lower alkylfuryl, thienyl, imidazolyl, oxazolyl, oxazolinyl (dihydrooxazolyl), carboxy-lower alkyl(oxo)oxazolinyl, thiazolyl, thiazolinyl (dihydrothiazolyl), carboxy-lower alkylthiazolyl, lower alkoxycarbonyl-lower alkylthiazolyl, tetrazolyl, pyridyl, pyrazinyl, indolyl, quinolinyl, benzazepinyl or carboxy-lower alkyl-2,3,4, 5-tetrahydro-1H-1-benzazepinyl, $R_8$ is hydrogen, lower alkyl, amino-lower alkyl, lower alkylamino-lower alkyl, di-lower alkylamino-lower alkyl, lower alkanoylamino-lower alkyl, hydroxy-lower alkyl, lower alkanoyloxy-lower alkyl, polyhalo-lower alkyl, lower alkoxy-lower alkyl, hydroxy-lower alkoxy-lower alkyl, lower alkoxy-lower alkoxy-lower alkyl, polyhalo-lower alkoxy-lower alkyl; phenyl-lower alkyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl; lower alkanoyl, lower alkenoyl; phenyl-lower alkanoyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl; lower alkoxycarbonyl, or phenyl-lower alkoxycarbonyl that is unsubstituted or substituted by lower alkyl, lower alkoxy, lower alkylenedioxy, lower alkylidenedioxy, hydroxy, lower alkoxycarbonyl, carboxy, carbamoyl, lower alkanoyl, halogen and/or by trifluoromethyl, $R_9$ is lower alkyl, lower alkenyl, lower alkynyl, or phenyl-lower alkyl that is unsubstituted or substituted by lower alkyl, lower alkoxy, halogen and/or by trifluoromethyl, or $R_7$, $R_8$ and $R_9$, together with X and the nitrogen atom bonding $R_8$, $R_9$ and X, form a pyridinium radical that is unsubstituted or substituted by $C_1$–$C_4$alkyl, amino, $C_1$–$C_4$alkylamino or by di-$C_1$–$C_4$-alkylamino, with A⁻ being the anion of a hydrohalic acid, lower alkanesulfonic acid or unsubstituted or lower alkyl- or halo-substituted benzenesulfonic acid, alk is lower alkylene, and X (unless, together with the nitrogen atom bonding $R_8$, $R_9$ and X, it forms part of an optionally substituted quaternary heteroaryl radical is lower alkylene, lower alkylidene, lower alkenylene, oxo-lower alkylene including carbonyl, oxo-lower alkylidene, dioxo-lower alkylene, oxo-lower alkenylene, hydroxy-lower alkylidene, oxo(hydroxy)-lower alkylene, amino-lower alkylene, amino-lower alkylidene, carboxy-lower alkylene, carboxy-lower alkylidene, carbamoyl-lower alkylidene, lower alkoxycarbonyl-lower alkylidene, lower alkoxycarbonyl-lower alkylene, ω-aza-α-oxo-lower alkylene or ω-aza-α-oxo-lower alkenylene, 3- to 7-membered cycloalkylidene, or unsubstituted or lower alkyl-, lower alkoxy-, lower alkylenedioxy-, lower alkylidenedioxy-, hydroxy-, lower alkoxycarbonyl-, carboxy-, carbamoyl-, lower alkanoyl-, halo- and/or trifluoromethyl-substituted phenyl-lower alkylidene or phenyl-lower alkylene, or a salt thereof.

3. A compound of formula I according to claim 1, wherein one of the radicals $R_1$ and $R_2$ is a group $R_5$ and the other is a group of formula (Ic), $R_3$ $R_4$ and $R_5$ are each independently of the others hydrogen, lower alkyl, halogen, cyano or nitro, $R_7$ is carboxy, lower alkoxycarbonyl; phenyl-lower alkoxycarbonyl that is unsubstituted or substituted by lower alkyl, lower alkoxy, hydroxy, halogen and/or by trifluoromethyl; carbamoyl; phenylcarbamoyl that is unsubstituted or substituted by lower alkyl, lower alkoxy, hydroxy, halogen, nitro, carboxy, lower alkoxycarbonyl, phenyl, phenyloxy and/or by trifluoromethyl; phosphono, mono-, di- or tri-lower alkylphosphono or tetrazolyl, $R_8$ is hydrogen or lower alkyl alk is lower alkylene, and X is lower alkylene, oxo-lower alkylene including carbonyl, lower alkylidene, amino-lower alkylidene, carboxy-lower alkylidene, lower alkoxycarbonyl-lower alkylidene, carbamoyl-lower alkylidene or, with the N($R_8$) group, ω-aza-α-oxo-lower alkylene or ω-aza-α-oxo-lower alkenylene bonded via the α-carbon atom; phenyl-lower alkylidene that is unsubstituted or substituted by lower alkyl, lower alkoxy, halogen and/or by trifluoromethyl, or a salt thereof.

4. A compound of formula I according to claim 1, wherein one of the radicals $R_1$ and $R_2$ is a group $R_5$ and the other is a group of formula —alk—N($R_8$)—X—$R_7$ (Ic), $R_3$, $R_4$ and $R_5$ are each independently of the others hydrogen, lower alkyl, halogen, cyano or nitro, $R_7$ is a phenyl, naphthyl, furyl, thienyl, pyridyl or 3- to 8-membered cycloalkyl radical that is unsubstituted or substituted by lower alkyl, lower alkoxy, carboxy, lower alkoxycarbonyl, unsubstituted or lower alkyl-, lower alkoxy-, hydroxy-, halo- and/or trifluoromethyl-substituted phenyl-lower alkoxycarbonyl, carbamoyl, unsubstituted or lower alkyl-, lower alkoxy-, hydroxy-, halo-, nitro-, carboxy-, lower alkoxycarbonyl-, phenyl-, phenyloxy- and/or trifluoromethyl-substituted phenylcarbamoyl, cyano, nitro, halogen and/or by trifluoromethyl, or is lower alkyl, amino-lower alkyl, lower alkylamino-lower alkyl, di-lower alkylamino-lower alkyl, lower alkanoylamino-lower alkyl, hydroxy-lower alkyl, lower alkanoyloxy-lower alkyl, polyhalo-lower alkyl, lower alkoxy-lower alkyl, hydroxy-lower alkoxy-lower alkyl, lower alkoxy-lower alkoxy-lower alkyl or polyhalo-lower alkoxy-lower alkyl, $R_8$ is hydrogen or lower alkyl, alk is lower alkylene, and X is oxo-lower alkylene, or a salt thereof.

5. A compound of formula I according to claim 1, wherein one of the radicals $R_1$ and $R_2$ is a group $R_5$ and the other is a group of formula —alk—N($R_8$)—X—$R_7$ (Ic) or —alk—N$^+$($R_8$)($R_9$)—X—$R_7$ A$^-$ (Id), $R_3$, $R_4$ and $R_5$ are each independently of the others hydrogen, $C_1$–$C_4$alkyl, halogen having an atomic number of up to and including 35, trifluoromethyl, cyano or nitro, $R_7$ is hydrogen, $C_1$–$C_7$alkyl, hydroxy-$C_1$–$C_4$alkyl, polyhalo-$C_1$–$C_4$alkyl, $C_1$–$C_4$alkoxy-$C_1$–$C_4$alkyl, 3- to 6-membered cycloalkyl, 3- to 6-membered carboxycycloalkyl, 3- to 6-membered aminocycloalkyl, pyrrolidino, carboxypyrrolidino, oxopyrrolidinyl, piperidino, carboxypiperidino, morpholino, thiomorpholino, carboxy, $C_1$–$C_4$alkoxycarbonyl, phenyl-$C_1$–$C_4$alkoxycarbonyl, carbamoyl, cyano, $C_1$–$C_4$alkylcarbamoyl, $C_1$–$C_4$alkoxycarbonylcarbamoyl, carboxy-$C_1$–$C_4$alkylcarbamoyl, carbamoyl-$C_1$–$C_4$alkylcarbamoyl, N-carbamoyl-$C_1$–$C_4$alkyl-N-$C_1$–$C_4$alkylcarbamoyl, N-carboxy-$C_1$–$C_4$alkyl-N-$C_1$–$C_4$alkyl-carbamoyl, carbamoyl-$C_1$–$C_4$alkylcarbamoyl, unsubstituted or carboxy-substituted phenyl-$C_1$–$C_4$alkylcarbamoyl; phenylcarbamoyl that is unsubstituted or substituted by $C_1$–$C_4$alkoxy, nitro, polyhalo-$C_1$–$C_4$alkoxy, phenyloxy and/or by $C_1$–$C_4$alkoxycarbonyl; sulfo, $C_1$–$C_4$alkanesulfonyl; benzylsulfonyl that is unsubstituted or substituted by $C_1$–$C_4$alkyl, $C_1$–$C_4$alkoxy and/or by carboxy; unsubstituted or di-$C_1$–$C_4$alkylamino-substituted naphthalenesulfonyl, phosphono, amino, $C_1$–$C_4$alkylamino, di-$C_1$–$C_4$alkylamino, $C_1$–$C_4$alkanoylamino, phenyl-$C_1$–$C_4$alkylamino, benzoylamino, naphthoylamino, ureido, amidino; phenyl or naphthyl that is unsubstituted or substituted by $C_1$–$C_4$alkyl, $C_1$–$C_4$alkoxy, $C_1$–$C_4$alkylenedioxy, $C_1$–$C_4$alkylidenedioxy, carboxy, sulfamoyl, $C_1$–$C_4$alkoxy-carbonylamino, $C_1$–$C_4$alkanoyloxy, hydroxy, halogen and/or by trifluoromethyl; furyl, $C_1$–$C_4$alkylfuryl, thienyl, imidazolyl, (oxo)oxazolinyl, thiazolyl, thiazolinyl (dihydrothiazolyl), carboxy-$C_1$–$C_4$alkylthiazolyl, $C_1$–$C_4$alkoxycarbonyl-$C_1$–$C_4$alkylthiazolyl, tetrazolyl, pyridyl, pyrazinyl, indolyl, quinolinyl, benzazepinyl or carboxy-$C_1$–$C_4$alkyl-2,3,4,5-tetrahydro-1H-1-benzazepinyl, $R_8$ is hydrogen, $C_1$–$C_4$alkyl, hydroxy-$C_1$–$C_4$alkyl, $C_1$–$C_4$alkoxy-$C_1$–$C_4$alkyl, hydroxy-$C_1$–$C_4$alkoxy-$C_1$–$C_4$alkyl, phenyl-$C_1$–$C_4$alkyl, pyridyl-$C_1$–$C_4$alkyl, $C_1$–$C_4$alkanoyl, such as acetyl, phenyl-$C_1$–$C_4$alkanoyl, $C_1$–$C_4$alkoxycarbonyl or phenyl-$C_1$-$C_4$alkoxycarbonyl, $R_9$ is lower alkyl or $R_7$, $R_8$ and $R_9$, together with X and the nitrogen atom bonding $R_8$, $R_9$ and X, form a pyridinium radical that is unsubstituted or substituted by amino, $C^1$–$C_4$alkylamino or by di-$C_1$–$C_4$alkylamino, with A$^-$ being the anion of a hydrohalic acid, alk is $C_1$–$C_4$alkylene or $C_1C_4$alkylidene, and X (unless, together with $R_7$ and $R_8$ and the nitrogen atom bonding $R_8$ and X or together with e nitrogen atom bonding $R_8$, $R_9$ and X, it forms part of an optionally substituted quaternary heteroaryl radical is a direct bond, $C_1$–$C_4$alkylene, $C_1$–$C_4$alkylidene, $C_1$–$C_4$alkenylene, oxo-$C_1$–$C_4$alkylene including carbonyl, dioxo-$C_1$–$C_4$alkylene including oxalo, oxo-$C_1$–$C_4$alkenylene, hydroxy-$C_1$–$C_4$alkylidene, oxo (hydroxy)-$C_1$–$C_4$alkylene, amino-$C_1$–$C_4$alkylene, amino-$C_1$–$C_4$alkylidene, carboxy-$C_1$–$C_4$alkylene, carboxy-$C_1$–$C_4$alkylidene, $C_1$–$C_4$alkoxycarbonyl-$C_1$–$C_4$alkylidene, $C_1$–$C_4$alkoxycarbonyl-$C_1$–$C_4$alkylene, ω-aza-α-oxo-$C_1$–$C_4$alkylene or ω-aza-α-oxo-$C_1$–$C_4$alkenylene, 3- to 7-membered cycloalkylidene or unsubstituted or halo- and/or trifluoromethyl-substituted phenyl-$C_1$–$C_4$alkylidene or phenyl-$C_1$–$C_4$alkylene, or a salt thereof.

6. A compound according to any one of claim 1, wherein $R_1$ is a group of formula —alk—N($R_8$)—X—$R_7$ (Ic), or —alk—N$^+$($R_8$)($R_9$)—X—$R_7$ A$^-$ (Id), and $R_2$ is a group $R_5$, wherein $R_3$, $R_4$, $R_5$, $R_7$, $R_8$, $R_9$, alk and X are as defined in claim 1, or a salt thereof.

7. A compound of formula I according to claim 1, wherein $R_1$ is a group of formula —alk—N($R_8$)—X—$R_7$ (Ic) or —alk—N$^+$($R_8$)($R_9$)—X—$R_7$A$^-$ (Id) and $R_2$ is a group $R_5$, $R_3$, $R_4$ and $R_5$ are each independently of the others hydrogen, $C_1$–$C_4$alkyl, halogen having an atomic number of up to and including 35, trifluoromethyl, cyano or nitro, $R_7$ is hydrogen, alkyl, hydroxy-$C_1$–$C_4$alkyl, polyhalo-$C_1$–$C_4$alkyl, 3- to 6-membered cycloalkyl, carboxy, $C_1$–$C_4$alkoxycarbonyl, phenyl-$C_1$–$C_4$alkoxycarbonyl, carbamoyl, phenylcarbamoyl, $C_1$–$C_4$alkanesulfonyl, amino, morpholino, benzoylamino; phenyl that is unsubstituted or substituted by carboxy, sulfamoyl, $C_1$–$C_4$alkoxy, $C_1$–$C_4$alkanoyloxy, halogen and/or by trifluoromethyl; furyl, thienyl, thiazolyl, thiazolinyl (dihydrothiazolyl), carboxy-$C_1$–$C_4$alkyl-thiazolyl, $C_1$–$C_4$alkoxycarbonyl-$C_1$–$C_4$alkylthiazolyl or pyridyl, $R_8$ is hydrogen, $C_1$–$C_4$alkyl, hydroxy-$C_1$–$C_4$alkyl, phenyl-$C_1$–$C_4$alkyl or pyridyl-$C_1$–$C_4$alkyl, $R_9$ is lower alkyl or $R_7$, $R_8$ and $R_9$, together with X and the nitrogen atom bonding $R_8$, $R_9$ and X, form an unsubstituted or amino-substituted pyridinium radical, with A being the anion of a hydro-halic acid, alk is $C_1$–$C_4$alkyl(id)ene, and X (unless, together with the nitrogen atom bonding $R_8$, $R_9$ and X, it forms part of an optionally substituted quaternary heteroaryl radical is a direct bond, $C_1$–$C_7$alkylene, $C_1$–$C_4$alkylidene, oxo-$C_1$–$C_4$alkylene including carbonyl, oxo-$C_1$–$C_4$alkenylene, amino-$C_1$–$C_4$alkylidene, carboxy-$C_1$–$C_4$alkylidene, $C_1$–$C_4$alkoxycarbonyl-$C_1$–$C_4$alkylidene, ω-aza-α-oxo-$C_1$–$C_4$alkylene or ω-aza-α-oxo-$C_1$–$C_4$alkenylene or unsubstituted or halo- and/or trifluoromethyl-substituted phenyl-$C_1$–$C_4$alkylidene, or a salt thereof.

8. A compound of formula I according to claim 1, wherein $R_1$ is a group of formula —alk—N($R_8$)—X—$R_7$ (Ic) or —alk—N$^+$($R_8$)($R_9$)—X—$R_7$ A$^-$ (Id) and $R_2$ is a group $R_5$, $R_3$ and $R_4$ are each independently of the other hydrogen, $C_1$–$C_4$alkyl, halogen having an atomic number of up to and including 35 or nitro, $R_5$ is hydrogen, $R_7$ is hydrogen, alkyl, polyhalo-$C_1$–$C_4$alkyl, 3- to 6-membered cycloalkyl, 3- to 6-membered azoxacycloalkyl, carboxy, $C_1$–$C_4$alkoxycarbonyl; phenyl that is unsubstituted or substituted by carboxy, sulfamoyl, $C_1$–$C_4$alkoxy, halogen and/or by trifluoromethyl; furyl, thiazolinyl (dihydrothiazolyl), carboxy-$C_1$–$C_4$alkylthiazolyl or $C_1$–$C_4$alkoxycarbonyl-$C_1$–$C_4$alkylthiazolyl, $R_8$ is hydrogen, $C_1$–$C_4$alkyl or pyridyl-$C_1$–$C_4$alkyl, $R_9$ is $C_1$–$C_4$alkyl or $R_7$, $R_8$ and $R_9$, together with X and the nitrogen atom bonding $R_8$, $R_9$ and X, form an unsubstituted or amino-substituted pyridinium radical, with A$^-$ being the anion of a hydrohalic acid, alk is $C_1$–$C_4$alkyl(id)ene, and X (unless together with the nitrogen atom bonding $R_8$, $R_9$ and X, it forms part of an optionally substituted quaternary heteroaryl radical is a direct bond, $C_1$–$C_7$alkylene, $C_1$–$C_4$alkylidene, oxo-$C_1$–$C_4$alkylene including carbonyl, amino-$C_1$–$C_4$alkylidene, carboxy-$C_1$–$C_4$alkylidene or unsubstituted or halo- and/or trifluoromethyl-substituted phenyl-$C_1$–$C_4$alkylidene, or a salt thereof.

9. A compound of formula I according to claim 1, wherein $R_1$ is a group of formula —alk—N($R_8$)—X—$R_7$ (Ic), $R_2$ is hydrogen, $R_3$ and $R_4$ are each independently of the other halogen having an atomic number of up to and including 35 or nitro, $R_7$ is carboxy, phenyl-$C_1$–$C_4$alkoxycarbonyl; phenylcarbamoyl that is unsubstituted or substituted by $C_1$–$C_4$alkyl, $C_1$–$C_4$alkoxy, hydroxy, halogen having an atomic number of up to and including 35, nitro, carboxy, $C_1$–$C_4$alkoxycarbonyl, phenyl, phenyloxy and/or by trifluoromethyl; tetrazoiyl, $R_8$ is hydrogen, alk is methylene, X is $C_1$–$C_4$alkylidene or, in formula Ic, is carbonyl, amino-$C_1$–$C_4$alkylidene, carboxy-$C_1$–$C_4$-alkylidene or, with the N($R_8$) group, ω-aza-α-oxo-$C_3$–$C_5$alkylene bonded via the α-carbon atom or a salt thereof.

10. A compound of formula I according to claim 1, wherein $R_1$ is a group of formula —alk—N($R_8$)—X—$R_7$ (Ic) or —alk—N$^+$($R_8$)($R_9$)—X—$R_7$ A$^-$ (Id) and $R_2$ is a group $R_5$, $R_3$ and $R_4$ are each independently of the other hydrogen, $C_1$–$C_4$alkyl, halogen having an atomic number of up to and including 35 or nitro, $R_5$ is hydrogen, $R_7$ is hydrogen, alkyl, polyhalo-$C_1$–$C_4$alkyl, 3- to 6-membered cycloalkyl, 3- to 6-membered azoxacycloalkyl, carboxy, $C_1$–$C_4$alkoxycarbonyl; phenyl that is unsubstituted or substituted by carboxy, sulfamoyl, $C_1$–$C_4$alkoxy, halogen and/or by trifluoromethyl; furyl, thiazolinyl (dihydrothiazolyl), carboxy-$C_1$–$C_4$alkylthiazolyl or $C_1$–$C_4$alkoxycarbonyl-$C_1$–$C_4$alkylthiazolyl, $R_8$ is hydrogen, $C_1$–$C_4$alkyl or pyridyl-$C_1$–$C_4$alkyl, alk is $C_1$–$C_4$alkyl(id)ene, and X is a direct bond, $C_1$–$C_7$alkylene, $C_1$–$C_4$alkylidene, oxo-$C_1$–$C_4$alkylene including carbonyl, oxo-$C_1$–$C_4$alkenylene, amino-$C_1$–$C_4$alkylidene, carboxy-$C_1$–$C_4$alkylidene, $C_1$–$C_4$alkoxycarbonyl-$C_1$–$C_4$alkylidene, ω-aza-α-oxo-$C_1$–$C_4$alkylene or ω-aza-α-oxo-$C_1$–$C_4$alkenylene, or unsubstituted or halo- and/or trifluoromethyl-substituted phenyl-$C_1$–$C_4$alkylidene, or a salt thereof.

11. A compound of formula I according to claim 1, wherein $R_1$ is a group of formula —alk—N($R_8$)—X—$R_7$ (Ic), $R_2$ is hydrogen, Ra and $R_4$ are each independently of the other halogen having an atomic number of up to and including 35 or nitro, $R_6$ is amino, $R_7$ is carboxy, $R_8$ is hydrogen piperidinylene radical, alk is methylene and X is $C_1$–$C_4$alkylidene or, with the N($R_8$) group, forms ω-aza-α-oxo-$C_3$–$C_5$alkylene, bonded via the α-carbon atom piperidinylene radical, or a salt thereof.

12. A compound of formula I according to claim 1, wherein $R_1$ is a group of formula —alk—N($R_8$)—X—$R_7$ (Ic), $R_2$, $R_3$, $R_4$ and $R_5$ are each independently of the others hydrogen, $C_1$–$C_4$alkyl, halogen having an atomic number of up to and including 35, cyano or nitro, $R_7$ is a phenyl, furyl, thienyl or pyridyl radical that is unsubstituted or substituted by $C_1$–$C_4$-alkyl, $C_1$–$C_4$alkoxy, carboxy, $C_1$–$C_4$alkoxycarbonyl, carbamoyl, cyano, nitro, halogen and/or by trifluoromethyl, or is 3- to 8-membered cycloalkyl, $C_1$–$C_7$alkyl, amino-$C_1$–$C_4$alkyl or polyhalo-$C_1C_4$alkyl, $R_8$ is hydrogen, alk is methylene and X is carbonyl, or a salt thereof.

13. A compound of formula I according to claim 1, wherein $R_2$ is a group $R_5$ and $R_1$ is a group of formula —alk—N($R_8$)—X—$R_7$ (Ic) or —alk—N$^+$($R_8$)($R_9$)—X—$R_7$ A$^-$ (Id), $R_3$ and $R_4$ are each independently of the other hydrogen, $C_1$–$C_4$alkyl, halogen having an atomic number of up to and including 35 or nitro, $R_5$ is hydrogen, $R_7$ is 3- to 6-membered cycloalkyl, morpholino, carboxy, $C_1$–$C_4$alkoxycarbonyl, thiazolinyl (dihydrothiazolyl) or $C_1$–$C_4$alkoxycarbonyl-$C_1$–$C_4$alkylthiazolyl, $R_8$ is hydrogen or $C_1$–$C_4$alkyl, alk is methylene, and X is a direct bond, $C_1$–$C_7$alkylene, amino-$C_1$–$C_4$alkylidene or carboxy-$C_1$–$C_4$alkylidene, or a salt thereof.

14. A method of treating a pathological condition mediated by the blocking of AMPA, kainate and/or glycine binding sites of the NMDA receptor comprising administering to a subject in need of such treatment a therapeutically effective amount of a compound of formula I according to claim 1, or a pharmaceutically acceptable salt thereof.

15. A pharmaceutical composition comprising a pharmaceutically acceptable carrier or diluent and a therapeutically effective amount of a compound of formula I according to claim 1, or a pharmaceutically acceptable salt thereof.

16. A compound according to claim 1 selected from the group consisting of:

N-(7-bromo-2,3-dioxo-1,2,3,4-tetrahydroquinoxalin-5-ylmethyl)-glycine;

N-(2,3-dioxo-7-nitro-1,2,3,4-tetrahydroquinoxalin-5-ylmethyl)-glycine;

N-(2,3-dioxo-7-nitro-1,2,3,4-tetrahydroquinoxalin-5-ylmethyl)-piperidine-4-carboxylic acid;

7-bromo-2,3-dioxo-1,2,3,4-tetrahydroquinoxalin-5-ylmethoxyacetic acid;

N-(7-nitro-2,3-dioxo-1,2,3,4-tetrahydroquinoxalin-5-ylmethyl)-aminomethanephosphonic acid;

1-(7-nitro-2,3-dioxo-1,2,3,4-tetrahydroquinoxalin-5-ylmethylamino)-ethanephosphonic acid;

7-bromo-2,3-dioxo-1,2,3,4-tetrahydroquinoxalin-5-ylmethylaminomethanephosphonic acid; and 1-(7-bromo-2,3-dioxo-1,2,3,4-tetrahydroquinoxalin-5-ylmethylamino)-ethanephosphonic acid;

or a salt thereof.

* * * * *

UNITED STATES PATENT AND TRADEMARK OFFICE
CERTIFICATE OF CORRECTION

PATENT NO.   : 6,080,743
DATED        : June 27, 2000
INVENTOR(S)  : Acklin et al.

It is certified that error appears in the above-identified patent and that said Letters Patent is hereby corrected as shown below:

Column 78, claim 2,
Line 3, change "and" to -- or --.
Line 4, after the comma delete "alk-O-X-".
Line 5, delete line 5 in its entirety.

Column 80, claim 3,
Line 3, after "formula", insert -- alk - $N(R_8)$-X-$R_7$ --.

Column 81, claim 5,
Line 6, from the bottom of the page; delete "such as acetyl,".

Column 82, claim 5,
Line 2, change "$C^1$-$C_4$" to -- $C_1$-$C_4$ --.
Line 5, after the comma, delete the remainder of the line.
Line 6, before "together", delete "bonding $R_8$ and X or".
Line 6, change "e" to -- the --.

Column 82, claim 6,
Line 1, after "to", delete "any one of".

UNITED STATES PATENT AND TRADEMARK OFFICE
CERTIFICATE OF CORRECTION

PATENT NO. : 6,080,743
DATED : June 27, 2000
INVENTOR(S) : Acklin et al.

It is certified that error appears in the above-identified patent and that said Letters Patent is hereby corrected as shown below:

Column 82, claim 7,
Line 24, after "with", change "A" to -- $A^-$ --.

Column 84, claim 11,
Line 5, change "Ra" to -- $R_3$ --.
Line 8, delete in its entirety.
Line 10, after "hydrogen", delete "piperidinylene radical".
Line 14, should read "atom,"

Column 84, claim 12,
Line 12, change the second "$C_1C_4$" to -- $C_1$-$C_4$ --.

Signed and Sealed this

Twenty-fifth Day of September, 2001

Attest:

NICHOLAS P. GODICI
Attesting Officer  Acting Director of the United States Patent and Trademark Office